US012415842B2

(12) United States Patent
Oh et al.

(10) Patent No.: US 12,415,842 B2
(45) Date of Patent: *Sep. 16, 2025

(54) IMMUNOSTIMULATING IL-2 ANALOGS

(71) Applicant: HANMI PHARM. CO., LTD., Hwaseong-si (KR)

(72) Inventors: Euh Lim Oh, Hwaseong-si (KR); Sang Yun Kim, Hwaseong-si (KR); Yong Ho Heo, Hwaseong-si (KR); Jin Young Kim, Hwaseong-si (KR); Cho Rong Park, Hwaseong-si (KR); Jun Sub Park, Hwaseong-si (KR); Hyun Soo Ryu, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 118 days.

This patent is subject to a terminal disclaimer.

(21) Appl. No.: 18/349,656

(22) Filed: Jul. 10, 2023

(65) Prior Publication Data

US 2023/0348550 A1 Nov. 2, 2023

Related U.S. Application Data

(62) Division of application No. 17/915,808, filed as application No. PCT/KR2021/004028 on Mar. 31, 2021, now Pat. No. 11,746,137.

(30) Foreign Application Priority Data

Mar. 31, 2020 (KR) ........................ 10-2020-0039476

(51) Int. Cl.
*C07K 14/55* (2006.01)
*G01N 33/68* (2006.01)

(52) U.S. Cl.
CPC ......... *C07K 14/55* (2013.01); *G01N 33/6869* (2013.01)

(58) Field of Classification Search
CPC ..................................................... C07K 14/55
See application file for complete search history.

(56) References Cited

U.S. PATENT DOCUMENTS

| | | | |
|---|---|---|---|
| 9,428,567 B2 | 8/2016 | Garcia | |
| 11,746,137 B2 * | 9/2023 | Oh ........................ | C07K 14/55 530/351 |
| 2005/0142106 A1 | 6/2005 | Wittrup et al. | |
| 2006/0234205 A1 | 10/2006 | Cao et al. | |
| 2014/0046026 A1 | 2/2014 | Garcia et al. | |
| 2019/0321446 A1 | 10/2019 | Higginson-Scott et al. | |
| 2021/0101953 A1 | 4/2021 | Sun et al. | |

FOREIGN PATENT DOCUMENTS

| | | |
|---|---|---|
| AU | 2007201663 A1 | 10/2008 |
| CA | 2019714 A1 | 12/1990 |
| CN | 1309705 A | 8/2001 |
| CN | 101426916 A | 5/2009 |
| CN | 107266553 A | 10/2017 |
| JP | 2016-533167 A | 10/2016 |
| KR | 10-2015-0087130 A | 7/2015 |
| KR | 10-2016-0134989 A | 11/2016 |
| KR | 10-2017-0070091 A | 6/2017 |
| KR | 10-1989201 B1 | 6/2019 |
| KR | 10-2413691 B1 | 6/2022 |
| WO | 89/04665 A2 | 6/1989 |
| WO | 90/00565 A1 | 1/1990 |
| WO | 2004/022593 A3 | 3/2004 |
| WO | 2005/007121 A2 | 1/2005 |
| WO | 2005/007121 A3 | 1/2005 |
| WO | 2005/086798 A2 | 9/2005 |
| WO | 2015/164815 A1 | 10/2015 |
| WO | 2018/234862 A1 | 12/2018 |
| WO | 2019/147837 A2 | 8/2019 |
| WO | 2019/196815 A1 | 10/2019 |
| WO | 2019/246404 A1 | 12/2019 |
| WO | 2020/020783 A1 | 1/2020 |
| WO | 2020/057646 A1 | 3/2020 |
| WO | 2020/130300 A1 | 6/2020 |
| WO | 2020/228791 A1 | 11/2020 |
| WO | 2021/120350 A1 | 6/2021 |
| WO | 2021/178833 A2 | 9/2021 |

OTHER PUBLICATIONS

International Search Report for PCT/KR2021/004028 dated, Jul. 26, 2021 (PCT/ISA/210).
Australian Office Action for AU Application No. 2021202825 dated Jun. 3, 2021.
Australian Office Action for AU Application No. 2021202825 dated May 31, 2022.
Australian Office Action (Acceptance) for AU Application No. 2021202825 dated Jun. 16, 2022.
Extended European Search Report dated Jul. 15, 2024 in Application No. 21781220.5.

* cited by examiner

*Primary Examiner* — Prema M Mertz
(74) *Attorney, Agent, or Firm* — Sughrue Mion, PLLC

(57) ABSTRACT

Modifications to interleukin-2 alpha receptors are disclosed. Interleukin-2 analogs with increased binding affinity for interleukin-2 beta receptors are disclosed.

5 Claims, 3 Drawing Sheets

Specification includes a Sequence Listing.

SEQUENCE LISTING

Sequence total quantity: 417
SEQ ID NO: 1        moltype = AA    length = 133
FEATURE             Location/Qualifiers

```
source                  1..133
                        mol_type = protein
                        organism = Homo sapiens
SEQUENCE: 1
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 2            moltype = AA  length = 132
FEATURE                 Location/Qualifiers
REGION                  1..132
                        note = IL-2 analog 1
source                  1..132
                        mol_type = protein
                        organism = synthetic construct
SEQUENCE: 2
PTSSSTKKTQ LQLEHLLLDL QMILNGINNY KNPKLTRMLT FKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 3            moltype = AA  length = 132
FEATURE                 Location/Qualifiers
REGION                  1..132
                        note = IL-2 analog 2
source                  1..132
                        mol_type = protein
                        organism = synthetic construct
SEQUENCE: 3
PTSSSTKKTQ LQLEHLLLDL QMILNGINNY KNPKLTRMLT FKFYMPKKAT ELKHLQCLEE    60
ELKPLEEVLN LAQSKNFHLR PRDLICNINV IVLELKGSET TFMCEYADET ATIVEFLNRW   120
ITFSQSIIST LT                                                      132

SEQ ID NO: 4            moltype = AA  length = 132
FEATURE                 Location/Qualifiers
REGION                  1..132
                        note = IL-2 analog 3
source                  1..132
                        mol_type = protein
                        organism = synthetic construct
SEQUENCE: 4
PTSSSTKKTQ LQLEHLLLDL QMILNGINNY CNPKLTRMLT FKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 5            moltype = AA  length = 132
FEATURE                 Location/Qualifiers
REGION                  1..132
                        note = IL-2 analog 4
source                  1..132
                        mol_type = protein
                        organism = synthetic construct
SEQUENCE: 5
PTSSSTKKTQ LQLEHLLLDL QMILNGINNY KNPCLTRMLT FKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 6            moltype = AA  length = 132
FEATURE                 Location/Qualifiers
REGION                  1..132
                        note = IL-2 analog 5
source                  1..132
                        mol_type = protein
                        organism = synthetic construct
SEQUENCE: 6
PTSSSTKKTQ LQLEHLLLDL QMILNGINNY KNPKLTRMLT FCFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 7            moltype = AA  length = 132
FEATURE                 Location/Qualifiers
REGION                  1..132
                        note = IL-2 analog 6
source                  1..132
                        mol_type = protein
                        organism = synthetic construct
SEQUENCE: 7
PTSSSTKKTQ LQLEHLLLDL QMILNGINNY KNPKLTRMLT FKFYMPCKAT ELKHLQCLEE    60
ELKPLEEVLN LAQSKNFHLR PRDLISNINV IVLELKGSET TFMCEYADET ATIVEFLNRW   120
ITFSQSIIST LT                                                      132
```

```
SEQ ID NO: 8              moltype = AA   length = 132
FEATURE                   Location/Qualifiers
REGION                    1..132
                          note = IL-2 analog 7
source                    1..132
                          mol_type = protein
                          organism = synthetic construct
SEQUENCE: 8
PTSSSTKKTQ LQLEHLLLDL QMILNGINNY KNPKLTRMLT FKFYMPKCAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 9              moltype = AA   length = 132
FEATURE                   Location/Qualifiers
REGION                    1..132
                          note = IL-2 analog 9
source                    1..132
                          mol_type = protein
                          organism = synthetic construct
SEQUENCE: 9
PTSSSTKKTQ LQLEHLLLDL QMILNGINNY KNPKLTRMLT FKFYMPKKAT ELKHLQCLEE    60
ELKPLEEVLN LAQSCNFHLR PRDLISNINV IVLELKGSET TFMCEYADET ATIVEFLNRW   120
ITFSQSIIST LT                                                      132

SEQ ID NO: 10             moltype = AA   length = 132
FEATURE                   Location/Qualifiers
REGION                    1..132
                          note = IL-2 analog 10
source                    1..132
                          mol_type = protein
                          organism = synthetic construct
SEQUENCE: 10
PTSSSTKKTQ LQLEHLLLDL QMILNGINNY KNPKLTAMLT FKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 11             moltype = AA   length = 132
FEATURE                   Location/Qualifiers
REGION                    1..132
                          note = IL-2 analog 10
source                    1..132
                          mol_type = protein
                          organism = synthetic construct
SEQUENCE: 11
PTSSSTKKTQ LQLEHLLLDL QMILNGINNY KNPKLTRMLT KKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 12             moltype = AA   length = 132
FEATURE                   Location/Qualifiers
REGION                    1..132
                          note = IL-2 analog 11
source                    1..132
                          mol_type = protein
                          organism = synthetic construct
SEQUENCE: 12
PTSSSTKKTQ LQLEHLLLDL QMILNGINNY KNPKLTRMLT AKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 13             moltype = AA   length = 132
FEATURE                   Location/Qualifiers
REGION                    1..132
                          note = IL-2 analog 12
source                    1..132
                          mol_type = protein
                          organism = synthetic construct
SEQUENCE: 13
PTSSSTKKTQ LQLEHLLLDL QMILNGINNY KNPKLTAMLT KKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 14             moltype = AA   length = 132
FEATURE                   Location/Qualifiers
REGION                    1..132
                          note = IL-2 analog 13
source                    1..132
                          mol_type = protein
```

```
                                  -continued
                        organism = synthetic construct
SEQUENCE: 14
PTSSSTKKTQ LQLEHLLLDL QMILNGINNY KNPKLTAMLT AKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 15           moltype = AA  length = 132
FEATURE                 Location/Qualifiers
REGION                  1..132
                        note = IL-2 analog 14
source                  1..132
                        mol_type = protein
                        organism = synthetic construct
SEQUENCE: 15
PTSSSTKKTQ LQLEHLLYDL QMILNGINNY KNPKLTAMLT KKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 16           moltype = AA  length = 132
FEATURE                 Location/Qualifiers
REGION                  1..132
                        note = IL-2 analog 15
source                  1..132
                        mol_type = protein
                        organism = synthetic construct
SEQUENCE: 16
PTSSSTKKTQ LQLEHLLLDL QMILNGINNY KNPKLTAMLT KKFYMPKKAT ELKHLQCLEE    60
ELKPLEEVLN LAQSKNFHLR PRELISNINV IVLELKGSET TFMCEYADET ATIVEFLNRW   120
ITFSQSIIST LT                                                      132

SEQ ID NO: 17           moltype = AA  length = 132
FEATURE                 Location/Qualifiers
REGION                  1..132
                        note = IL-2 analog 16
source                  1..132
                        mol_type = protein
                        organism = synthetic construct
SEQUENCE: 17
PTSSSTKKTQ LQLEHLLLDL QMILNGINNY KNPKLTAMLT KKFYMPKKAT ELKHLQCLEE    60
ELKPLEEVLN LAQSKNFHLR PRDLISQINV IVLELKGSET TFMCEYADET ATIVEFLNRW   120
ITFSQSIIST LT                                                      132

SEQ ID NO: 18           moltype = AA  length = 132
FEATURE                 Location/Qualifiers
REGION                  1..132
                        note = IL-2 analog 17
source                  1..132
                        mol_type = protein
                        organism = synthetic construct
SEQUENCE: 18
PTSSSTKKTQ LQLEHLLLDL QMILNGINNY KNPKLTAMLT KKFYMPKKAT ELKHLQCLEE    60
ELKPLEEVLN LAQSKNFHLR PRDLISNINT IVLELKGSET TFMCEYADET ATIVEFLNRW   120
ITFSQSIIST LT                                                      132

SEQ ID NO: 19           moltype = AA  length = 132
FEATURE                 Location/Qualifiers
REGION                  1..132
                        note = IL-2 analog 18
source                  1..132
                        mol_type = protein
                        organism = synthetic construct
SEQUENCE: 19
PTSSSTKKTQ LQLEHLLLDL QMILNGINNY KNPKLTAMLT KKFYMPKKAT ELKHLQCLEQ    60
ELKPLEEVLN LAQSKNFHLR PRDLISNINV IVLELKGSET TFMCEYADET ATIVEFLNRW   120
ITFSQSIIST LT                                                      132

SEQ ID NO: 20           moltype = AA  length = 132
FEATURE                 Location/Qualifiers
REGION                  1..132
                        note = IL-2 analog 19
source                  1..132
                        mol_type = protein
                        organism = synthetic construct
SEQUENCE: 20
PTSSSTKKTQ LQLEHLLLDL QMILNGINNY KNPKLTAMLT KKFYMPKKAT ELKHLQCLEE    60
ELKPLEEVLN LAQSKNFHLD PRDLISNINV FVLELKGSET TFMCEYADET ATIVEFLNRW   120
ITFSQSIIST LT                                                      132

SEQ ID NO: 21           moltype = AA  length = 132
```

```
FEATURE                 Location/Qualifiers
REGION                  1..132
                        note = IL-2 analog 20
source                  1..132
                        mol_type = protein
                        organism = synthetic construct
SEQUENCE: 21
PTSSSTKKTQ LQLEHLLLDL QMILNGINNY KNPKLTAMLT KKFYMPKKAT ELKHLQCLEE    60
ELKPLEEVLN LAQSKNFHLR PRDVVSNINV FVLELKGSET TFMCEYADET ATIVEFLNRW   120
ITFSQSIIST LT                                                      132

SEQ ID NO: 22           moltype = AA  length = 132
FEATURE                 Location/Qualifiers
REGION                  1..132
                        note = IL-2 analog 21
source                  1..132
                        mol_type = protein
                        organism = synthetic construct
SEQUENCE: 22
PTSSSTKKTQ LQLEHLLLDL QMILNGINNY KNPKLTAMLT KKFYMPKKAT ELKHLQCLEE    60
ELKPLEEVLN LAQSKNFHFD PRDVVSNINV FVLELKGSET TFMCEYADET ATIVEFLNRW   120
ITFSQSIIST LT                                                      132

SEQ ID NO: 23           moltype = AA  length = 132
FEATURE                 Location/Qualifiers
REGION                  1..132
                        note = IL-2 analog 22
source                  1..132
                        mol_type = protein
                        organism = synthetic construct
SEQUENCE: 23
PTSSSTKKTQ VQLEHLLLDL QMILNGINNY KNPKLTAMLT KKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 24           moltype = AA  length = 132
FEATURE                 Location/Qualifiers
REGION                  1..132
                        note = IL-2 analog 23
source                  1..132
                        mol_type = protein
                        organism = synthetic construct
SEQUENCE: 24
PTSSSTKKTQ FQLEHLLLDL QMILNGINNY KNPKLTAMLT KKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 25           moltype = AA  length = 132
FEATURE                 Location/Qualifiers
REGION                  1..132
                        note = IL-2 analog 24
source                  1..132
                        mol_type = protein
                        organism = synthetic construct
SEQUENCE: 25
PTSSSTKKTQ LQLEHLLVDL QMILNGINNY KNPKLTAMLT KKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 26           moltype = AA  length = 132
FEATURE                 Location/Qualifiers
REGION                  1..132
                        note = IL-2 analog 25
source                  1..132
                        mol_type = protein
                        organism = synthetic construct
SEQUENCE: 26
PTSSSTKKTQ LQLEHLLFDL QMILNGINNY KNPKLTAMLT KKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 27           moltype = AA  length = 132
FEATURE                 Location/Qualifiers
REGION                  1..132
                        note = IL-2 analog 26
source                  1..132
                        mol_type = protein
                        organism = synthetic construct
SEQUENCE: 27
```

```
PTSSSTKKTQ LQLEHLLLDL QMILNGINNY KNPKLTAMLT KKFYMPKKAT ELKHLQCLEE    60
ELKPLEEVLN LAQSKNFHLR PRDLISNFNV IVLELKGSET TFMCEYADET ATIVEFLNRW   120
ITFSQSIIST LT                                                      132

SEQ ID NO: 28           moltype = AA  length = 132
FEATURE                 Location/Qualifiers
REGION                  1..132
                        note = IL-2 analog 27
source                  1..132
                        mol_type = protein
                        organism = synthetic construct
SEQUENCE: 28
PTSSSTKKTQ LQLEHLLLDL QMILNGINNY KNPKLTAMLT KKFYMPKKAT ELKHLQCLEE    60
ELKPLEEVLN LAQSKNFHLR PRDLISNINF IVLELKGSET TFMCEYADET ATIVEFLNRW   120
ITFSQSIIST LT                                                      132

SEQ ID NO: 29           moltype = AA  length = 132
FEATURE                 Location/Qualifiers
REGION                  1..132
                        note = IL-2 analog 28
source                  1..132
                        mol_type = protein
                        organism = synthetic construct
SEQUENCE: 29
PTSSSTKKTQ LQLEHLLLDL QMILNGINNY KNPKLTAMLT KKFYMPKKAT ELKHLQCLEE    60
ELKPLEEVLN LAQSKNFHLR PRDLISNINV IVVELKGSET TFMCEYADET ATIVEFLNRW   120
ITFSQSIIST LT                                                      132

SEQ ID NO: 30           moltype = AA  length = 132
FEATURE                 Location/Qualifiers
REGION                  1..132
                        note = IL-2 analog 29
source                  1..132
                        mol_type = protein
                        organism = synthetic construct
SEQUENCE: 30
PTSSSTKKTQ LQLEHLLLDL QMILNGINNY KNPKLTAMLT KKFYMPKKAT ELKHLQCLEE    60
ELKPLEEVLN LAQSKNFHLR PRDLISNINV IVLELKGSET TFMCEYADET ATIVEFLNRW   120
ITFSTSIIST LT                                                      132

SEQ ID NO: 31           moltype = AA  length = 132
FEATURE                 Location/Qualifiers
REGION                  1..132
                        note = IL-2 analog 30
source                  1..132
                        mol_type = protein
                        organism = synthetic construct
SEQUENCE: 31
PTSSSTKKTQ LQLEHLLLDL QMILNGINNY KNPKLTAMLT FKFYMPKKAT ELKHLQCLEE    60
ELKPLEEVLN LAQSKNFHLD PRDLISNINV FVLELKGSET TFMCEYADET ATIVEFLNRW   120
ITFSQSIIST LT                                                      132

SEQ ID NO: 32           moltype = AA  length = 132
FEATURE                 Location/Qualifiers
REGION                  1..132
                        note = IL-2 analog 31
source                  1..132
                        mol_type = protein
                        organism = synthetic construct
SEQUENCE: 32
PTSSSTKKTQ LQLEHLLLDL QMILNGINNY KNPKLTAMLT FKFYMPKKAT ELKHLQCLEE    60
ELKPLEEVLN LAQSKNFHLR PRELISNINV IVLELKGSET TFMCEYADET ATIVEFLNRW   120
ITFSQSIIST LT                                                      132

SEQ ID NO: 33           moltype = AA  length = 132
FEATURE                 Location/Qualifiers
REGION                  1..132
                        note = IL-2 analog 32
source                  1..132
                        mol_type = protein
                        organism = synthetic construct
SEQUENCE: 33
PTSSSTKKTQ LQLEHLLLDL QMILNGINNY KNPKLTAMLT FKFYMPKKAT ELKHLQCLEE    60
ELKPLEEVLN LAQSKNFHLD PRELISNINV FVLELKGSET TFMCEYADET ATIVEFLNRW   120
ITFSQSIIST LT                                                      132

SEQ ID NO: 34           moltype = AA  length = 132
FEATURE                 Location/Qualifiers
REGION                  1..132
```

-continued

```
                    note = IL-2 analog 33
source              1..132
                    mol_type = protein
                    organism = synthetic construct
SEQUENCE: 34
PTSSSTKKTQ LQLEHLLLDL QMILNGINNY KNPKLTAMLT FKFYMPKKAT ELKHLQCLEE   60
ELKPLEEVLN LAQSKNFHFR PRDLISNINV IVLELKGSET TFMCEYADET ATIVEFLNRW  120
ITFSQSIIST LT                                                     132

SEQ ID NO: 35           moltype = AA   length = 132
FEATURE                 Location/Qualifiers
REGION                  1..132
                        note = IL-2 analog 34
source                  1..132
                        mol_type = protein
                        organism = synthetic construct
SEQUENCE: 35
PTSSSTKKTQ LQLEHLLLDL QMILNGINNY KNPKLTAMLT FKFYMPKKAT ELKHLQCLEE   60
ELKPLEEVLN LAQSKNFHFR PRELISNINV IVLELKGSET TFMCEYADET ATIVEFLNRW  120
ITFSQSIIST LT                                                     132

SEQ ID NO: 36           moltype = AA   length = 132
FEATURE                 Location/Qualifiers
REGION                  1..132
                        note = IL-2 analog 35
source                  1..132
                        mol_type = protein
                        organism = synthetic construct
SEQUENCE: 36
PTSSSTKKTQ LQLEHLLLDL QMILNGINNY KNPKLTAMLT FKFYMPKKAT ELKHLQCLEE   60
ELKPLEEVLN LAQSKNFHLR PRDLISNINV IVFEFKGSET TFMCEYADET ATIVEFLNRW  120
ITFSQSIIST LT                                                     132

SEQ ID NO: 37           moltype = AA   length = 132
FEATURE                 Location/Qualifiers
REGION                  1..132
                        note = IL-2 analog 36
source                  1..132
                        mol_type = protein
                        organism = synthetic construct
SEQUENCE: 37
PTSSSTKKTQ LQLEHLLLDL QMILNGINNY KNPKLTAMLT FKFYMPKKAT ELKHLQCLEE   60
ELKPLEEVLN LAQSKNFHLR PRDLISNINV IVFEVKGSET TFMCEYADET ATIVEFLNRW  120
ITFSQSIIST LT                                                     132

SEQ ID NO: 38           moltype = AA   length = 132
FEATURE                 Location/Qualifiers
REGION                  1..132
                        note = IL-2 analog 37
source                  1..132
                        mol_type = protein
                        organism = synthetic construct
SEQUENCE: 38
PTSSSTKKTQ LQLEHLLLDL QMILNGINNY KNPKLTAMLT FKFYMPKKAT ELKHLQCLEE   60
ELKPLEEVLN LAQSKNFHLR PRDLISNINV IVFEIKGSET TFMCEYADET ATIVEFLNRW  120
ITFSQSIIST LT                                                     132

SEQ ID NO: 39           moltype = AA   length = 132
FEATURE                 Location/Qualifiers
REGION                  1..132
                        note = IL-2 analog 38
source                  1..132
                        mol_type = protein
                        organism = synthetic construct
SEQUENCE: 39
PTSSSTKKTQ LQLEHLLLDL QMILNGINNY KNPKLTAMLT KKFYMPKKAT ELKHLQCLEE   60
ELKPLEEVLN LAQSKNFHLD PRDLISNINV FVFEFKGSET TFMCEYADET ATIVEFLNRW  120
ITFSQSIIST LT                                                     132

SEQ ID NO: 40           moltype = AA   length = 132
FEATURE                 Location/Qualifiers
REGION                  1..132
                        note = IL-2 analog 39
source                  1..132
                        mol_type = protein
                        organism = synthetic construct
SEQUENCE: 40
PTSSSTKKTQ LQLEHLLLDL QMILNGINNY KNPKLTAMLT KKFYMPKKAT ELKHLQCLEE   60
ELKPLEEVLN LAQSKNFHLD PRDLISNINV FVFEVKGSET TFMCEYADET ATIVEFLNRW  120
```

```
ITFSQSIIST LT                                                          132

SEQ ID NO: 41           moltype = AA  length = 132
FEATURE                 Location/Qualifiers
REGION                  1..132
                        note = IL-2 analog 40
source                  1..132
                        mol_type = protein
                        organism = synthetic construct
SEQUENCE: 41
PTSSSTKKTQ LQLEHLLLDL QMILNGINNY KNPKLTAMLT KKFYMPKKAT ELKHLQCLEE      60
ELKPLEEVLN LAQSKNFHLD PRDLISNINV FVFEIKGSET TFMCEYADET ATIVEFLNRW     120
ITFSQSIIST LT                                                          132

SEQ ID NO: 42           moltype = AA  length = 132
FEATURE                 Location/Qualifiers
REGION                  1..132
                        note = IL-2 analog 41
source                  1..132
                        mol_type = protein
                        organism = synthetic construct
SEQUENCE: 42
PTSSSTKKTQ LQLEHLLLDL QMILNGINNY KNPKLTRMLT FKFYMPKKAT ELKHLQCLEE      60
ELKPLEEVLN LAQSKNFHFD PRDVVSNINV FVLELKGSET TFMCEYADET ATIVEFLNRW     120
ITFSQSIIST LT                                                          132

SEQ ID NO: 43           moltype = AA  length = 132
FEATURE                 Location/Qualifiers
REGION                  1..132
                        note = IL-2 analog 42
source                  1..132
                        mol_type = protein
                        organism = synthetic construct
SEQUENCE: 43
PTSSSTKKTQ LQLEHLLLDL QMILNGINNY KNPKLTAMLT KKFYMPKKAT ELKHLQCLEE      60
ELKPLEEVLN LAQSKNFHLE PRDLISNINV FVLELKGSET TFMCEYADET ATIVEFLNRW     120
ITFSQSIIST LT                                                          132

SEQ ID NO: 44           moltype = AA  length = 132
FEATURE                 Location/Qualifiers
REGION                  1..132
                        note = IL-2 analog 43
source                  1..132
                        mol_type = protein
                        organism = synthetic construct
SEQUENCE: 44
PTSSSTKKTQ LQLEHLLLDL QMILNGINNY KNPKLTAMLT KKFYMPKKAT ELKHLQCLEE      60
ELKPLEEVLN LAQSKNFHLD PRDLISNINV LVLELKGSET TFMCEYADET ATIVEFLNRW     120
ITFSQSIIST LT                                                          132

SEQ ID NO: 45           moltype = AA  length = 132
FEATURE                 Location/Qualifiers
REGION                  1..132
                        note = IL-2 analog 44
source                  1..132
                        mol_type = protein
                        organism = synthetic construct
SEQUENCE: 45
PTSSSTKKTQ LQLEHLLLDL QMILNGINNY KNPKLTAMLT KKFYMPKKAT ELKHLQCLEE      60
ELKPLEEVLN LAQSKNFHLD PRVLISNINV FVLELKGSET TFMCEYADET ATIVEFLNRW     120
ITFSQSIIST LT                                                          132

SEQ ID NO: 46           moltype = AA  length = 132
FEATURE                 Location/Qualifiers
REGION                  1..132
                        note = IL-2 analog 45
source                  1..132
                        mol_type = protein
                        organism = synthetic construct
SEQUENCE: 46
PTSSSTKKTQ LQLEHLLLDL QMILNGINNY KNPKLTAMLT KKFYMPKKAT ELKHLQCLEE      60
ELKPLEEVLN LAQSKNFHLD PRFLISNINV FVLELKGSET TFMCEYADET ATIVEFLNRW     120
ITFSQSIIST LT                                                          132

SEQ ID NO: 47           moltype = AA  length = 132
FEATURE                 Location/Qualifiers
REGION                  1..132
                        note = IL-2 analog 46
source                  1..132
```

```
                        mol_type = protein
                        organism = synthetic construct
SEQUENCE: 47
PTSSSTKKTQ LQLEHLLLVL QMILNGINNY KNPKLTAMLT KKFYMPKKAT ELKHLQCLEE      60
ELKPLEEVLN LAQSKNFHLD PRDLISNINV FVLELKGSET TFMCEYADET ATIVEFLNRW     120
ITFSQSIIST LT                                                        132

SEQ ID NO: 48           moltype = AA  length = 132
FEATURE                 Location/Qualifiers
REGION                  1..132
                        note = IL-2 analog 47
source                  1..132
                        mol_type = protein
                        organism = synthetic construct
SEQUENCE: 48
PTSSSTKKTQ LQLEHLLLFL QMILNGINNY KNPKLTAMLT KKFYMPKKAT ELKHLQCLEE      60
ELKPLEEVLN LAQSKNFHLD PRDLISNINV FVLELKGSET TFMCEYADET ATIVEFLNRW     120
ITFSQSIIST LT                                                        132

SEQ ID NO: 49           moltype = AA  length = 132
FEATURE                 Location/Qualifiers
REGION                  1..132
                        note = IL-2 analog 48
source                  1..132
                        mol_type = protein
                        organism = synthetic construct
SEQUENCE: 49
PTSSSTKKTQ LQLEHLLLDL QMILNGINNY KNPKLTAMLT KKFYMPKKAT ELKHLQCLEE      60
ELKPLEEVLN LAQSKNFHLD PRDLISVINV FVLELKGSET TFMCEYADET ATIVEFLNRW     120
ITFSQSIIST LT                                                        132

SEQ ID NO: 50           moltype = AA  length = 132
FEATURE                 Location/Qualifiers
REGION                  1..132
                        note = IL-2 analog 49
source                  1..132
                        mol_type = protein
                        organism = synthetic construct
SEQUENCE: 50
PTSSSTKKTQ LQLEHLLLDL QMILNGINNY KNPKLTAMLT KKFYMPKKAT ELKHLQCLEE      60
ELKPLEEVLN LAQSKNFHLD PRDLISFINV FVLELKGSET TFMCEYADET ATIVEFLNRW     120
ITFSQSIIST LT                                                        132

SEQ ID NO: 51           moltype = AA  length = 132
FEATURE                 Location/Qualifiers
REGION                  1..132
                        note = IL-2 analog 50
source                  1..132
                        mol_type = protein
                        organism = synthetic construct
SEQUENCE: 51
PTSSSTKKTQ LQLEHLLLDL QMILNGINNY KNPKLTRMLT KKFYMPKKAT ELKHLQCLEE      60
ELKPLEEVLN LAQSKNFHFD PRDVVSNINV FVLELKGSET TFMCEYADET ATIVEFLNRW     120
ITFSQSIIST LT                                                        132

SEQ ID NO: 52           moltype = AA  length = 132
FEATURE                 Location/Qualifiers
REGION                  1..132
                        note = IL-2 analog 51
source                  1..132
                        mol_type = protein
                        organism = synthetic construct
SEQUENCE: 52
PTSSSTKKTQ LQLEHLLLDL QMILNGINNY KNPKLTRMLT FKFYMPKKAT ELKHLQCLEQ      60
ELKPLEEVLN LAQSKNFHLD PRDLISNINV FVLELKGSET TFMCEYADET ATIVEFLNRW     120
ITFSQSIIST LT                                                        132

SEQ ID NO: 53           moltype = AA  length = 132
FEATURE                 Location/Qualifiers
REGION                  1..132
                        note = IL-2 analog 52
source                  1..132
                        mol_type = protein
                        organism = synthetic construct
SEQUENCE: 53
PTSSSTKKTQ LQLEHLLLDL QMILNGINNY KNPKLTAMLT KKFYMPKKAT ELKHLQCLEE      60
ELKPLEEVLN LAQSKNFHFD PRDLISNINV FVLELKGSET TFMCEYADET ATIVEFLNRW     120
ITFSQSIIST LT                                                        132
```

| | | |
|---|---|---|
| SEQ ID NO: 54 | moltype = AA   length = 132 | |
| FEATURE | Location/Qualifiers | |
| REGION | 1..132 | |
| | note = IL-2 analog 53 | |
| source | 1..132 | |
| | mol_type = protein | |
| | organism = synthetic construct | |

SEQUENCE: 54
PTSSSTKKTQ LQLEHLLLDL QMILNGINNY KNPKLTAMLT KKFYMPKKAT ELKHLQCLEE    60
ELKPLEEVLN LAQSKNFHFD PRELISNINV FVLELKGSET TFMCEYADET ATIVEFLNRW   120
ITFSQSIIST LT                                                      132

| | | |
|---|---|---|
| SEQ ID NO: 55 | moltype = AA   length = 132 | |
| FEATURE | Location/Qualifiers | |
| REGION | 1..132 | |
| | note = IL-2 analog 54 | |
| source | 1..132 | |
| | mol_type = protein | |
| | organism = synthetic construct | |

SEQUENCE: 55
PTSSSTKKTQ LQLEHLLLDL QMILNGINNY KNPKLTAMLT KKFYMPKKAT ELKHLQCLEE    60
ELKPLEEVLN LAHSKNFHLD PRDLISNINV FVLELKGSET TFMCEYADET ATIVEFLNRW   120
ITFSQSIIST LT                                                      132

| | | |
|---|---|---|
| SEQ ID NO: 56 | moltype = AA   length = 132 | |
| FEATURE | Location/Qualifiers | |
| REGION | 1..132 | |
| | note = IL-2 analog 55 | |
| source | 1..132 | |
| | mol_type = protein | |
| | organism = synthetic construct | |

SEQUENCE: 56
PTSSSTKKTQ LQLEHLLLDL QMILNGINNY KNPKLTAMLT KKFYMPKKAT ELKHLQCLEE    60
ELKPLEEVLN LAHSKNFHFD PRDLISNINV FVLELKGSET TFMCEYADET ATIVEFLNRW   120
ITFSQSIIST LT                                                      132

| | | |
|---|---|---|
| SEQ ID NO: 57 | moltype = AA   length = 132 | |
| FEATURE | Location/Qualifiers | |
| REGION | 1..132 | |
| | note = IL-2 analog 56 | |
| source | 1..132 | |
| | mol_type = protein | |
| | organism = synthetic construct | |

SEQUENCE: 57
PTSSSTKKTQ LQLEHLLLDL QMILNGINNY KNPKLTAMLT KKFAMPKKAT ELKHLQCLEE    60
ELKPLEEVLN LAHSKNFHLD PRDLISNINV FVLELKGSET TFMCEYADET ATIVEFLNRW   120
ITFSQSIIST LT                                                      132

| | | |
|---|---|---|
| SEQ ID NO: 58 | moltype = AA   length = 132 | |
| FEATURE | Location/Qualifiers | |
| REGION | 1..132 | |
| | note = IL-2 analog 57 | |
| source | 1..132 | |
| | mol_type = protein | |
| | organism = synthetic construct | |

SEQUENCE: 58
PTSSSTKKTQ LQLEHLLLDL QMILNGINNY KNPKLTAMLT KKFAMPKKAT ELKHLQCLEE    60
ELKPLEEVLN LAHSKNFHFD PRDLISNINV FVLELKGSET TFMCEYADET ATIVEFLNRW   120
ITFSQSIIST LT                                                      132

| | | |
|---|---|---|
| SEQ ID NO: 59 | moltype = AA   length = 132 | |
| FEATURE | Location/Qualifiers | |
| REGION | 1..132 | |
| | note = IL-2 analog 61 | |
| source | 1..132 | |
| | mol_type = protein | |
| | organism = synthetic construct | |

SEQUENCE: 59
PTSSSTKKTQ LQLEHLLLDL QMILNGINNY KNPKLTAMLT KKFYMPKKAT ELKHLQCLEE    60
ELKPLEEVLN LAQSKNFHFD PRDAASNINV FVLELKGSET TFMCEYADET ATIVEFLNRW   120
ITFSQSIIST LT                                                      132

| | | |
|---|---|---|
| SEQ ID NO: 60 | moltype = AA   length = 132 | |
| FEATURE | Location/Qualifiers | |
| REGION | 1..132 | |
| | note = IL-2 analog 59 | |
| source | 1..132 | |
| | mol_type = protein | |
| | organism = synthetic construct | |

```
SEQUENCE: 60
PTSSSTKKTQ LQLEHLLLDL QMILNGINNY KNPKLTAMLT KKFYMPKKAT ELKHLQCLEE    60
ELKPLEEVLN LAQSKNFHFD PRDAASNINV YVLELKGSET TFMCEYADET ATIVEFLNRW   120
ITFSQSIIST LT                                                      132

SEQ ID NO: 61           moltype = AA   length = 132
FEATURE                 Location/Qualifiers
REGION                  1..132
                        note = IL-2 analog 60
source                  1..132
                        mol_type = protein
                        organism = synthetic construct
SEQUENCE: 61
PTSSSTKKTQ LQLEHLLLDL QMILNGINNY KNPKLTAMLT KKFAMPKKAT ELKHLQCLEE    60
ELKPLEEVLN LAQSKNFHYR PRDAASNINV YVLELKGSET TFMCEYADET ATIVEFLNRW   120
ITFSQSIIST LT                                                      132

SEQ ID NO: 62           moltype = AA   length = 132
FEATURE                 Location/Qualifiers
REGION                  1..132
                        note = IL-2 analog 61
source                  1..132
                        mol_type = protein
                        organism = synthetic construct
SEQUENCE: 62
PTSSSTKKTQ LQLEHLLLDL QMILNGINNY KNPKLTAMLT KKFYMPKKAT ELKHLQCLEE    60
ELKPLEEVLN LAQSKNFHYD PRDGVSNINV YVLELKGSET TFMCEYADET ATIVEFLNRW   120
ITFSQSIIST LT                                                      132

SEQ ID NO: 63           moltype = AA   length = 132
FEATURE                 Location/Qualifiers
REGION                  1..132
                        note = IL-2 analog 62
source                  1..132
                        mol_type = protein
                        organism = synthetic construct
SEQUENCE: 63
PTSSSTKKTQ LQLEHLLLDL QMILNGINNY KNPKLTAMLT KKFYMPKKAT ELKHLQCLEE    60
ELKPLEEVLN LAQSKNFHWE PRDGASNINV FVLELKGSET TFMCEYADET ATIVEFLNRW   120
ITFSQSIIST LT                                                      132

SEQ ID NO: 64           moltype = AA   length = 132
FEATURE                 Location/Qualifiers
REGION                  1..132
                        note = IL-2 analog 63
source                  1..132
                        mol_type = protein
                        organism = synthetic construct
SEQUENCE: 64
PTSSSTKKTQ LQLEHLLLDL QMILNGINNY KNPKLTAMLT KKFYMPKKAT ELKHLQCLEE    60
ELKPLEEVLN LAQSKNFHDE PRDTGSNINV YVLELKGSET TFMCEYADET ATIVEFLNRW   120
ITFSQSIIST LT                                                      132

SEQ ID NO: 65           moltype = AA   length = 132
FEATURE                 Location/Qualifiers
REGION                  1..132
                        note = IL-2 analog 64
source                  1..132
                        mol_type = protein
                        organism = synthetic construct
SEQUENCE: 65
PTSSSTKKTQ LQLEHLLLDL QMILNGINNY KNPKLTAMLT KKFYMPKKAT ELKHLQCLEE    60
ELKPLEEVLN LAQSKNFHYN PRDVVSNINV YVLELKGSET TFMCEYADET ATIVEFLNRW   120
ITFSQSIIST LT                                                      132

SEQ ID NO: 66           moltype = AA   length = 132
FEATURE                 Location/Qualifiers
REGION                  1..132
                        note = IL-2 analog 65
source                  1..132
                        mol_type = protein
                        organism = synthetic construct
SEQUENCE: 66
PTSSSTKKTQ LQLEHLLLDL QMILNGINNY KNPKLTAMLT KKFYMPKKAT ELKHLQCLEE    60
ELKPLEEVLN LAQSKNFHYE PRDVVSNINV FVLELKGSET TFMCEYADET ATIVEFLNRW   120
ITFSQSIIST LT                                                      132

SEQ ID NO: 67           moltype = AA   length = 132
FEATURE                 Location/Qualifiers
```

```
REGION                  1..132
                        note = IL-2 analog 66
source                  1..132
                        mol_type = protein
                        organism = synthetic construct
SEQUENCE: 67
PTSSSTKKTQ LQLEHLLLDL QMILNGINNY KNPKLTAMLT KKFYMPKKAT ELKHLQCLEE    60
ELKPLEEVLN LAQSKNFHFE PRDFVSNINV FVLELKGSET TFMCEYADET ATIVEFLNRW   120
ITFSQSIIST LT                                                      132

SEQ ID NO: 68           moltype = AA   length = 132
FEATURE                 Location/Qualifiers
REGION                  1..132
                        note = IL-2 analog 67
source                  1..132
                        mol_type = protein
                        organism = synthetic construct
SEQUENCE: 68
PTSSSTKKTQ LQLEHLLLDL QMILNGINNY KNPKLTAMLT KKFYMPKKAT ELKHLQCLEE    60
ELKPLEEVLN LAQSKNFHYD PRDFVSNINV WVLDLKGSET TFMCEYADET ATIVEFLNRW   120
ITFSQSIIST LT                                                      132

SEQ ID NO: 69           moltype = AA   length = 132
FEATURE                 Location/Qualifiers
REGION                  1..132
                        note = IL-2 analog 68
source                  1..132
                        mol_type = protein
                        organism = synthetic construct
SEQUENCE: 69
PTSSSTKKTQ LQLEHLLLDL QMILNGINNY KNPKLTAMLT KKFYMPKKAT ELKHLQCLEE    60
ELKPLEEVLN LAQSKNFHFE PRDIVSNINE FVLELKGSET TFMCEYADET ATIVEFLNRW   120
ITFSQSIIST LT                                                      132

SEQ ID NO: 70           moltype = AA   length = 132
FEATURE                 Location/Qualifiers
REGION                  1..132
                        note = IL-2 analog 69
source                  1..132
                        mol_type = protein
                        organism = synthetic construct
SEQUENCE: 70
PTSSSTKKTQ LQLEHLLLDL QMILNGINNY KNPKLTAMLT KKFYMPKKAT ELKHLQCLEE    60
ELKPLEEVLN LAQSKNFHYE PRDFLSNINE WVLDLKGSET TFMCEYADET ATIVEFLNRW   120
ITFSQSIIST LT                                                      132

SEQ ID NO: 71           moltype = AA   length = 132
FEATURE                 Location/Qualifiers
REGION                  1..132
                        note = IL-2 analog 70
source                  1..132
                        mol_type = protein
                        organism = synthetic construct
SEQUENCE: 71
PTSSSTKKTQ LQLEHLLLDL QMILNGINNY KNPKLTAMLT KKFYMPKKAT ELKHLQCLEE    60
ELKPLEEVLN LAQSKNFHYD PRDVVSNINV FVLELKGSET TFMCEYADET ATIVEFLNRW   120
ITFSQSIIST LT                                                      132

SEQ ID NO: 72           moltype = AA   length = 132
FEATURE                 Location/Qualifiers
REGION                  1..132
                        note = IL-2 analog 71
source                  1..132
                        mol_type = protein
                        organism = synthetic construct
SEQUENCE: 72
PTSSSTKKTQ LQLEHLLLDL QMILNGINNY KNPKLTAMLT KKFYMPKKAT ELKHLQCLEE    60
ELKPLEEVLN LAQSKNFHFE PRDVVSNINV FVLELKGSET TFMCEYADET ATIVEFLNRW   120
ITFSQSIIST LT                                                      132

SEQ ID NO: 73           moltype = AA   length = 132
FEATURE                 Location/Qualifiers
REGION                  1..132
                        note = IL-2 analog 72
source                  1..132
                        mol_type = protein
                        organism = synthetic construct
SEQUENCE: 73
PTSSSTKKTQ LQLEHLLLDL QMILNGINNY KNPKLTAMLT KKFYMPKKAT ELKHLQCLEE    60
```

```
ELKPLEEVLN LAQSKNFHFD PRDVGSNINV FVLELKGSET TFMCEYADET ATIVEFLNRW    120
ITFSQSIIST LT                                                       132

SEQ ID NO: 74           moltype = AA  length = 132
        FEATURE                 Location/Qualifiers
        REGION                  1..132
                                note = IL-2 analog 73
        source                  1..132
                                mol_type = protein
                                organism = synthetic construct
SEQUENCE: 74
PTSSSTKKTQ LQLEHLLLDL QMILNGINNY KNPKLTAMLT KKFYMPKKAT ELKHLQCLEE    60
ELKPLEEVLN LAQSKNFHFD PRDWVSNINV FVLELKGSET TFMCEYADET ATIVEFLNRW    120
ITFSQSIIST LT                                                       132

SEQ ID NO: 75           moltype = AA  length = 132
        FEATURE                 Location/Qualifiers
        REGION                  1..132
                                note = IL-2 analog 74
        source                  1..132
                                mol_type = protein
                                organism = synthetic construct
SEQUENCE: 75
PTSSSTKKTQ LQLEHLLLDL QMILNGINNY KNPKLTDMLT KKFYMPKKAT ELKHLQCLEE    60
ELKPLEEVLN LAQSKNFHYD PRDVVSNINV FVLELKGSET TFMCEYADET ATIVEFLNRW    120
ITFSQSIIST LT                                                       132

SEQ ID NO: 76           moltype = AA  length = 132
        FEATURE                 Location/Qualifiers
        REGION                  1..132
                                note = IL-2 analog 75
        source                  1..132
                                mol_type = protein
                                organism = synthetic construct
SEQUENCE: 76
PTSSSTKKTQ LQLEHLLLDL QMILNGINNY KNPKLTAMLT KKFAMPKKAT ELKHLQCLEE    60
ELKPLEEVLN LAQSKNFHFE PRDVVSNINV FVLELKGSET TFMCEYADET ATIVEFLNRW    120
ITFSQSIIST LT                                                       132

SEQ ID NO: 77           moltype = AA  length = 132
        FEATURE                 Location/Qualifiers
        REGION                  1..132
                                note = IL-2 analog 76
        source                  1..132
                                mol_type = protein
                                organism = synthetic construct
SEQUENCE: 77
PTSSSTKKTQ LQLEHLLLDL QMILNGINNY KNPKLTAMLT KQFYMPKKAT ELKHLQCLER    60
ELKPLEEVLN LAQSKNFHFD PRDVGSNINV FVLELKGSET TFMCEYADET ATIVEFLNRW    120
ITFSQSIIST LT                                                       132

SEQ ID NO: 78           moltype = AA  length = 132
        FEATURE                 Location/Qualifiers
        REGION                  1..132
                                note = IL-2 analog 77
        source                  1..132
                                mol_type = protein
                                organism = synthetic construct
SEQUENCE: 78
PTSSSTKKTQ LQLEHLLLDL QMILNGINNY KNPKLTAMLT KEFYMPKKAT ELKHLQCLER    60
ELKPLEEVLN LAQSKNFHFD PRDWVSNINV FVLELKGSET TFMCEYADET ATIVEFLNRW    120
ITFSQSIIST LT                                                       132

SEQ ID NO: 79           moltype = AA  length = 132
        FEATURE                 Location/Qualifiers
        REGION                  1..132
                                note = IL-2 analog 78
        source                  1..132
                                mol_type = protein
                                organism = synthetic construct
SEQUENCE: 79
PTSSSTKKTQ LQLEHLLLDL QMILNGINNY KNPELTAMLT KKFYMPKKAT ELKHLQCLEE    60
ELKPLEEVLN LAQSKNFHFE PRDVVSNINV FVLELKGSET TFMCEYADET ATIVEFLNRW    120
ITFSQSIIST LT                                                       132

SEQ ID NO: 80           moltype = AA  length = 132
        FEATURE                 Location/Qualifiers
        REGION                  1..132
                                note = IL-2 analog 79
```

```
source                  1..132
                        mol_type = protein
                        organism = synthetic construct
SEQUENCE: 80
PTSSSTKKTQ LQLEHLLLDL QMILNGINNY KNPELTAMLT KKFYMPKKAT ELKHLQCLEE    60
ELKPLEEVLN LAHSKNFHFE PRDVVSNINV FVLELKGSET TFMCEYADET ATIVEFLNRW   120
ITFSQSIIST LT                                                      132

SEQ ID NO: 81           moltype = AA  length = 132
FEATURE                 Location/Qualifiers
REGION                  1..132
                        note = IL-2 analog 80
source                  1..132
                        mol_type = protein
                        organism = synthetic construct
SEQUENCE: 81
PTSSSTKKTQ LQLEHLLLDL QMILNGINNY KNPELTAMLT KKYMPKKAT ELKHLQCLEE     60
ELKPLEEVLN LAHSKNFHFE GRDVVSNINV FVLELKGSET TFMCEYADET ATIVEFLNRW   120
ITFSQSIIST LT                                                      132

SEQ ID NO: 82           moltype = AA  length = 132
FEATURE                 Location/Qualifiers
REGION                  1..132
                        note = IL-2 analog 81
source                  1..132
                        mol_type = protein
                        organism = synthetic construct
SEQUENCE: 82
PTSSSTKKTQ LQLEHLLLDL QMILNGINNY KNPELTAMLT KKFYMPKKAT ELKHLQCLEE    60
ELKPLEEVLN LAHSKNFHFE VRDVVSNINV FVLELKGSET TFMCEYADET ATIVEFLNRW   120
ITFSQSIIST LT                                                      132

SEQ ID NO: 83           moltype = AA  length = 132
FEATURE                 Location/Qualifiers
REGION                  1..132
                        note = IL-2 analog 82
source                  1..132
                        mol_type = protein
                        organism = synthetic construct
SEQUENCE: 83
PTSSSTKKTQ LQLEHLRLDL EMILNGINNY KNPKLTRMLT FKFYMPKKAT ELKHLQCLEE    60
ELKPLEEVLN LAQSKNFHFD PRDEVSNINV FVLELKGSET TFMCEYADET ATIVEFLNRW   120
ITFSQSIIST LT                                                      132

SEQ ID NO: 84           moltype = AA  length = 132
FEATURE                 Location/Qualifiers
REGION                  1..132
                        note = IL-2 analog 83
source                  1..132
                        mol_type = protein
                        organism = synthetic construct
SEQUENCE: 84
PTSSSTKKTQ LQLEHLRRDL EMILNGINNY KNPKLTRMLT FKFYMPKKAT ELKHLQCLEE    60
ELKPLEEVLN LAQSKNFHFD PRDEVSNINV FVLELKGSET TFMCEYADET ATIVEFLNRW   120
ITFSQSIIST LT                                                      132

SEQ ID NO: 85           moltype = AA  length = 132
FEATURE                 Location/Qualifiers
REGION                  1..132
                        note = IL-2 analog 84
source                  1..132
                        mol_type = protein
                        organism = synthetic construct
SEQUENCE: 85
PTSSSTKKTQ LQLEHLRLDL EMILNGINNY KNPKLTRMLT FKFYMPKKAT ELKHLQCLEE    60
ELKPLEEVLN LAQSKNFHVD PRDEVSNINV FVLELKGSET TFMCEYADET ATIVEFLNRW   120
ITFSQSIIST LT                                                      132

SEQ ID NO: 86           moltype = AA  length = 132
FEATURE                 Location/Qualifiers
REGION                  1..132
                        note = IL-2 analog 85
source                  1..132
                        mol_type = protein
                        organism = synthetic construct
SEQUENCE: 86
PTSSSTKKTQ LQLEHLLLDL QMILNGINNY KNPKLTRMLT FKFYMPKKAT ELKHLQCLEE    60
ELKPLEEVLN LAQSKNFHFE PRDVVSNINV FVLELKGSET TFMCEYADET ATIVEFLNRW   120
ITFSQSIIST LT                                                      132
```

```
SEQ ID NO: 87          moltype = AA  length = 132
FEATURE                Location/Qualifiers
REGION                 1..132
                       note = IL-2 analog 86
source                 1..132
                       mol_type = protein
                       organism = synthetic construct
SEQUENCE: 87
PTSSSTKKTQ LQLEHLRLDL EMILNGINNY KNPKLTRMLT FKFYMPKKAT ELKHLQCLEE     60
ELKPLEEVLN LAQSKNFHFE PRDVVSNINV FVLELKGSET TFMCEYADET ATIVEFLNRW    120
ITFSQSIIST LT                                                        132

SEQ ID NO: 88          moltype = AA  length = 132
FEATURE                Location/Qualifiers
REGION                 1..132
                       note = IL-2 analog 87
source                 1..132
                       mol_type = protein
                       organism = synthetic construct
SEQUENCE: 88
PTSSSTKKTQ LQLEHLRRDL EMILNGINNY KNPKLTRMLT FKFYMPKKAT ELKHLQCLEE     60
ELKPLEEVLN LAQSKNFHFE PRDVVSNINV FVLELKGSET TFMCEYADET ATIVEFLNRW    120
ITFSQSIIST LT                                                        132

SEQ ID NO: 89          moltype = AA  length = 132
FEATURE                Location/Qualifiers
REGION                 1..132
                       note = IL-2 analog 88
source                 1..132
                       mol_type = protein
                       organism = synthetic construct
SEQUENCE: 89
PTSSSTKKTQ LQLEHLLLDL QMILNGINNY KNPKLTRMLT FKFYMPKKAT ELKHLQCLED     60
ELKPLEEVLN LAQSKNFHFE PRDVVSNINV FVLELKGSET TFMCEYADET ATIVEFLNRW    120
ITFSQSIIST LT                                                        132

SEQ ID NO: 90          moltype = AA  length = 132
FEATURE                Location/Qualifiers
REGION                 1..132
                       note = IL-2 analog 89
source                 1..132
                       mol_type = protein
                       organism = synthetic construct
SEQUENCE: 90
PTSSSTKKTQ LQLEHLLLDL QMILNGINNY KNPKLTAMLT FKFYMPKKAT ELKHLQCLEE     60
ELKPLEQVLN LAQSKNFHFE PRDVVSNINV FVLELKGSET TFMCEYADET ATIVEFLNRW    120
ITFSQSIIST LT                                                        132

SEQ ID NO: 91          moltype = AA  length = 132
FEATURE                Location/Qualifiers
REGION                 1..132
                       note = IL-2 analog 90
source                 1..132
                       mol_type = protein
                       organism = synthetic construct
SEQUENCE: 91
PTSSSTKKTQ LQLEHLLLDL QMILNGINNY KNPKLTRMLT WKFYMPKKAT ELKHLQCLEE     60
ELKPLEEVLN LAQSKNFHFE PRDVVSNINV FVLELKGSET TFMCEYADET ATIVEFLNRW    120
ITFSQSIIST LT                                                        132

SEQ ID NO: 92          moltype = AA  length = 132
FEATURE                Location/Qualifiers
REGION                 1..132
                       note = IL-2 analog 91
source                 1..132
                       mol_type = protein
                       organism = synthetic construct
SEQUENCE: 92
PTSSSTKKTQ LQLEHLLLDL QMILNGINNY KNPKLTRMLT FKFYMPKKAT ELKHLQCLEQ     60
ELKPLEEVLN LAQSKNFHFE PRDVVSNINV FVLELKGSET TFMCEYADET ATIVEFLNRW    120
ITFSQSIIST LT                                                        132

SEQ ID NO: 93          moltype = AA  length = 132
FEATURE                Location/Qualifiers
REGION                 1..132
                       note = IL-2 analog 92
source                 1..132
                       mol_type = protein
```

```
                        organism = synthetic construct
SEQUENCE: 93
PTSSSTKKTQ LQLEHLLLDL QMILNGINNY KNPKLTRMLT FKFYMPKKAT ELKHLQCLEE    60
ELKPLEEVLN LAQSKNFHFE PRDVVSNINT FVLELKGSET TFMCEYADET ATIVEFLNRW   120
ITFSQSIIST LT                                                       132

SEQ ID NO: 94           moltype = AA  length = 132
FEATURE                 Location/Qualifiers
REGION                  1..132
                        note = IL-2 analog 93
source                  1..132
                        mol_type = protein
                        organism = synthetic construct
SEQUENCE: 94
PTSSSTKKTQ LQLEHLLLDL QMILNGINNY KNPKLTRMLT FKFYMPKKAT ELKHLQCLEE    60
ELKPLEEVLN LAQSKNFHFE PREVVSNINT FVLELKGSET TFMCEYADET ATIVEFLNRW   120
ITFSQSIIST LT                                                       132

SEQ ID NO: 95           moltype = AA  length = 132
FEATURE                 Location/Qualifiers
REGION                  1..132
                        note = IL-2 analog 94
source                  1..132
                        mol_type = protein
                        organism = synthetic construct
SEQUENCE: 95
PTSSSTKKTQ LQLEHLLLDL QMILNGINNY KNPKLTRMLT FKFYMPKKAT ELKHLQCLEE    60
ELKPLEEVLN LAQSKNFHFE PRDVVSNINV FVFEFKGSET TFMCEYADET ATIVEFLNRW   120
ITFSQSIIST LT                                                       132

SEQ ID NO: 96           moltype = AA  length = 132
FEATURE                 Location/Qualifiers
REGION                  1..132
                        note = IL-2 analog 95
source                  1..132
                        mol_type = protein
                        organism = synthetic construct
SEQUENCE: 96
PTSSSTKKTQ LQLEHLLLDL QMILNGINNY KNPKLTRMLT FKFYMPKKAT ELKHLQCLEE    60
ELKPLEEGLN LAQSKNFHFE PRDVVSNINV FVLELKGSET TFMCEYADET ATIVEFLNRW   120
ITFSQSIIST LT                                                       132

SEQ ID NO: 97           moltype = AA  length = 132
FEATURE                 Location/Qualifiers
REGION                  1..132
                        note = IL-2 analog 96
source                  1..132
                        mol_type = protein
                        organism = synthetic construct
SEQUENCE: 97
PTSSSTKKTQ LQLEHLLLDL QMILNGINNY KNPKLTRMLT FKFYMPKKAT ELKHLQCLEE    60
ELKPLEEGLN LAASKNFHFE PRDVVSNINV FVLELKGSET TFMCEYADET ATIVEFLNRW   120
ITFSQSIIST LT                                                       132

SEQ ID NO: 98           moltype = AA  length = 132
FEATURE                 Location/Qualifiers
REGION                  1..132
                        note = IL-2 analog 97
source                  1..132
                        mol_type = protein
                        organism = synthetic construct
SEQUENCE: 98
PTSSSTKKTQ LQLEHLLLDL QMILNGINNY KNPKLTAMLT FKFYMPKKAT ELKHLQCLEE    60
ELKPLEEVLN LAQSKNFHFD PRDLISNINV FVLELKGSET TFMCEYADET ATIVEFLNRW   120
ITFSQSIIST LT                                                       132

SEQ ID NO: 99           moltype = AA  length = 132
FEATURE                 Location/Qualifiers
REGION                  1..132
                        note = IL-2 analog 98
source                  1..132
                        mol_type = protein
                        organism = synthetic construct
SEQUENCE: 99
PTSSSTKKTQ LQLEHLLLDL QMILNGINNY KNPKLTAMLT FKFYMPKKAT ELKHLQCLEE    60
ELKPLEEVLN LAQSKNFHFE PRDVISNINV FVLELKGSET TFMCEYADET ATIVEFLNRW   120
ITFSQSIIST LT                                                       132

SEQ ID NO: 100          moltype = AA  length = 132
```

```
FEATURE                 Location/Qualifiers
REGION                  1..132
                        note = IL-2 analog 99
source                  1..132
                        mol_type = protein
                        organism = synthetic construct
SEQUENCE: 100
PTSSSTKKTQ LQLEHLLLDL QMILNGINNY KNPKLTAMLT FKFYMPKKAT ELKHLQCLEE    60
ELKPLEEVLN LAQSKNFHFE PRDLVSNINV FVLELKGSET TFMCEYADET ATIVEFLNRW   120
ITFSQSIIST LT                                                       132

SEQ ID NO: 101          moltype = AA  length = 132
FEATURE                 Location/Qualifiers
REGION                  1..132
                        note = IL-2 analog 100
source                  1..132
                        mol_type = protein
                        organism = synthetic construct
SEQUENCE: 101
PTSSSTKKTQ LQLEHLLLDL QMILNGINNY KNPKLTRMLT FKFYMPKKAT ELKHLQCLEE    60
ELKPLEEVLN LAQSKNFHFE PRDYVSNINV FVLELKGSET TFMCEYADET ATIVEFLNRW   120
ITFSQSIIST LT                                                       132

SEQ ID NO: 102          moltype = AA  length = 132
FEATURE                 Location/Qualifiers
REGION                  1..132
                        note = IL-2 analog 101
source                  1..132
                        mol_type = protein
                        organism = synthetic construct
SEQUENCE: 102
PTSSSTKKTQ LQLEHLLLDL QMILNGINNY KNPKLTRMLT FKFYMPKKAT ELKHLQCLEE    60
ELKPLEEVLN LAQSKNFHFE PRDLASNINV FVLELKGSET TFMCEYADET ATIVEFLNRW   120
ITFSQSIIST LT                                                       132

SEQ ID NO: 103          moltype = AA  length = 132
FEATURE                 Location/Qualifiers
REGION                  1..132
                        note = IL-2 analog 102
source                  1..132
                        mol_type = protein
                        organism = synthetic construct
SEQUENCE: 103
PTSSSTKKTQ LQLEHLLLDL QMILNGINNY KNPKLTRMLT FKFYMPKKAT ELKHLQCLEE    60
ELKPLEEVLN LAQSKNFHFE PRDVVSNINV IVLELKGSET TFMCEYADET ATIVEFLNRW   120
ITFSQSIIST LT                                                       132

SEQ ID NO: 104          moltype = AA  length = 132
FEATURE                 Location/Qualifiers
REGION                  1..132
                        note = IL-2 analog 103
source                  1..132
                        mol_type = protein
                        organism = synthetic construct
SEQUENCE: 104
PTSSSTKKTQ LQLEHLRLDL EMILNGINNY KNPKLTAMLT FKFYMPKKAT ELKHLQCLEE    60
ELKPLEEVLN LAQSKNFHFE PRDVVSNINV FVLELKGSET TFMCEYADET ATIVEFLNRW   120
ITFSQSIIST LT                                                       132

SEQ ID NO: 105          moltype = AA  length = 132
FEATURE                 Location/Qualifiers
REGION                  1..132
                        note = IL-2 analog 104
source                  1..132
                        mol_type = protein
                        organism = synthetic construct
SEQUENCE: 105
PTSSSTKKTQ LQLEHLRLDL EMILNGINNY KNPKLTRMLT FKFYMPKKAT ELKHLQCLED    60
ELKPLEEVLN LAQSKNFHFE PRDVVSNINV FVLELKGSET TFMCEYADET ATIVEFLNRW   120
ITFSQSIIST LT                                                       132

SEQ ID NO: 106          moltype = AA  length = 132
FEATURE                 Location/Qualifiers
REGION                  1..132
                        note = IL-2 analog 105
source                  1..132
                        mol_type = protein
                        organism = synthetic construct
SEQUENCE: 106
```

```
PTSSSTKKTQ LQLEHLRLDL EMILNGINNY KNPKLTRMLT FKFYMPKKAT ELKHLQCLEE    60
ELKPLEDVLN LAQSKNFHFE PRDVVSNINV FVLELKGSET TFMCEYADET ATIVEFLNRW   120
ITFSQSIIST LT                                                       132

SEQ ID NO: 107          moltype = DNA   length = 399
FEATURE                 Location/Qualifiers
misc_feature            1..399
                        note = IL-2 analog 1
source                  1..399
                        mol_type = other DNA
                        organism = synthetic construct
SEQUENCE: 107
cctacttcaa gttctacaaa gaaaacacag ctacaactgg agcatttact gctggattta    60
cagatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact aatcagcaa tatcaacgta atagttctgg aactaaaggg atctgaaaca    300
acattcatgt gtgaatatgc tgatgagaca gcaaccattg tagaatttct gaacagatgg   360
attacccttta gtcaaagcat catctcaaca ctgacttga                         399

SEQ ID NO: 108          moltype = DNA   length = 399
FEATURE                 Location/Qualifiers
misc_feature            1..399
                        note = IL-2 analog 2
source                  1..399
                        mol_type = other DNA
                        organism = synthetic construct
SEQUENCE: 108
cctacttcaa gttctacaaa gaaaacacag ctacaactgg agcatttact gctggattta    60
cagatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact aatctgcaa tatcaacgta atagttctgg aactaaaggg atctgaaaca    300
acattcatgt gtgaatatgc tgatgagaca gcaaccattg tagaatttct gaacagatgg   360
attacccttta gtcaaagcat catctcaaca ctgacttga                         399

SEQ ID NO: 109          moltype = DNA   length = 399
FEATURE                 Location/Qualifiers
misc_feature            1..399
                        note = IL-2 analog 3
source                  1..399
                        mol_type = other DNA
                        organism = synthetic construct
SEQUENCE: 109
cctacttcaa gttctacaaa gaaaacacag ctacaactgg agcatttact gctggattta    60
cagatgattt tgaatggaat taataattac tgtaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact aatcagcaa tatcaacgta atagttctgg aactaaaggg atctgaaaca    300
acattcatgt gtgaatatgc tgatgagaca gcaaccattg tagaatttct gaacagatgg   360
attacccttta gtcaaagcat catctcaaca ctgacttga                         399

SEQ ID NO: 110          moltype = DNA   length = 399
FEATURE                 Location/Qualifiers
misc_feature            1..399
                        note = IL-2 analog 4
source                  1..399
                        mol_type = other DNA
                        organism = synthetic construct
SEQUENCE: 110
cctacttcaa gttctacaaa gaaaacacag ctacaactgg agcatttact gctggattta    60
cagatgattt tgaatggaat taataattac aagaatccct gtctcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact aatcagcaa tatcaacgta atagttctgg aactaaaggg atctgaaaca    300
acattcatgt gtgaatatgc tgatgagaca gcaaccattg tagaatttct gaacagatgg   360
attacccttta gtcaaagcat catctcaaca ctgacttga                         399

SEQ ID NO: 111          moltype = DNA   length = 399
FEATURE                 Location/Qualifiers
misc_feature            1..399
                        note = IL-2 analog 5
source                  1..399
                        mol_type = other DNA
                        organism = synthetic construct
SEQUENCE: 111
cctacttcaa gttctacaaa gaaaacacag ctacaactgg agcatttact gctggattta    60
cagatgattt tgaatggaat taataattac aagaatccca aactcaccag gatgctcaca   120
ttttgttttt acatgcccaa gaaggccaca gaactgaaac atcttcagtg tctagaagaa   180
```

```
gaactcaaac ctctggagga agtgctaaat ttagctcaaa gcaaaaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 112              moltype = DNA   length = 399
FEATURE                     Location/Qualifiers
misc_feature                1..399
                            note = IL-2 analog 6
source                      1..399
                            mol_type = other DNA
                            organism = synthetic construct
SEQUENCE: 112
cctacttcaa gttctacaaa gaaaacacag ctacaactgg agcatttact gctggattta   60
cagatgattt tgaatggaat taataattac aagaatccca aactcaccag gatgctcaca   120
tttaagtttt acatgccctg taaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 113              moltype = DNA   length = 399
FEATURE                     Location/Qualifiers
misc_feature                1..399
                            note = IL-2 analog 7
source                      1..399
                            mol_type = other DNA
                            organism = synthetic construct
SEQUENCE: 113
cctacttcaa gttctacaaa gaaaacacag ctacaactgg agcatttact gctggattta   60
cagatgattt tgaatggaat taataattac aagaatccca aactcaccag gatgctcaca   120
tttaagtttt acatgcccaa gtgtgccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 114              moltype = DNA   length = 399
FEATURE                     Location/Qualifiers
misc_feature                1..399
                            note = IL-2 analog 8
source                      1..399
                            mol_type = other DNA
                            organism = synthetic construct
SEQUENCE: 114
cctacttcaa gttctacaaa gaaaacacag ctacaactgg agcatttact gctggattta   60
cagatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gctgtaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 115              moltype = DNA   length = 399
FEATURE                     Location/Qualifiers
misc_feature                1..399
                            note = IL-2 analog 9
source                      1..399
                            mol_type = other DNA
                            organism = synthetic construct
SEQUENCE: 115
cctacttcaa gttctacaaa gaaaacacag ctacaactgg agcatttact gctggattta   60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 116              moltype = DNA   length = 399
FEATURE                     Location/Qualifiers
misc_feature                1..399
                            note = IL-2 analog 10
source                      1..399
                            mol_type = other DNA
                            organism = synthetic construct
SEQUENCE: 116
cctacttcaa gttctacaaa gaaaacacag ctacaactgg agcatttact gctggattta   60
cagatgattt tgaatggaat taataattac aagaatccca aactcaccag gatgctcaca   120
```

```
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399
```

| SEQ ID NO: 117 | moltype = DNA  length = 399 |
|---|---|
| FEATURE | Location/Qualifiers |
| misc_feature | 1..399 |
| | note = IL-2 analog 11 |
| source | 1..399 |
| | mol_type = other DNA |
| | organism = synthetic construct |

```
SEQUENCE: 117
cctacttcaa gttctacaaa gaaaacacag ctacaactgg agcatttact gctggattta    60
cagatgattt tgaatggaat taataattac aagaatccca aactcaccag gatgctcaca    120
gctaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399
```

| SEQ ID NO: 118 | moltype = DNA  length = 399 |
|---|---|
| FEATURE | Location/Qualifiers |
| misc_feature | 1..399 |
| | note = IL-2 analog 12 |
| source | 1..399 |
| | mol_type = other DNA |
| | organism = synthetic construct |

```
SEQUENCE: 118
cctacttcaa gttctacaaa gaaaacacag ctacaactgg agcatttact gctggattta    60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399
```

| SEQ ID NO: 119 | moltype = DNA  length = 399 |
|---|---|
| FEATURE | Location/Qualifiers |
| misc_feature | 1..399 |
| | note = IL-2 analog 13 |
| source | 1..399 |
| | mol_type = other DNA |
| | organism = synthetic construct |

```
SEQUENCE: 119
cctacttcaa gttctacaaa gaaaacacag ctacaactgg agcatttact gctggattta    60
cagatgattt tgaatggaat taataattac aagaatccca aactcaccgc gatgctcaca    120
gctaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399
```

| SEQ ID NO: 120 | moltype = DNA  length = 399 |
|---|---|
| FEATURE | Location/Qualifiers |
| misc_feature | 1..399 |
| | note = IL-2 analog 14 |
| source | 1..399 |
| | mol_type = other DNA |
| | organism = synthetic construct |

```
SEQUENCE: 120
cctacttcaa gttctacaaa gaaaacacag ctacaactgg agcatttact gtacgattta    60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399
```

| SEQ ID NO: 121 | moltype = DNA  length = 399 |
|---|---|
| FEATURE | Location/Qualifiers |
| misc_feature | 1..399 |
| | note = IL-2 analog 15 |
| source | 1..399 |
| | mol_type = other DNA |
| | organism = synthetic construct |

```
SEQUENCE: 121
cctacttcaa gttctacaaa gaaaacacag ctacaactgg agcatttact gctggattta    60
```

```
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggagt taatcagcaa tatcaacgta atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399

SEQ ID NO: 122            moltype = DNA   length = 399
FEATURE                   Location/Qualifiers
misc_feature              1..399
                          note = IL-2 analog 16
source                    1..399
                          mol_type = other DNA
                          organism = synthetic construct
SEQUENCE: 122
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcca aatcaacgta atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399

SEQ ID NO: 123            moltype = DNA   length = 399
FEATURE                   Location/Qualifiers
misc_feature              1..399
                          note = IL-2 analog 17
source                    1..399
                          mol_type = other DNA
                          organism = synthetic construct
SEQUENCE: 123
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacaca atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399

SEQ ID NO: 124            moltype = DNA   length = 399
FEATURE                   Location/Qualifiers
misc_feature              1..399
                          note = IL-2 analog 18
source                    1..399
                          mol_type = other DNA
                          organism = synthetic construct
SEQUENCE: 124
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaacag    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399

SEQ ID NO: 125            moltype = DNA   length = 399
FEATURE                   Location/Qualifiers
misc_feature              1..399
                          note = IL-2 analog 19
source                    1..399
                          mol_type = other DNA
                          organism = synthetic construct
SEQUENCE: 125
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggact taatcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399

SEQ ID NO: 126            moltype = DNA   length = 399
FEATURE                   Location/Qualifiers
misc_feature              1..399
                          note = IL-2 analog 20
source                    1..399
                          mol_type = other DNA
                          organism = synthetic construct
SEQUENCE: 126
```

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggacg tagtcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 127          moltype = DNA  length = 399
FEATURE                 Location/Qualifiers
misc_feature            1..399
                        note = IL-2 analog 21
source                  1..399
                        mol_type = other DNA
                        organism = synthetic construct
SEQUENCE: 127
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggacg tagtcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 128          moltype = DNA  length = 399
FEATURE                 Location/Qualifiers
misc_feature            1..399
                        note = IL-2 analog 22
source                  1..399
                        mol_type = other DNA
                        organism = synthetic construct
SEQUENCE: 128
cctacttcaa gttctacaaa gaaaacacag gtacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 129          moltype = DNA  length = 399
FEATURE                 Location/Qualifiers
misc_feature            1..399
                        note = IL-2 analog 23
source                  1..399
                        mol_type = other DNA
                        organism = synthetic construct
SEQUENCE: 129
cctacttcaa gttctacaaa gaaaacacag tttcaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 130          moltype = DNA  length = 399
FEATURE                 Location/Qualifiers
misc_feature            1..399
                        note = IL-2 analog 24
source                  1..399
                        mol_type = other DNA
                        organism = synthetic construct
SEQUENCE: 130
cctacttcaa gttctacaaa gaaaacacag ctacaactgg agcatttact ggtggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 131          moltype = DNA  length = 399
FEATURE                 Location/Qualifiers
misc_feature            1..399
                        note = IL-2 analog 25
source                  1..399
                        mol_type = other DNA
                        organism = synthetic construct
```

```
SEQUENCE: 131
cctacttcaa gttctacaaa gaaaacacag ctacaactgg agcatttact gttcgattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attcccttta gtcaaagcat catctcaaca ctgacttga                          399

SEQ ID NO: 132         moltype = DNA   length = 399
FEATURE                Location/Qualifiers
misc_feature           1..399
                       note = IL-2 analog 26
source                 1..399
                       mol_type = other DNA
                       organism = synthetic construct
SEQUENCE: 132
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tttcaacgta atagttctgg aactaaaggg atctgaaaca   300
acattcatgt gtgaatatgc tgatgagaca gcaaccattg tagaatttct gaacagatgg   360
attcccttta gtcaaagcat catctcaaca ctgacttga                          399

SEQ ID NO: 133         moltype = DNA   length = 399
FEATURE                Location/Qualifiers
misc_feature           1..399
                       note = IL-2 analog 27
source                 1..399
                       mol_type = other DNA
                       organism = synthetic construct
SEQUENCE: 133
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacttt atagttctgg aactaaaggg atctgaaaca   300
acattcatgt gtgaatatgc tgatgagaca gcaaccattg tagaatttct gaacagatgg   360
attcccttta gtcaaagcat catctcaaca ctgacttga                          399

SEQ ID NO: 134         moltype = DNA   length = 399
FEATURE                Location/Qualifiers
misc_feature           1..399
                       note = IL-2 analog 28
source                 1..399
                       mol_type = other DNA
                       organism = synthetic construct
SEQUENCE: 134
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttgtgg aactaaaggg atctgaaaca   300
acattcatgt gtgaatatgc tgatgagaca gcaaccattg tagaatttct gaacagatgg   360
attcccttta gtcaaagcat catctcaaca ctgacttga                          399

SEQ ID NO: 135         moltype = DNA   length = 399
FEATURE                Location/Qualifiers
misc_feature           1..399
                       note = IL-2 analog 29
source                 1..399
                       mol_type = other DNA
                       organism = synthetic construct
SEQUENCE: 135
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attcccttta gtcaaagcat catctcaaca ctgacttga                          399

SEQ ID NO: 136         moltype = DNA   length = 399
FEATURE                Location/Qualifiers
misc_feature           1..399
                       note = IL-2 analog 30
source                 1..399
                       mol_type = other DNA
```

-continued

```
                        organism = synthetic construct
SEQUENCE: 136
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 137        moltype = DNA   length = 399
FEATURE               Location/Qualifiers
misc_feature          1..399
                      note = IL-2 analog 31
source                1..399
                      mol_type = other DNA
                      organism = synthetic construct
SEQUENCE: 137
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggagt taatcagcaa tatcaacgta atagttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 138        moltype = DNA   length = 399
FEATURE               Location/Qualifiers
misc_feature          1..399
                      note = IL-2 analog 32
source                1..399
                      mol_type = other DNA
                      organism = synthetic construct
SEQUENCE: 138
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggagt taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 139        moltype = DNA   length = 399
FEATURE               Location/Qualifiers
misc_feature          1..399
                      note = IL-2 analog 33
source                1..399
                      mol_type = other DNA
                      organism = synthetic construct
SEQUENCE: 139
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcactttaga   240
cccagggact taatcagcaa tatcaacgta atagttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 140        moltype = DNA   length = 399
FEATURE               Location/Qualifiers
misc_feature          1..399
                      note = IL-2 analog 34
source                1..399
                      mol_type = other DNA
                      organism = synthetic construct
SEQUENCE: 140
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcactttaga   240
cccagggagt taatcagcaa tatcaacgta atagttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399

SEQ ID NO: 141        moltype = DNA   length = 399
FEATURE               Location/Qualifiers
misc_feature          1..399
                      note = IL-2 analog 35
source                1..399
```

```
                        mol_type = other DNA
                        organism = synthetic construct
SEQUENCE: 141
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttttcg aatttaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 142          moltype = DNA   length = 399
FEATURE                 Location/Qualifiers
misc_feature            1..399
                        note = IL-2 analog 36
source                  1..399
                        mol_type = other DNA
                        organism = synthetic construct
SEQUENCE: 142
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttttcg aagtaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 143          moltype = DNA   length = 399
FEATURE                 Location/Qualifiers
misc_feature            1..399
                        note = IL-2 analog 37
source                  1..399
                        mol_type = other DNA
                        organism = synthetic construct
SEQUENCE: 143
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta ttagttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 144          moltype = DNA   length = 399
FEATURE                 Location/Qualifiers
misc_feature            1..399
                        note = IL-2 analog 38
source                  1..399
                        mol_type = other DNA
                        organism = synthetic construct
SEQUENCE: 144
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta tttgttttcg aatttaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 145          moltype = DNA   length = 399
FEATURE                 Location/Qualifiers
misc_feature            1..399
                        note = IL-2 analog 39
source                  1..399
                        mol_type = other DNA
                        organism = synthetic construct
SEQUENCE: 145
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta tttgttttcg aagtaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 146          moltype = DNA   length = 399
FEATURE                 Location/Qualifiers
misc_feature            1..399
                        note = IL-2 analog 40
```

```
source                         1..399
                               mol_type = other DNA
                               organism = synthetic construct
SEQUENCE: 146
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta tttgttttcg aaattaaggg atctgaaaca   300
acattcatgt gtgaatatgc tgatgagaca gcaaccattg tagaatttct gaacagatgg   360
attaccttta gtcaaagcat catctcaaca ctgacttga                         399

SEQ ID NO: 147                 moltype = DNA  length = 399
FEATURE                        Location/Qualifiers
misc_feature                   1..399
                               note = IL-2 analog 41
source                         1..399
                               mol_type = other DNA
                               organism = synthetic construct
SEQUENCE: 147
cctacttcaa gttctacaaa gaaaacacag ctacaactgg agcatttact gctggattta    60
cagatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggacg tagtcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                         399

SEQ ID NO: 148                 moltype = DNA  length = 399
FEATURE                        Location/Qualifiers
misc_feature                   1..399
                               note = IL-2 analog 42
source                         1..399
                               mol_type = other DNA
                               organism = synthetic construct
SEQUENCE: 148
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagaa   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                         399

SEQ ID NO: 149                 moltype = DNA  length = 399
FEATURE                        Location/Qualifiers
misc_feature                   1..399
                               note = IL-2 analog 43
source                         1..399
                               mol_type = other DNA
                               organism = synthetic construct
SEQUENCE: 149
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta ttagttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                         399

SEQ ID NO: 150                 moltype = DNA  length = 399
FEATURE                        Location/Qualifiers
misc_feature                   1..399
                               note = IL-2 analog 44
source                         1..399
                               mol_type = other DNA
                               organism = synthetic construct
SEQUENCE: 150
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggtct taatcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                         399

SEQ ID NO: 151                 moltype = DNA  length = 399
FEATURE                        Location/Qualifiers
misc_feature                   1..399
```

```
                        note = IL-2 analog 45
source                  1..399
                        mol_type = other DNA
                        organism = synthetic construct
SEQUENCE: 151
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttagac     240
cccaggttct taatcagcaa tatcaacgta tttgttctgg aactaaaggg atctgaaaca     300
acattcatgt gtgaatatgc tgatgagaca gcaaccattg tagaatttct gaacagatgg     360
attacctta gtcaaagcat catctcaaca ctgacttga                             399

SEQ ID NO: 152          moltype = DNA  length = 399
FEATURE                 Location/Qualifiers
misc_feature            1..399
                        note = IL-2 analog 46
source                  1..399
                        mol_type = other DNA
                        organism = synthetic construct
SEQUENCE: 152
cctacttcaa gttctacaaa gaaaacacag ctacaactgg agcatttact gctggtttta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttagac     240
cccagggact taatcagcaa tatcaacgta tttgttctgg aactaaaggg atctgaaaca     300
acattcatgt gtgaatatgc tgatgagaca gcaaccattg tagaatttct gaacagatgg     360
attacctta gtcaaagcat catctcaaca ctgacttga                             399

SEQ ID NO: 153          moltype = DNA  length = 399
FEATURE                 Location/Qualifiers
misc_feature            1..399
                        note = IL-2 analog 47
source                  1..399
                        mol_type = other DNA
                        organism = synthetic construct
SEQUENCE: 153
cctacttcaa gttctacaaa gaaaacacag ctacaactgg agcatttact gctgtttta       60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttagac     240
cccagggact taatcagcaa tatcaacgta tttgttctgg aactaaaggg atctgaaaca     300
acattcatgt gtgaatatgc tgatgagaca gcaaccattg tagaatttct gaacagatgg     360
attacctta gtcaaagcat catctcaaca ctgacttga                             399

SEQ ID NO: 154          moltype = DNA  length = 399
FEATURE                 Location/Qualifiers
misc_feature            1..399
                        note = IL-2 analog 48
source                  1..399
                        mol_type = other DNA
                        organism = synthetic construct
SEQUENCE: 154
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttagac     240
cccagggact taatcagcgt tatcaacgta tttgttctgg aactaaaggg atctgaaaca     300
acattcatgt gtgaatatgc tgatgagaca gcaaccattg tagaatttct gaacagatgg     360
attacctta gtcaaagcat catctcaaca ctgacttga                             399

SEQ ID NO: 155          moltype = DNA  length = 399
FEATURE                 Location/Qualifiers
misc_feature            1..399
                        note = IL-2 analog 49
source                  1..399
                        mol_type = other DNA
                        organism = synthetic construct
SEQUENCE: 155
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttagac     240
cccagggact taatcagctt tatcaacgta tttgttctgg aactaaaggg atctgaaaca     300
acattcatgt gtgaatatgc tgatgagaca gcaaccattg tagaatttct gaacagatgg     360
attacctta gtcaaagcat catctcaaca ctgacttga                             399

SEQ ID NO: 156          moltype = DNA  length = 399
FEATURE                 Location/Qualifiers
```

| | | |
|---|---|---|
| misc_feature | 1..399 | |
| | note = IL-2 analog 50 | |
| source | 1..399 | |
| | mol_type = other DNA | |
| | organism = synthetic construct | |

SEQUENCE: 156
```
cctacttcaa gttctacaaa gaaaacacag ctacaactgg agcatttact gctggattta    60
cagatgattt tgaatggaat taataattac aagaatccca aactcaccag gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggacg tagtcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                          399
```

| | | |
|---|---|---|
| SEQ ID NO: 157 | moltype = DNA    length = 399 | |
| FEATURE | Location/Qualifiers | |
| misc_feature | 1..399 | |
| | note = IL-2 analog 51 | |
| source | 1..399 | |
| | mol_type = other DNA | |
| | organism = synthetic construct | |

SEQUENCE: 157
```
cctacttcaa gttctacaaa gaaaacacag ctacaactgg agcatttact gctggattta    60
cagatgattt tgaatggaat taataattac aagaatccca aactcaccag gatgctcaca   120
tttaagtttt acatgcccaa gaaggccaca gaactgaaac atcttcagtg tctagaacag   180
gaactcaaac ctctggagga agtgctaaat ttagctcaaa gcaaaaactt tcacttagac   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                          399
```

| | | |
|---|---|---|
| SEQ ID NO: 158 | moltype = DNA    length = 399 | |
| FEATURE | Location/Qualifiers | |
| misc_feature | 1..399 | |
| | note = IL-2 analog 52 | |
| source | 1..399 | |
| | mol_type = other DNA | |
| | organism = synthetic construct | |

SEQUENCE: 158
```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                          399
```

| | | |
|---|---|---|
| SEQ ID NO: 159 | moltype = DNA    length = 399 | |
| FEATURE | Location/Qualifiers | |
| misc_feature | 1..399 | |
| | note = IL-2 analog 53 | |
| source | 1..399 | |
| | mol_type = other DNA | |
| | organism = synthetic construct | |

SEQUENCE: 159
```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggagt taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                          399
```

| | | |
|---|---|---|
| SEQ ID NO: 160 | moltype = DNA    length = 399 | |
| FEATURE | Location/Qualifiers | |
| misc_feature | 1..399 | |
| | note = IL-2 analog 54 | |
| source | 1..399 | |
| | mol_type = other DNA | |
| | organism = synthetic construct | |

SEQUENCE: 160
```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                          399
```

| | | |
|---|---|---|
| SEQ ID NO: 161 | moltype = DNA    length = 399 | |

| FEATURE | Location/Qualifiers |
|---|---|
| misc_feature | 1..399 |
| | note = IL-2 analog 55 |
| source | 1..399 |
| | mol_type = other DNA |
| | organism = synthetic construct |

SEQUENCE: 161

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaca gcaaaaactt tcactttgac   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399
```

| SEQ ID NO: 162 | moltype = DNA   length = 399 |
|---|---|
| FEATURE | Location/Qualifiers |
| misc_feature | 1..399 |
| | note = IL-2 analog 56 |
| source | 1..399 |
| | mol_type = other DNA |
| | organism = synthetic construct |

SEQUENCE: 162

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttg ccatgcccaa gaaggccaca gaactgaaac atcttcagtg tctagaagaa   180
gaactcaaac ctctggagga agtgctaaat ttagctcaca gcaaaaactt tcacttagac   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399
```

| SEQ ID NO: 163 | moltype = DNA   length = 399 |
|---|---|
| FEATURE | Location/Qualifiers |
| misc_feature | 1..399 |
| | note = IL-2 analog 57 |
| source | 1..399 |
| | mol_type = other DNA |
| | organism = synthetic construct |

SEQUENCE: 163

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttg ccatgcccaa gaaggccaca gaactgaaac atcttcagtg tctagaagaa   180
gaactcaaac ctctggagga agtgctaaat ttagctcaca gcaaaaactt tcactttgac   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399
```

| SEQ ID NO: 164 | moltype = DNA   length = 399 |
|---|---|
| FEATURE | Location/Qualifiers |
| misc_feature | 1..399 |
| | note = IL-2 analog 58 |
| source | 1..399 |
| | mol_type = other DNA |
| | organism = synthetic construct |

SEQUENCE: 164

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggacg ctgccagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399
```

| SEQ ID NO: 165 | moltype = DNA   length = 399 |
|---|---|
| FEATURE | Location/Qualifiers |
| misc_feature | 1..399 |
| | note = IL-2 analog 59 |
| source | 1..399 |
| | mol_type = other DNA |
| | organism = synthetic construct |

SEQUENCE: 165

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttg ccatgcccaa gaaggccaca gaactgaaac atcttcagtg tctagaagaa   180
gaactcaaac ctctggagga agtgctaaat ttagctcaaa gcaaaaactt tcactttgac   240
cccagggacg ctgccagcaa tatcaacgta tatgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399
```

| SEQ ID NO: 166 | moltype = DNA length = 399 |
| --- | --- |
| FEATURE | Location/Qualifiers |
| misc_feature | 1..399 |
| | note = IL-2 analog 60 |
| source | 1..399 |
| | mol_type = other DNA |
| | organism = synthetic construct |

SEQUENCE: 166

| | | |
| --- | --- | --- |
| cctacttcaa gttctacaaa gaaaacacag ctacaactgg agcatttact gctggattta | 60 |
| cagatgattt tgaatggaat taataattac aagaatccca aactcaccgc gatgctcaca | 120 |
| aagaagtttg ccatgcccaa gaaggccaca gaactgaaac atcttcagtg tctagaagaa | 180 |
| gaactcaaac ctctggagga agtgctaaat ttagctcaaa gcaaaaactt tcactataga | 240 |
| cccagggacg ctgccagcaa tatcaacgta tatgttctgg aactaaaggg atctgaaaca | 300 |
| acattcatgt gtgaatatgc tgatgagaca gcaaccattg tagaatttct gaacagatgg | 360 |
| attacccttta gtcaaagcat catctcaaca ctgacttga | 399 |

| SEQ ID NO: 167 | moltype = DNA length = 399 |
| --- | --- |
| FEATURE | Location/Qualifiers |
| misc_feature | 1..399 |
| | note = IL-2 analog 61 |
| source | 1..399 |
| | mol_type = other DNA |
| | organism = synthetic construct |

SEQUENCE: 167

| | | |
| --- | --- | --- |
| cctacttcaa gttctacaaa gaaaacacag ctacaactgg agcatttact gctggattta | 60 |
| cagatgattt tgaatggaat taataattac aagaatccca aactcaccgc gatgctcaca | 120 |
| aagaagttttt acatgcccaa gaaggccaca gaactgaaac atcttcagtg tctagaagaa | 180 |
| gaactcaaac ctctggagga agtgctaaat ttagctcaaa gcaaaaactt tcactatgac | 240 |
| cccagggacg tgttagcaa tatcaacgta tatgttctgg aactaaaggg atctgaaaca | 300 |
| acattcatgt gtgaatatgc tgatgagaca gcaaccattg tagaatttct gaacagatgg | 360 |
| attaccttta gtcaaagcat catctcaaca ctgacttga | 399 |

| SEQ ID NO: 168 | moltype = DNA length = 399 |
| --- | --- |
| FEATURE | Location/Qualifiers |
| misc_feature | 1..399 |
| | note = IL-2 analog 62 |
| source | 1..399 |
| | mol_type = other DNA |
| | organism = synthetic construct |

SEQUENCE: 168

| | | |
| --- | --- | --- |
| cctacttcaa gttctacaaa gaaaacacag ctacaactgg agcatttact gctggattta | 60 |
| cagatgattt tgaatggaat taataattac aagaatccca aactcaccgc gatgctcaca | 120 |
| aagaagttttt acatgcccaa gaaggccaca gaactgaaac atcttcagtg tctagaagaa | 180 |
| gaactcaaac ctctggagga agtgctaaat ttagctcaaa gcaaaaactt tcactgggaa | 240 |
| cccagggacg gagccagcaa tatcaacgta tttgttctgg aactaaaggg atctgaaaca | 300 |
| acattcatgt gtgaatatgc tgatgagaca gcaaccattg tagaatttct gaacagatgg | 360 |
| attaccttta gtcaaagcat catctcaaca ctgacttga | 399 |

| SEQ ID NO: 169 | moltype = DNA length = 399 |
| --- | --- |
| FEATURE | Location/Qualifiers |
| misc_feature | 1..399 |
| | note = IL-2 analog 63 |
| source | 1..399 |
| | mol_type = other DNA |
| | organism = synthetic construct |

SEQUENCE: 169

| | | |
| --- | --- | --- |
| cctacttcaa gttctacaaa gaaaacacag ctacaactgg agcatttact gctggattta | 60 |
| cagatgattt tgaatggaat taataattac aagaatccca aactcaccgc gatgctcaca | 120 |
| aagaagttttt acatgcccaa gaaggccaca gaactgaaac atcttcagtg tctagaagaa | 180 |
| gaactcaaac ctctggagga agtgctaaat ttagctcaaa gcaaaaactt tcacgacgaa | 240 |
| cccagggaca caggcagcaa tatcaacgta tttgttctgg aactaaaggg atctgaaaca | 300 |
| acattcatgt gtgaatatgc tgatgagaca gcaaccattg tagaatttct gaacagatgg | 360 |
| attaccttta gtcaaagcat catctcaaca ctgacttga | 399 |

| SEQ ID NO: 170 | moltype = DNA length = 399 |
| --- | --- |
| FEATURE | Location/Qualifiers |
| misc_feature | 1..399 |
| | note = IL-2 analog 64 |
| source | 1..399 |
| | mol_type = other DNA |
| | organism = synthetic construct |

SEQUENCE: 170

| | | |
| --- | --- | --- |
| cctacttcaa gttctacaaa gaaaacacag ctacaactgg agcatttact gctggattta | 60 |
| cagatgattt tgaatggaat taataattac aagaatccca aactcaccgc gatgctcaca | 120 |
| aagaagttttt acatgcccaa gaaggccaca gaactgaaac atcttcagtg tctagaagaa | 180 |
| gaactcaaac ctctggagga agtgctaaat ttagctcaaa gcaaaaactt tcactacaac | 240 |
| cccagggacg tagtcagcaa tatcaacgta tttgttctgg aactaaaggg atctgaaaca | 300 |
| acattcatgt gtgaatatgc tgatgagaca gcaaccattg tagaatttct gaacagatgg | 360 |
| attaccttta gtcaaagcat catctcaaca ctgacttga | 399 |

```
SEQ ID NO: 171           moltype = DNA  length = 399
FEATURE                  Location/Qualifiers
misc_feature             1..399
                         note = IL-2 analog 65
source                   1..399
                         mol_type = other DNA
                         organism = synthetic construct
SEQUENCE: 171
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactacgaa   240
cccagggacg tagtcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 172           moltype = DNA  length = 399
FEATURE                  Location/Qualifiers
misc_feature             1..399
                         note = IL-2 analog 66
source                   1..399
                         mol_type = other DNA
                         organism = synthetic construct
SEQUENCE: 172
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttcgaa   240
cccagggact tcgtcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 173           moltype = DNA  length = 399
FEATURE                  Location/Qualifiers
misc_feature             1..399
                         note = IL-2 analog 67
source                   1..399
                         mol_type = other DNA
                         organism = synthetic construct
SEQUENCE: 173
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactatgac   240
cccagggact tcgtcagcaa tatcaacgta tgggttctgg acctaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 174           moltype = DNA  length = 399
FEATURE                  Location/Qualifiers
misc_feature             1..399
                         note = IL-2 analog 68
source                   1..399
                         mol_type = other DNA
                         organism = synthetic construct
SEQUENCE: 174
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttcgaa   240
cccagggaca tagtcagcaa tatcaacgaa ttcgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

SEQ ID NO: 175           moltype = DNA  length = 399
FEATURE                  Location/Qualifiers
misc_feature             1..399
                         note = IL-2 analog 69
source                   1..399
                         mol_type = other DNA
                         organism = synthetic construct
SEQUENCE: 175
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactacgaa   240
cccagggact tcctcagcaa tatcaacgaa tgggttctgg acctaaaggg atctgaaaca   300
acattcatgt gtgaatatgc tgatgagaca gcaaccattg tagaatttct gaacagatgg   360
```

```
attacctta gtcaaagcat catctcaaca ctgacttga                              399

SEQ ID NO: 176          moltype = DNA  length = 399
FEATURE                 Location/Qualifiers
misc_feature            1..399
                        note = IL-2 analog 70
source                  1..399
                        mol_type = other DNA
                        organism = synthetic construct
SEQUENCE: 176
cctacttcaa gttctacaaa gaaaacacag ctcaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attacccta gtcaaagcat catctcaaca ctgacttga                            399

SEQ ID NO: 177          moltype = DNA  length = 399
FEATURE                 Location/Qualifiers
misc_feature            1..399
                        note = IL-2 analog 71
source                  1..399
                        mol_type = other DNA
                        organism = synthetic construct
SEQUENCE: 177
cctacttcaa gttctacaaa gaaaacacag ctcaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attacccta gtcaaagcat catctcaaca ctgacttga                            399

SEQ ID NO: 178          moltype = DNA  length = 399
FEATURE                 Location/Qualifiers
misc_feature            1..399
                        note = IL-2 analog 72
source                  1..399
                        mol_type = other DNA
                        organism = synthetic construct
SEQUENCE: 178
cctacttcaa gttctacaaa gaaaacacag ctcaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa    180
gaactcaaac ctctggagga agtgctaaat ttagctcaaa gcaaaaactt tcactttgac    240
cccagggacg taggcagcaa tatcaacgta tttgttctgg aactaaaggg atctgaaaca    300
acattcatgt gtgaatatgc tgatgagaca gcaaccattg tagaatttct gaacagatgg    360
attacccta gtcaaagcat catctcaaca ctgacttga                            399

SEQ ID NO: 179          moltype = DNA  length = 399
FEATURE                 Location/Qualifiers
misc_feature            1..399
                        note = IL-2 analog 73
source                  1..399
                        mol_type = other DNA
                        organism = synthetic construct
SEQUENCE: 179
cctacttcaa gttctacaaa gaaaacacag ctcaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa    180
gaactcaaac ctctggagga agtgctaaat ttagctcaaa gcaaaaactt tcactttgac    240
cccagggact gggtcagcaa tatcaacgta tttgttctgg aactaaaggg atctgaaaca    300
acattcatgt gtgaatatgc tgatgagaca gcaaccattg tagaatttct gaacagatgg    360
attacccta gtcaaagcat catctcaaca ctgacttga                            399

SEQ ID NO: 180          moltype = DNA  length = 399
FEATURE                 Location/Qualifiers
misc_feature            1..399
                        note = IL-2 analog 74
source                  1..399
                        mol_type = other DNA
                        organism = synthetic construct
SEQUENCE: 180
cctacttcaa gttctacaaa gaaaacacag ctcaactgg agcatttact gctggattta      60
cagatgattt tgaatggaat taataattac aagaatccca aactcaccga tatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcactatgac    240
cccagggacg tagtcagcaa tatcaacgta tttgttctgg aactaaaggg atctgaaaca    300
```

```
acattcatgt gtgaatatgc tgatgagaca gcaaccattg tagaatttct gaacagatgg    360
attacccttta gtcaaagcat catctcaaca ctgacttga                          399

SEQ ID NO: 181          moltype = DNA   length = 399
FEATURE                 Location/Qualifiers
misc_feature            1..399
                        note = IL-2 analog 75
source                  1..399
                        mol_type = other DNA
                        organism = synthetic construct
SEQUENCE: 181
cctacttcaa gttctacaaa gaaaacacag ctacaactgg agcatttact gctggattta    60
cagatgattt tgaatggaat taataattac aagaatccca aactcaccgc gatgctcaca    120
aagaagtttg ccatgcccaa gaaggccaca gaactgaaac atcttcagtg tctagaacgg    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399

SEQ ID NO: 182          moltype = DNA   length = 399
FEATURE                 Location/Qualifiers
misc_feature            1..399
                        note = IL-2 analog 76
source                  1..399
                        mol_type = other DNA
                        organism = synthetic construct
SEQUENCE: 182
cctacttcaa gttctacaaa gaaaacacag ctacaactgg agcatttact gctggattta    60
cagatgattt tgaatggaat taataattac aagaatccca aactcaccgc gatgctcaca    120
aagcagtttt acatgcccaa gaaggccaca gaactgaaac atcttcagtg tctagaagga    180
gaactcaaac ctctggagga agtgctaaat ttagctcaaa gcaaaaactt tcactttgac    240
cccagggacg taggcagcaa tatcaacgta tttgttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399

SEQ ID NO: 183          moltype = DNA   length = 399
FEATURE                 Location/Qualifiers
misc_feature            1..399
                        note = IL-2 analog 77
source                  1..399
                        mol_type = other DNA
                        organism = synthetic construct
SEQUENCE: 183
cctacttcaa gttctacaaa gaaaacacag ctacaactgg agcatttact gctggattta    60
cagatgattt tgaatggaat taataattac aagaatccca aactcaccgc gatgctcaca    120
aaggagtttt acatgcccaa gaaggccaca gaactgaaac atcttcagtg tctagaacgg    180
gaactcaaac ctctggagga agtgctaaat ttagctcaaa gcaaaaactt tcactttgac    240
cccagggact gggtcagcaa tatcaacgta tttgttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399

SEQ ID NO: 184          moltype = DNA   length = 399
FEATURE                 Location/Qualifiers
misc_feature            1..399
                        note = IL-2 analog 78
source                  1..399
                        mol_type = other DNA
                        organism = synthetic construct
SEQUENCE: 184
cctacttcaa gttctacaaa gaaaacacag ctacaactgg agcatttact gctggattta    60
cagatgattt tgaatggaat taataattac aagaatcccg aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399

SEQ ID NO: 185          moltype = DNA   length = 399
FEATURE                 Location/Qualifiers
misc_feature            1..399
                        note = IL-2 analog 79
source                  1..399
                        mol_type = other DNA
                        organism = synthetic construct
SEQUENCE: 185
cctacttcaa gttctacaaa gaaaacacag ctacaactgg agcatttact gctggattta    60
cagatgattt tgaatggaat taataattac aagaatcccg aactcaccgc gatgctcaca    120
aagaagtttt acatgcccaa gaaggccaca gaactgaaac atcttcagtg tctagaagaa    180
gaactcaaac ctctggagga agtgctaaat ttagctcaca gcaaaaactt tcacttcgaa    240
```

```
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attacccttta gtcaaagcat catctcaaca ctgacttga                          399

SEQ ID NO: 186           moltype = DNA  length = 399
FEATURE                  Location/Qualifiers
misc_feature             1..399
                         note = IL-2 analog 80
source                   1..399
                         mol_type = other DNA
                         organism = synthetic construct
SEQUENCE: 186
cctacttcaa gttctacaaa gaaaacacag ctacaactgg agcatttact gctggattta    60
cagatgattt tgaatggaat taataattac aagaatcccg aactcaccgc gatgctcaca    120
aagaagtttt acatgcccaa gaaggccaca gaactgaaac atcttcagtg tctagaagaa    180
gaactcaaac ctctggagga agtgctaaat ttagctcaca gcaaaaactt tcacttcgaa    240
ggcagggacg tagtcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399

SEQ ID NO: 187           moltype = DNA  length = 399
FEATURE                  Location/Qualifiers
misc_feature             1..399
                         note = IL-2 analog 81
source                   1..399
                         mol_type = other DNA
                         organism = synthetic construct
SEQUENCE: 187
cctacttcaa gttctacaaa gaaaacacag ctacaactgg agcatttact gctggattta    60
cagatgattt tgaatggaat taataattac aagaatcccg aactcaccgc gatgctcaca    120
aagaagtttt acatgcccaa gaaggccaca gaactgaaac atcttcagtg tctagaagaa    180
gaactcaaac ctctggagga agtgctaaat ttagctcaca gcaaaaactt tcacttcgaa    240
gtcagggacg tagtcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399

SEQ ID NO: 188           moltype = DNA  length = 399
FEATURE                  Location/Qualifiers
misc_feature             1..399
                         note = IL-2 analog 82
source                   1..399
                         mol_type = other DNA
                         organism = synthetic construct
SEQUENCE: 188
cctacttcaa gttctacaaa gaaaacacag ctacaactgg agcatttacg tctggattta    60
gaaatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcactttgac    240
cccagggacg aagtgagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399

SEQ ID NO: 189           moltype = DNA  length = 399
FEATURE                  Location/Qualifiers
misc_feature             1..399
                         note = IL-2 analog 83
source                   1..399
                         mol_type = other DNA
                         organism = synthetic construct
SEQUENCE: 189
cctacttcaa gttctacaaa gaaaacacag ctacaactgg agcatttacg tcgtgatttta   60
gaaatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaca gcaaaaactt tcacttcgaa    240
cccagggacg aagtgagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399

SEQ ID NO: 190           moltype = DNA  length = 399
FEATURE                  Location/Qualifiers
misc_feature             1..399
                         note = IL-2 analog 84
source                   1..399
                         mol_type = other DNA
                         organism = synthetic construct
SEQUENCE: 190
cctacttcaa gttctacaaa gaaaacacag ctacaactgg agcatttacg tctggattta    60
gaaatgattt tgaatggaat taataattac aagaatccca aactcaccag gatgctcaca    120
tttaagtttt acatgcccaa gaaggccaca gaactgaaac atcttcagtg tctagaagaa    180
```

```
gaactcaaac ctctggagga agtgctaaat ttagctcaaa gcaaaaactt tcacgtggat  240
cccagggacg aagtgagcaa tatcaacgta tttgttctgg aactaaaggg atctgaaaca  300
acattcatgt gtgaatatgc tgatgagaca gcaaccattg tagaatttct gaacagatgg  360
attaccttta gtcaaagcat catctcaaca ctgacttga                         399

SEQ ID NO: 191         moltype = DNA  length = 399
FEATURE                Location/Qualifiers
misc_feature           1..399
                       note = IL-2 analog 85
source                 1..399
                       mol_type = other DNA
                       organism = synthetic construct
SEQUENCE: 191
cctacttcaa gttctacaaa gaaaacacag ctacaactgg agcatttact gctggattta  60
cagatgattt tgaatggaat taataattac aagaatccca aactcaccag gatgctcaca  120
tttaagtttt acatgcccaa gaaggccaca gaactgaaac atcttcagtg tctagaagaa  180
gaactcaaac ctctggagga agtgctaaat ttagctcaaa gcaaaaactt tcacttcgaa  240
cccagggacg tagtcagcaa tatcaacgta tttgttctgg aactaaaggg atctgaaaca  300
acattcatgt gtgaatatgc tgatgagaca gcaaccattg tagaatttct gaacagatgg  360
attaccttta gtcaaagcat catctcaaca ctgacttga                         399

SEQ ID NO: 192         moltype = DNA  length = 399
FEATURE                Location/Qualifiers
misc_feature           1..399
                       note = IL-2 analog 86
source                 1..399
                       mol_type = other DNA
                       organism = synthetic construct
SEQUENCE: 192
cctacttcaa gttctacaaa gaaaacacag ctacaactgg agcatttacg tctggattta  60
gaaatgattt tgaatggaat taataattac aagaatccca aactcaccag gatgctcaca  120
tttaagtttt acatgcccaa gaaggccaca gaactgaaac atcttcagtg tctagaagaa  180
gaactcaaac ctctggagga agtgctaaat ttagctcaaa gcaaaaactt tcacttcgaa  240
cccagggacg tagtcagcaa tatcaacgta tttgttctgg aactaaaggg atctgaaaca  300
acattcatgt gtgaatatgc tgatgagaca gcaaccattg tagaatttct gaacagatgg  360
attaccttta gtcaaagcat catctcaaca ctgacttga                         399

SEQ ID NO: 193         moltype = DNA  length = 399
FEATURE                Location/Qualifiers
misc_feature           1..399
                       note = IL-2 analog 87
source                 1..399
                       mol_type = other DNA
                       organism = synthetic construct
SEQUENCE: 193
cctacttcaa gttctacaaa gaaaacacag ctacaactgg agcatttacg tcgtgattta  60
gaaatgattt tgaatggaat taataattac aagaatccca aactcaccag gatgctcaca  120
tttaagtttt acatgcccaa gaaggccaca gaactgaaac atcttcagtg tctagaagaa  180
gaactcaaac ctctggagga agtgctaaat ttagctcaaa gcaaaaactt tcacttcgaa  240
cccagggacg tagtcagcaa tatcaacgta tttgttctgg aactaaaggg atctgaaaca  300
acattcatgt gtgaatatgc tgatgagaca gcaaccattg tagaatttct gaacagatgg  360
attaccttta gtcaaagcat catctcaaca ctgacttga                         399

SEQ ID NO: 194         moltype = DNA  length = 399
FEATURE                Location/Qualifiers
misc_feature           1..399
                       note = IL-2 analog 88
source                 1..399
                       mol_type = other DNA
                       organism = synthetic construct
SEQUENCE: 194
cctacttcaa gttctacaaa gaaaacacag ctacaactgg agcatttact gctggattta  60
cagatgattt tgaatggaat taataattac aagaatccca aactcaccag gatgctcaca  120
tttaagtttt acatgcccaa gaaggccaca gaactgaaac atcttcagtg tctagaagac  180
gaactcaaac ctctggagga agtgctaaat ttagctcaaa gcaaaaactt tcacttcgaa  240
cccagggacg tagtcagcaa tatcaacgta tttgttctgg aactaaaggg atctgaaaca  300
acattcatgt gtgaatatgc tgatgagaca gcaaccattg tagaatttct gaacagatgg  360
attaccttta gtcaaagcat catctcaaca ctgacttga                         399

SEQ ID NO: 195         moltype = DNA  length = 399
FEATURE                Location/Qualifiers
misc_feature           1..399
                       note = IL-2 analog 89
source                 1..399
                       mol_type = other DNA
                       organism = synthetic construct
SEQUENCE: 195
cctacttcaa gttctacaaa gaaaacacag ctacaactgg agcatttact gctggattta  60
cagatgattt tgaatggaat taataattac aagaatccca aactcaccgc gatgctcaca  120
```

```
tttaagtttt acatgcccaa gaaggccaca gaactgaaac atcttcagtg tctagaagaa    180
gaactcaaac ctctggagca ggtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attacctta gtcaaagcat catctcaaca ctgacttga                            399
```

```
SEQ ID NO: 196          moltype = DNA   length = 399
FEATURE                 Location/Qualifiers
misc_feature            1..399
                        note = IL-2 analog 90
source                  1..399
                        mol_type = other DNA
                        organism = synthetic construct
SEQUENCE: 196
cctacttcaa gttctacaaa gaaaacacag ctacaactgg agcatttact gctggattta    60
cagatgattt tgaatggaat taataattac aagaatccca aactcaccag gatgctcaca    120
tggaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attacctta gtcaaagcat catctcaaca ctgacttga                            399
```

```
SEQ ID NO: 197          moltype = DNA   length = 399
FEATURE                 Location/Qualifiers
misc_feature            1..399
                        note = IL-2 analog 91
source                  1..399
                        mol_type = other DNA
                        organism = synthetic construct
SEQUENCE: 197
cctacttcaa gttctacaaa gaaaacacag ctacaactgg agcatttact gctggattta    60
cagatgattt tgaatggaat taataattac aagaatccca aactcaccag gatgctcaca    120
tttaagtttt acatgcccaa gaaggccaca gaactgaaac atcttcagtg tctagaacaa    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attacctta gtcaaagcat catctcaaca ctgacttga                            399
```

```
SEQ ID NO: 198          moltype = DNA   length = 399
FEATURE                 Location/Qualifiers
misc_feature            1..399
                        note = IL-2 analog 92
source                  1..399
                        mol_type = other DNA
                        organism = synthetic construct
SEQUENCE: 198
cctacttcaa gttctacaaa gaaaacacag ctacaactgg agcatttact gctggattta    60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacaca tttgttctgg aactaaaggg atctgaaaca    300
acattcatgt gtgaatatgc tgatgagaca gcaaccattg tagaatttct gaacagatgg    360
attacctta gtcaaagcat catctcaaca ctgacttga                            399
```

```
SEQ ID NO: 199          moltype = DNA   length = 399
FEATURE                 Location/Qualifiers
misc_feature            1..399
                        note = IL-2 analog 93
source                  1..399
                        mol_type = other DNA
                        organism = synthetic construct
SEQUENCE: 199
cctacttcaa gttctacaaa gaaaacacag ctacaactgg agcatttact gctggattta    60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggagg tagtcagcaa tatcaacaca tttgttctgg aactaaaggg atctgaaaca    300
acattcatgt gtgaatatgc tgatgagaca gcaaccattg tagaatttct gaacagatgg    360
attacctta gtcaaagcat catctcaaca ctgacttga                            399
```

```
SEQ ID NO: 200          moltype = DNA   length = 399
FEATURE                 Location/Qualifiers
misc_feature            1..399
                        note = IL-2 analog 94
source                  1..399
                        mol_type = other DNA
                        organism = synthetic construct
SEQUENCE: 200
cctacttcaa gttctacaaa gaaaacacag ctacaactgg agcatttact gctggattta    60
```

```
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacgta tttgttttcg aattcaaggg atctgaaaca    300
acattcatgt gtgaatatgc tgatgagaca gcaaccattg tagaatttct gaacagatgg    360
attaccttta gtcaaagcat catctcaaca ctgacttga                           399
```

| | | |
|---|---|---|
| SEQ ID NO: 201 | moltype = DNA length = 399 | |
| FEATURE | Location/Qualifiers | |
| misc_feature | 1..399 | |
| | note = IL-2 analog 95 | |
| source | 1..399 | |
| | mol_type = other DNA | |
| | organism = synthetic construct | |

SEQUENCE: 201
```
cctacttcaa gttctacaaa gaaaacacag ctacaactgg agcatttact gctggattta    60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agggctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

| | | |
|---|---|---|
| SEQ ID NO: 202 | moltype = DNA length = 399 | |
| FEATURE | Location/Qualifiers | |
| misc_feature | 1..399 | |
| | note = IL-2 analog 96 | |
| source | 1..399 | |
| | mol_type = other DNA | |
| | organism = synthetic construct | |

SEQUENCE: 202
```
cctacttcaa gttctacaaa gaaaacacag ctacaactgg agcatttact gctggattta    60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agggctaaat ttagctgcaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

| | | |
|---|---|---|
| SEQ ID NO: 203 | moltype = DNA length = 399 | |
| FEATURE | Location/Qualifiers | |
| misc_feature | 1..399 | |
| | note = IL-2 analog 97 | |
| source | 1..399 | |
| | mol_type = other DNA | |
| | organism = synthetic construct | |

SEQUENCE: 203
```
cctacttcaa gttctacaaa gaaaacacag ctacaactgg agcatttact gctggattta    60
cagatgattt tgaatggaat taataattac aagaatccca aactcaccgc gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcactttgaa    240
cccagggact taatcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

| | | |
|---|---|---|
| SEQ ID NO: 204 | moltype = DNA length = 399 | |
| FEATURE | Location/Qualifiers | |
| misc_feature | 1..399 | |
| | note = IL-2 analog 98 | |
| source | 1..399 | |
| | mol_type = other DNA | |
| | organism = synthetic construct | |

SEQUENCE: 204
```
cctacttcaa gttctacaaa gaaaacacag ctacaactgg agcatttact gctggattta    60
cagatgattt tgaatggaat taataattac aagaatccca aactcaccgc gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcactttgag    240
cccagggacg taatcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

| | | |
|---|---|---|
| SEQ ID NO: 205 | moltype = DNA length = 399 | |
| FEATURE | Location/Qualifiers | |
| misc_feature | 1..399 | |
| | note = IL-2 analog 99 | |
| source | 1..399 | |
| | mol_type = other DNA | |
| | organism = synthetic construct | |

SEQUENCE: 205

```
cctacttcaa gttctacaaa gaaaacacag ctacaactgg agcatttact gctggattta   60
cagatgattt tgaatggaat taataattac aagaatccca aactcaccgc gatgctcaca  120
tttaagtttt acatgcccaa gaaggccaca gaactgaaac atcttcagtg tctagaagaa  180
gaactcaaac ctctggagga agtgctaaat ttagctcaaa gcaaaaactt tcactttgag  240
cccagggact tagtcagcaa tatcaacgta tttgttctgg aactaaaggg atctgaaaca  300
acattcatgt gtgaatatgc tgatgagaca gcaaccattg tagaatttct gaacagatgg  360
attccttta gtcaaagcat catctcaaca ctgacttga                          399

SEQ ID NO: 206          moltype = DNA   length = 399
FEATURE                 Location/Qualifiers
misc_feature            1..399
                        note = IL-2 analog 100
source                  1..399
                        mol_type = other DNA
                        organism = synthetic construct
SEQUENCE: 206
cctacttcaa gttctacaaa gaaaacacag ctacaactgg agcatttact gctggattta   60
cagatgattt tgaatggaat taataattac aagaatccca aactcaccag gatgctcaca  120
tttaagtttt acatgcccaa gaaggccaca gaactgaaac atcttcagtg tctagaagaa  180
gaactcaaac ctctggagga agtgctaaat ttagctcaaa gcaaaaactt tcacttcgaa  240
cccagggact acgtcagcaa tatcaacgta tttgttctgg aactaaaggg atctgaaaca  300
acattcatgt gtgaatatgc tgatgagaca gcaaccattg tagaatttct gaacagatgg  360
attccttta gtcaaagcat catctcaaca ctgacttga                          399

SEQ ID NO: 207          moltype = DNA   length = 399
FEATURE                 Location/Qualifiers
misc_feature            1..399
                        note = IL-2 analog 101
source                  1..399
                        mol_type = other DNA
                        organism = synthetic construct
SEQUENCE: 207
cctacttcaa gttctacaaa gaaaacacag ctacaactgg agcatttact gctggattta   60
cagatgattt tgaatggaat taataattac aagaatccca aactcaccag gatgctcaca  120
tttaagtttt acatgcccaa gaaggccaca gaactgaaac atcttcagtg tctagaagaa  180
gaactcaaac ctctggagga agtgctaaat ttagctcaaa gcaaaaactt tcacttcgaa  240
cccagggacc tggccagcaa tatcaacgta tttgttctgg aactaaaggg atctgaaaca  300
acattcatgt gtgaatatgc tgatgagaca gcaaccattg tagaatttct gaacagatgg  360
attccttta gtcaaagcat catctcaaca ctgacttga                          399

SEQ ID NO: 208          moltype = DNA   length = 399
FEATURE                 Location/Qualifiers
misc_feature            1..399
                        note = IL-2 analog 102
source                  1..399
                        mol_type = other DNA
                        organism = synthetic construct
SEQUENCE: 208
cctacttcaa gttctacaaa gaaaacacag ctacaactgg agcatttact gctggattta   60
cagatgattt tgaatggaat taataattac aagaatccca aactcaccag gatgctcaca  120
tttaagtttt acatgcccaa gaaggccaca gaactgaaac atcttcagtg tctagaagaa  180
gaactcaaac ctctggagga agtgctaaat ttagctcaaa gcaaaaactt tcacttcgaa  240
cccagggacg tagtcagcaa tatcaacgta attgttctgg aactaaaggg atctgaaaca  300
acattcatgt gtgaatatgc tgatgagaca gcaaccattg tagaatttct gaacagatgg  360
attccttta gtcaaagcat catctcaaca ctgacttga                          399

SEQ ID NO: 209          moltype = DNA   length = 399
FEATURE                 Location/Qualifiers
misc_feature            1..399
                        note = IL-2 analog 103
source                  1..399
                        mol_type = other DNA
                        organism = synthetic construct
SEQUENCE: 209
cctacttcaa gttctacaaa gaaaacacag ctacaactgg agcatttacg tctggattta   60
gaatgattt tgaatggaat taataattac aagaatccca aactcaccgc gatgctcaca  120
tttaagtttt acatgcccaa gaaggccaca gaactgaaac atcttcagtg tctagaagaa  180
gaactcaaac ctctggagga agtgctaaat ttagctcaaa gcaaaaactt tcacttcgaa  240
cccagggacg tagtcagcaa tatcaacgta tttgttctgg aactaaaggg atctgaaaca  300
acattcatgt gtgaatatgc tgatgagaca gcaaccattg tagaatttct gaacagatgg  360
attccttta gtcaaagcat catctcaaca ctgacttga                          399

SEQ ID NO: 210          moltype = DNA   length = 399
FEATURE                 Location/Qualifiers
misc_feature            1..399
                        note = IL-2 analog 104
source                  1..399
                        mol_type = other DNA
                        organism = synthetic construct
```

```
SEQUENCE: 210
cctacttcaa gttctacaaa gaaaacacag ctacaactgg agcatttacg tctggattta   60
gaaatgattt tgaatggaat taataattac aagaatccca aactcaccag gatgctcaca  120
tttaagtttt acatgcccaa gaaggccaca gaactgaaac atcttcagtg tctagaagac  180
gaactcaaac ctctggagga agtgctaaat ttagctcaaa gcaaaaactt tcacttcgaa  240
cccagggacg tagtcagcaa tatcaacgta tttgttctgg aactaaaggg atctgaaaca  300
acattcatgt gtgaatatgc tgatgagaca gcaaccattg tagaatttct gaacagatgg  360
attacccttta gtcaaagcat catctcaaca ctgacttga                         399

SEQ ID NO: 211          moltype = DNA  length = 399
FEATURE                 Location/Qualifiers
misc_feature            1..399
                        note = IL-2 analog 105
source                  1..399
                        mol_type = other DNA
                        organism = synthetic construct
SEQUENCE: 211
cctacttcaa gttctacaaa gaaaacacag ctacaactgg agcatttacg tctggattta   60
gaaatgattt tgaatggaat taataattac aagaatccca aactcaccag gatgctcaca  120
tttaagtttt acatgcccaa gaaggccaca gaactgaaac atcttcagtg tctagaagaa  180
gaactcaaac ctctggagga cgtgctaaat ttagctcaaa gcaaaaactt tcacttcgaa  240
cccagggacg tagtcagcaa tatcaacgta tttgttctgg aactaaaggg atctgaaaca  300
acattcatgt gtgaatatgc tgatgagaca gcaaccattg tagaatttct gaacagatgg  360
attacccttta gtcaaagcat catctcaaca ctgacttga                         399

SEQ ID NO: 212          moltype = AA  length = 133
FEATURE                 Location/Qualifiers
REGION                  1..133
                        note = General Formula 1
VARIANT                 1
                        note = Xaa is a deletion
VARIANT                 18
                        note = Xaa is leucine (L) or arginine (R)
VARIANT                 19
                        note = Xaa is leucine (L) or tyrosine (Y)
VARIANT                 22
                        note = Xaa is glutamic acid (E) or glutamine (Q)
VARIANT                 38
                        note = Xaa is alanine (A), aspartic acid (D), or arginine
                         (R)
VARIANT                 42
                        note = Xaa is alanine (A), phenylalanine (F), lysine (K),
                         or tryptophan (W)
VARIANT                 43
                        note = Xaa is glutamic acid (E), lysine (K), or glutamine
                         (Q)
VARIANT                 45
                        note = Xaa is alanine (A) or tyrosine (Y)
VARIANT                 61
                        note = Xaa is aspartic acid (D), glutamic acid (E),
                         glutamine (Q), or arginine (R)
VARIANT                 68
                        note = Xaa is aspartic acid (D) or glutamic acid (E)
VARIANT                 74
                        note = Xaa is histidine (H) or glutamine (Q)
VARIANT                 80
                        note = Xaa is phenylalanine (F), leucine (L), valine (V),
                         or tyrosine (Y)
VARIANT                 81
                        note = Xaa is aspartic acid (D), glutamic acid (E), or
                         arginine (R)
VARIANT                 84
                        note = Xaa is aspartic acid (D) or glutamic acid (E)
VARIANT                 85
                        note = Xaa is alanine (A), glutamic acid (E), glycine (G),
                         leucine (L), valine (V), tryptophan (W), or tyrosine (Y)
VARIANT                 86
                        note = Xaa is alanine (A), glycine (G), isoleucine (I), or
                         valine (V)
VARIANT                 91
                        note = Xaa is threonine (T) or valine (V)
VARIANT                 92
                        note = Xaa is phenylalanine (F), isoleucine (I), or
                         tyrosine (Y)
VARIANT                 94
                        note = Xaa is phenylalanine (F) or leucine (L)
VARIANT                 96
                        note = Xaa is phenylalanine (F) or leucine (L)
source                  1..133
```

```
                           mol_type = protein
                           organism = synthetic construct
SEQUENCE: 212
XPTSSSTKKT QLQLEHLXXD LXMILNGINN YKNPKLTXML TXXFXMPKKA TELKHLQCLE      60
XELKPLEXVL NLAXSKNFHX XPRXXXSNIN XXVXEXKGSE TTFMCEYADE TATIVEFLNR     120
WITFSQSIIS TLT                                                       133

SEQ ID NO: 213             moltype = AA  length = 133
FEATURE                    Location/Qualifiers
REGION                     1..133
                           note = General Formula 2
VARIANT                    1
                           note = Xaa is a deletion
VARIANT                    18
                           note = Xaa is leucine (L) or arginine (R)
VARIANT                    22
                           note = Xaa is glutamic acid (E) or glutamine (Q)
VARIANT                    38
                           note = Xaa is alanine (A) or arginine (R)
VARIANT                    42
                           note = Xaa is phenylalanine (F) or lysine (K)
VARIANT                    61
                           note = Xaa is aspartic acid (D) or glutamic acid (E)
VARIANT                    68
                           note = Xaa is aspartic acid (D) or glutamic acid (E)
VARIANT                    81
                           note = Xaais aspartic acid (D) or glutamic acid (E)
VARIANT                    85
                           note = Xaa is leucine (L) or valine (V)
VARIANT                    86
                           note = Xaa is isoleucine (I) or valine (V)
source                     1..133
                           mol_type = protein
                           organism = synthetic construct
SEQUENCE: 213
XPTSSSTKKT QLQLEHLXLD LXMILNGINN YKNPKLTXML TXKFYMPKKA TELKHLQCLE      60
XELKPLEXVL NLAQSKNFHF XPRDXXSNIN VFVLELKGSE TTFMCEYADE TATIVEFLNR     120
WITFSQSIIS TLT                                                       133

SEQ ID NO: 214             moltype = DNA  length = 33
FEATURE                    Location/Qualifiers
misc_feature               1..33
                           note = primer #1 (IL2_L12F_F)
source                     1..33
                           mol_type = other DNA
                           organism = synthetic construct
SEQUENCE: 214
caaagaaaac acagtttcaa ctggagcatt tac                                  33

SEQ ID NO: 215             moltype = DNA  length = 33
FEATURE                    Location/Qualifiers
misc_feature               1..33
                           note = primer #2 (IL2_L12F_R)
source                     1..33
                           mol_type = other DNA
                           organism = synthetic construct
SEQUENCE: 215
gtaaatgctc cagttgaaac tgtgttttct ttg                                  33

SEQ ID NO: 216             moltype = DNA  length = 33
FEATURE                    Location/Qualifiers
misc_feature               1..33
                           note = primer #3 (IL2_L12V_F)
source                     1..33
                           mol_type = other DNA
                           organism = synthetic construct
SEQUENCE: 216
caaagaaaac acaggtacaa ctggagcatt tac                                  33

SEQ ID NO: 217             moltype = DNA  length = 33
FEATURE                    Location/Qualifiers
misc_feature               1..33
                           note = primer #4 (IL2_L12V_R)
source                     1..33
                           mol_type = other DNA
                           organism = synthetic construct
SEQUENCE: 217
gtaaatgctc cagttgtacc tgtgttttct ttg                                  33
```

```
SEQ ID NO: 218          moltype = DNA   length = 39
FEATURE                 Location/Qualifiers
misc_feature            1..39
                        note = primer #5 (IL2_L18R_L19R_Q22E_F)
source                  1..39
                        mol_type = other DNA
                        organism = synthetic construct
SEQUENCE: 218
ctggagcatt tacgtcgtga tttagaaatg attttgaat                                 39

SEQ ID NO: 219          moltype = DNA   length = 39
FEATURE                 Location/Qualifiers
misc_feature            1..39
                        note = primer #6 (IL2_L18R_L19R_Q22E_R)
source                  1..39
                        mol_type = other DNA
                        organism = synthetic construct
SEQUENCE: 219
attcaaaatc atttctaaat cacgacgtaa atgctccag                                 39

SEQ ID NO: 220          moltype = DNA   length = 39
FEATURE                 Location/Qualifiers
misc_feature            1..39
                        note = primer #7 (IL2_L18R_Q22E_F)
source                  1..39
                        mol_type = other DNA
                        organism = synthetic construct
SEQUENCE: 220
ctggagcatt tacgtctgga tttagaaatg attttgaat                                 39

SEQ ID NO: 221          moltype = DNA   length = 39
FEATURE                 Location/Qualifiers
misc_feature            1..39
                        note = primer #8 (IL2_L18R_Q22E_R)
source                  1..39
                        mol_type = other DNA
                        organism = synthetic construct
SEQUENCE: 221
attcaaaatc atttctaaat ccagacgtaa atgctccag                                 39

SEQ ID NO: 222          moltype = DNA   length = 33
FEATURE                 Location/Qualifiers
misc_feature            1..33
                        note = primer #9 (IL2_L19F_F)
source                  1..33
                        mol_type = other DNA
                        organism = synthetic construct
SEQUENCE: 222
gagcatttac tgttcgattt acagatgatt ttg                                       33

SEQ ID NO: 223          moltype = DNA   length = 33
FEATURE                 Location/Qualifiers
misc_feature            1..33
                        note = primer #10 (IL2_L19F_R)
source                  1..33
                        mol_type = other DNA
                        organism = synthetic construct
SEQUENCE: 223
caaaatcatc tgtaaatcga acagtaaatg ctc                                       33

SEQ ID NO: 224          moltype = DNA   length = 33
FEATURE                 Location/Qualifiers
misc_feature            1..33
                        note = primer #11 (IL2_L19V_F)
source                  1..33
                        mol_type = other DNA
                        organism = synthetic construct
SEQUENCE: 224
gagcatttac tggtggattt acagatgatt ttg                                       33

SEQ ID NO: 225          moltype = DNA   length = 33
FEATURE                 Location/Qualifiers
misc_feature            1..33
                        note = primer #12 (IL2_L19V_R)
source                  1..33
                        mol_type = other DNA
                        organism = synthetic construct
SEQUENCE: 225
caaaatcatc tgtaaatcca ccagtaaatg ctc                                       33
```

```
SEQ ID NO: 226          moltype = DNA   length = 33
FEATURE                 Location/Qualifiers
misc_feature            1..33
                        note = primer #13 (IL2_L19Y_F)
source                  1..33
                        mol_type = other DNA
                        organism = synthetic construct
SEQUENCE: 226
caactggagc atttactgta cgatttacag atg                                        33

SEQ ID NO: 227          moltype = DNA   length = 33
FEATURE                 Location/Qualifiers
misc_feature            1..33
                        note = primer #14 (IL2_L19Y_R)
source                  1..33
                        mol_type = other DNA
                        organism = synthetic construct
SEQUENCE: 227
catctgtaaa tcgtacagta aatgctccag ttg                                        33

SEQ ID NO: 228          moltype = DNA   length = 34
FEATURE                 Location/Qualifiers
misc_feature            1..34
                        note = primer #15 (IL2_D20F_F)
source                  1..34
                        mol_type = other DNA
                        organism = synthetic construct
SEQUENCE: 228
ggagcattta ctgctgtttt tacagatgat tttg                                       34

SEQ ID NO: 229          moltype = DNA   length = 34
FEATURE                 Location/Qualifiers
misc_feature            1..34
                        note = primer #16 (IL2_D20F_R)
source                  1..34
                        mol_type = other DNA
                        organism = synthetic construct
SEQUENCE: 229
caaaatcatc tgtaaaaaca gcagtaaatg ctcc                                       34

SEQ ID NO: 230          moltype = DNA   length = 33
FEATURE                 Location/Qualifiers
misc_feature            1..33
                        note = primer #17 (IL2_D20V_F)
source                  1..33
                        mol_type = other DNA
                        organism = synthetic construct
SEQUENCE: 230
gagcatttac tgctggtttt acagatgatt ttg                                        33

SEQ ID NO: 231          moltype = DNA   length = 33
FEATURE                 Location/Qualifiers
misc_feature            1..33
                        note = primer #18 (IL2_D20V_R)
source                  1..33
                        mol_type = other DNA
                        organism = synthetic construct
SEQUENCE: 231
caaaatcatc tgtaaaacca gcagtaaatg ctc                                        33

SEQ ID NO: 232          moltype = DNA   length = 33
FEATURE                 Location/Qualifiers
misc_feature            1..33
                        note = primer #19 (IL2_K32C_F)
source                  1..33
                        mol_type = other DNA
                        organism = synthetic construct
SEQUENCE: 232
ggaattaata attactgtaa tcccaaactc acc                                        33

SEQ ID NO: 233          moltype = DNA   length = 33
FEATURE                 Location/Qualifiers
misc_feature            1..33
                        note = primer #20 (IL2_K32C_R)
source                  1..33
                        mol_type = other DNA
                        organism = synthetic construct
SEQUENCE: 233
```

```
ggtgagtttg ggattacagt aattattaat tcc                              33

SEQ ID NO: 234          moltype = DNA   length = 33
FEATURE                 Location/Qualifiers
misc_feature            1..33
                        note = primer #21 (IL2_K35C_F)
source                  1..33
                        mol_type = other DNA
                        organism = synthetic construct
SEQUENCE: 234
aattacaaga atccctgtct caccaggatg ctc                              33

SEQ ID NO: 235          moltype = DNA   length = 33
FEATURE                 Location/Qualifiers
misc_feature            1..33
                        note = primer #22 (IL2_K35C_R)
source                  1..33
                        mol_type = other DNA
                        organism = synthetic construct
SEQUENCE: 235
gagcatcctg gtgagacagg gattcttgta att                              33

SEQ ID NO: 236          moltype = DNA   length = 33
FEATURE                 Location/Qualifiers
misc_feature            1..33
                        note = primer #23 (IL2_K35E_F)
source                  1..33
                        mol_type = other DNA
                        organism = synthetic construct
SEQUENCE: 236
taattacaag aatcccgaac tcaccgcgat gct                              33

SEQ ID NO: 237          moltype = DNA   length = 33
FEATURE                 Location/Qualifiers
misc_feature            1..33
                        note = primer #24 (IL2_K35E_R)
source                  1..33
                        mol_type = other DNA
                        organism = synthetic construct
SEQUENCE: 237
agcatcgcgg tgagttcggg attcttgtaa tta                              33

SEQ ID NO: 238          moltype = DNA   length = 25
FEATURE                 Location/Qualifiers
misc_feature            1..25
                        note = primer #25 (IL2_R38A_F)
source                  1..25
                        mol_type = other DNA
                        organism = synthetic construct
SEQUENCE: 238
ccaaactcac cgcgatgctc acatt                                       25

SEQ ID NO: 239          moltype = DNA   length = 25
FEATURE                 Location/Qualifiers
misc_feature            1..25
                        note = primer #26 (IL2_R38A_R)
source                  1..25
                        mol_type = other DNA
                        organism = synthetic construct
SEQUENCE: 239
aatgtgagca tcgcggtgag tttgg                                       25

SEQ ID NO: 240          moltype = DNA   length = 33
FEATURE                 Location/Qualifiers
misc_feature            1..33
                        note = primer #27 (IL2_R38A_F42F_F)
source                  1..33
                        mol_type = other DNA
                        organism = synthetic construct
SEQUENCE: 240
caccgcgatg ctcacattta agttttacat gcc                              33

SEQ ID NO: 241          moltype = DNA   length = 33
FEATURE                 Location/Qualifiers
misc_feature            1..33
                        note = primer #28 (IL2_R38A_F42F_R)
source                  1..33
                        mol_type = other DNA
                        organism = synthetic construct
```

```
SEQUENCE: 241
ggcatgtaaa acttaaatgt gagcatcgcg gtg                                33

SEQ ID NO: 242          moltype = DNA   length = 25
FEATURE                 Location/Qualifiers
misc_feature            1..25
                        note = primer #29 (IL2_A38R_F)
source                  1..25
                        mol_type = other DNA
                        organism = synthetic construct
SEQUENCE: 242
ccaaactcac caggatgctc acatt                                         25

SEQ ID NO: 243          moltype = DNA   length = 25
FEATURE                 Location/Qualifiers
misc_feature            1..25
                        note = primer #30 (IL2_A38R_R)
source                  1..25
                        mol_type = other DNA
                        organism = synthetic construct
SEQUENCE: 243
aatgtgagca tcctggtgag tttgg                                         25

SEQ ID NO: 244          moltype = DNA   length = 30
FEATURE                 Location/Qualifiers
misc_feature            1..30
                        note = primer #31 (IL2_R38D_F)
source                  1..30
                        mol_type = other DNA
                        organism = synthetic construct
SEQUENCE: 244
aagaatccca aactcaccga tatgctcaca                                    30

SEQ ID NO: 245          moltype = DNA   length = 30
FEATURE                 Location/Qualifiers
misc_feature            1..30
                        note = primer #32 (IL2_R38D_R)
source                  1..30
                        mol_type = other DNA
                        organism = synthetic construct
SEQUENCE: 245
tgtgagcata tcggtgagtt tgggattctt                                    30

SEQ ID NO: 246          moltype = DNA   length = 30
FEATURE                 Location/Qualifiers
misc_feature            1..30
                        note = primer #33 (IL2_F42A_F)
source                  1..30
                        mol_type = other DNA
                        organism = synthetic construct
SEQUENCE: 246
ccaggatgct cacagctaag ttttacatgc                                    30

SEQ ID NO: 247          moltype = DNA   length = 30
FEATURE                 Location/Qualifiers
misc_feature            1..30
                        note = primer #34 (IL2_F42A_R)
source                  1..30
                        mol_type = other DNA
                        organism = synthetic construct
SEQUENCE: 247
gcatgtaaaa cttagctgtg agcatcctgg                                    30

SEQ ID NO: 248          moltype = DNA   length = 30
FEATURE                 Location/Qualifiers
misc_feature            1..30
                        note = primer #35 (IL2_F42K_F)
source                  1..30
                        mol_type = other DNA
                        organism = synthetic construct
SEQUENCE: 248
ccaggatgct cacaaagaag ttttacatgc                                    30

SEQ ID NO: 249          moltype = DNA   length = 30
FEATURE                 Location/Qualifiers
misc_feature            1..30
                        note = primer #36 (IL2_F42K_R)
source                  1..30
                        mol_type = other DNA
```

```
                        organism = synthetic construct
SEQUENCE: 249
gcatgtaaaa cttctttgtg agcatcctgg                                              30

SEQ ID NO: 251          moltype = DNA   length = 30
FEATURE                 Location/Qualifiers
misc_feature            1..30
                        note = primer #37 (IL2_F42K_K43E_F)
source                  1..30
                        mol_type = other DNA
                        organism = synthetic construct
SEQUENCE: 250
atgctcacaa aggagtttta catgcccaag                                              30

SEQ ID NO: 251          moltype = DNA   length = 30
FEATURE                 Location/Qualifiers
misc_feature            1..30
                        note = primer #38 (IL2_F42K_K43E_R)
source                  1..30
                        mol_type = other DNA
                        organism = synthetic construct
SEQUENCE: 251
cttgggcatg taaaactcct ttgtgagcat                                              30

SEQ ID NO: 252          moltype = DNA   length = 30
FEATURE                 Location/Qualifiers
misc_feature            1..30
                        note = primer #39 (IL2_F42K_K43Q_F)
source                  1..30
                        mol_type = other DNA
                        organism = synthetic construct
SEQUENCE: 252
atgctcacaa agcagtttta catgcccaag                                              30

SEQ ID NO: 253          moltype = DNA   length = 30
FEATURE                 Location/Qualifiers
misc_feature            1..30
                        note = primer #40 (IL2_F42K_K43Q_R)
source                  1..30
                        mol_type = other DNA
                        organism = synthetic construct
SEQUENCE: 253
cttgggcatg taaaactgct ttgtgagcat                                              30

SEQ ID NO: 254          moltype = DNA   length = 30
FEATURE                 Location/Qualifiers
misc_feature            1..30
                        note = primer #41 (IL2_K42F_F)
source                  1..30
                        mol_type = other DNA
                        organism = synthetic construct
SEQUENCE: 254
ccaggatgct cacatttaag ttttacatgc                                              30

SEQ ID NO: 255          moltype = DNA   length = 30
FEATURE                 Location/Qualifiers
misc_feature            1..30
                        note = primer #42 (IL2_K42F_R)
source                  1..30
                        mol_type = other DNA
                        organism = synthetic construct
SEQUENCE: 255
gcatgtaaaa cttaaatgtg agcatcctgg                                              30

SEQ ID NO: 256          moltype = DNA   length = 39
FEATURE                 Location/Qualifiers
misc_feature            1..39
                        note = primer #43 (IL2_K42F_F_long)
source                  1..39
                        mol_type = other DNA
                        organism = synthetic construct
SEQUENCE: 256
ctcaccagga tgctcacatt taagttttac atgcccaag                                    39

SEQ ID NO: 257          moltype = DNA   length = 39
FEATURE                 Location/Qualifiers
misc_feature            1..39
                        note = primer #44 (IL2_K42F_R_long)
source                  1..39
```

```
                                mol_type = other DNA
                                organism = synthetic construct
SEQUENCE: 257
cttgggcatg taaaacttaa atgtgagcat cctggtgag                              39

SEQ ID NO: 258          moltype = DNA   length = 33
FEATURE                 Location/Qualifiers
misc_feature            1..33
                        note = primer #45 (IL2_F42W_F)
source                  1..33
                        mol_type = other DNA
                        organism = synthetic construct
SEQUENCE: 258
accaggatgc tcacatggaa gttttacatg ccc                                    33

SEQ ID NO: 259          moltype = DNA   length = 33
FEATURE                 Location/Qualifiers
misc_feature            1..33
                        note = primer #46 (IL2_F42W_R)
source                  1..33
                        mol_type = other DNA
                        organism = synthetic construct
SEQUENCE: 259
gggcatgtaa aacttccatg tgagcatcct ggt                                    33

SEQ ID NO: 260          moltype = DNA   length = 33
FEATURE                 Location/Qualifiers
misc_feature            1..33
                        note = primer #47 (IL2_K43C_F)
source                  1..33
                        mol_type = other DNA
                        organism = synthetic construct
SEQUENCE: 260
aggatgctca cattttgttt ttacatgccc aag                                    33

SEQ ID NO: 261          moltype = DNA   length = 33
FEATURE                 Location/Qualifiers
misc_feature            1..33
                        note = primer #48 (IL2_K43C_R)
source                  1..33
                        mol_type = other DNA
                        organism = synthetic construct
SEQUENCE: 261
cttgggcatg taaaaacaaa atgtgagcat cct                                    33

SEQ ID NO: 262          moltype = DNA   length = 19
FEATURE                 Location/Qualifiers
misc_feature            1..19
                        note = primer #49 (IL2_Y45A_F)
source                  1..19
                        mol_type = other DNA
                        organism = synthetic construct
SEQUENCE: 262
gaagtttgcc atgcccaag                                                    19

SEQ ID NO: 263          moltype = DNA   length = 19
FEATURE                 Location/Qualifiers
misc_feature            1..19
                        note = primer #50 (IL2_Y45A_R)
source                  1..19
                        mol_type = other DNA
                        organism = synthetic construct
SEQUENCE: 263
cttgggcatg gcaaacttc                                                    19

SEQ ID NO: 264          moltype = DNA   length = 34
FEATURE                 Location/Qualifiers
misc_feature            1..34
                        note = primer #51 (IL2_Y45A_F_long)
source                  1..34
                        mol_type = other DNA
                        organism = synthetic construct
SEQUENCE: 264
gctcacaaag aagtttgcca tgcccaagaa ggcc                                   34

SEQ ID NO: 265          moltype = DNA   length = 34
FEATURE                 Location/Qualifiers
misc_feature            1..34
                        note = primer #52 (IL2_Y45A_R_long)
```

```
source                  1..34
                        mol_type = other DNA
                        organism = synthetic construct
SEQUENCE: 265
ggccttcttg ggcatggcaa acttctttgt gagc                                  34

SEQ ID NO: 266          moltype = DNA   length = 33
FEATURE                 Location/Qualifiers
misc_feature            1..33
                        note = primer #53 (IL2_K48C_F)
source                  1..33
                        mol_type = other DNA
                        organism = synthetic construct
SEQUENCE: 266
aagttttaca tgccctgtaa ggccacagaa ctg                                   33

SEQ ID NO: 267          moltype = DNA   length = 33
FEATURE                 Location/Qualifiers
misc_feature            1..33
                        note = primer #54 (IL2_K48C_R)
source                  1..33
                        mol_type = other DNA
                        organism = synthetic construct
SEQUENCE: 267
cagttctgtg gccttacagg gcatgtaaaa ctt                                   33

SEQ ID NO: 268          moltype = DNA   length = 33
FEATURE                 Location/Qualifiers
misc_feature            1..33
                        note = primer #55 (IL2_K49C_F)
source                  1..33
                        mol_type = other DNA
                        organism = synthetic construct
SEQUENCE: 268
ttttacatgc ccaagtgtgc cacagaactg aaa                                   33

SEQ ID NO: 269          moltype = DNA   length = 33
FEATURE                 Location/Qualifiers
misc_feature            1..33
                        note = primer #56 (IL2_K49C_R)
source                  1..33
                        mol_type = other DNA
                        organism = synthetic construct
SEQUENCE: 269
tttcagttct gtggcacact tgggcatgta aaa                                   33

SEQ ID NO: 270          moltype = DNA   length = 33
FEATURE                 Location/Qualifiers
misc_feature            1..33
                        note = primer #57 (IL2_E61D_F)
source                  1..33
                        mol_type = other DNA
                        organism = synthetic construct
SEQUENCE: 270
cttcagtgtc tagaagacga actcaaacct ctg                                   33

SEQ ID NO: 271          moltype = DNA   length = 33
FEATURE                 Location/Qualifiers
misc_feature            1..33
                        note = primer #58 (IL2_E61D_R)
source                  1..33
                        mol_type = other DNA
                        organism = synthetic construct
SEQUENCE: 271
cagaggtttg agttcgtctt ctagacactg aag                                   33

SEQ ID NO: 272          moltype = DNA   length = 33
FEATURE                 Location/Qualifiers
misc_feature            1..33
                        note = primer #59 (IL2_E61Q_F)
source                  1..33
                        mol_type = other DNA
                        organism = synthetic construct
SEQUENCE: 272
cttcagtgtc tagaacaaga actcaaacct ctg                                   33

SEQ ID NO: 273          moltype = DNA   length = 33
FEATURE                 Location/Qualifiers
misc_feature            1..33
```

```
                        note        = primer #60 (IL2_E61Q_R)
source                  1..33
                        mol_type    = other DNA
                        organism    = synthetic construct
SEQUENCE: 273
cagaggtttg agttcttgtt ctagacactg aag                                        33

SEQ ID NO: 274          moltype = DNA   length = 30
FEATURE                 Location/Qualifiers
misc_feature            1..30
                        note        = primer #61 (IL2_E61R_F)
source                  1..30
                        mol_type    = other DNA
                        organism    = synthetic construct
SEQUENCE: 274
cttcagtgtc tagaacggga actcaaacct                                            30

SEQ ID NO: 275          moltype = DNA   length = 30
FEATURE                 Location/Qualifiers
misc_feature            1..30
                        note        = primer #62 (IL2_E61R_R)
source                  1..30
                        mol_type    = other DNA
                        organism    = synthetic construct
SEQUENCE: 275
aggtttgagt tcccgttcta gacactgaag                                            30

SEQ ID NO: 276          moltype = DNA   length = 33
FEATURE                 Location/Qualifiers
misc_feature            1..33
                        note        = primer #63 (IL2_E68D_F)
source                  1..33
                        mol_type    = other DNA
                        organism    = synthetic construct
SEQUENCE: 276
ctcaaacctc tggaggacgt gctaaattta gct                                        33

SEQ ID NO: 277          moltype = DNA   length = 33
FEATURE                 Location/Qualifiers
misc_feature            1..33
                        note        = primer #64 (IL2_E68D_R)
source                  1..33
                        mol_type    = other DNA
                        organism    = synthetic construct
SEQUENCE: 277
agctaaattt agcacgtcct ccagaggttt gag                                        33

SEQ ID NO: 278          moltype = DNA   length = 33
FEATURE                 Location/Qualifiers
misc_feature            1..33
                        note        = primer #65 (IL2_E68Q_F)
source                  1..33
                        mol_type    = other DNA
                        organism    = synthetic construct
SEQUENCE: 278
ctcaaacctc tggagcaggt gctaaattta gct                                        33

SEQ ID NO: 279          moltype = DNA   length = 33
FEATURE                 Location/Qualifiers
misc_feature            1..33
                        note        = primer #66 (IL2_E68Q_R)
source                  1..33
                        mol_type    = other DNA
                        organism    = synthetic construct
SEQUENCE: 279
agctaaattt agcacctgct ccagaggttt gag                                        33

SEQ ID NO: 280          moltype = DNA   length = 32
FEATURE                 Location/Qualifiers
misc_feature            1..32
                        note        = primer #67 (IL2_V69G_F)
source                  1..32
                        mol_type    = other DNA
                        organism    = synthetic construct
SEQUENCE: 280
caaacctctg gaggaagggc taaatttagc tc                                         32

SEQ ID NO: 281          moltype = DNA   length = 32
FEATURE                 Location/Qualifiers
```

```
misc_feature              1..32
                          note = primer #68 (IL2_V69G_R)
source                    1..32
                          mol_type = other DNA
                          organism = synthetic construct
SEQUENCE: 281
gagctaaatt tagcccttcc tccagaggtt tg                                       32

SEQ ID NO: 282            moltype = DNA  length = 40
FEATURE                   Location/Qualifiers
misc_feature              1..40
                          note = primer #69 (IL2_V69G_Q74A_F)
source                    1..40
                          mol_type = other DNA
                          organism = synthetic construct
SEQUENCE: 282
ctggaggaag ggctaaattt agctgcaagc aaaaactttc                                40

SEQ ID NO: 283            moltype = DNA  length = 40
FEATURE                   Location/Qualifiers
misc_feature              1..40
                          note = primer #70 (IL2_V69G_Q74A_R)
source                    1..40
                          mol_type = other DNA
                          organism = synthetic construct
SEQUENCE: 283
gaaagttttt gcttgcagct aaatttagcc cttcctccag                                40

SEQ ID NO: 284            moltype = DNA  length = 24
FEATURE                   Location/Qualifiers
misc_feature              1..24
                          note = primer #71 (IL2_Q74H_F)
source                    1..24
                          mol_type = other DNA
                          organism = synthetic construct
SEQUENCE: 284
ctaaatttag ctcacagcaa aaac                                                24

SEQ ID NO: 285            moltype = DNA  length = 24
FEATURE                   Location/Qualifiers
misc_feature              1..24
                          note = primer #72 (IL2_Q74H_R)
source                    1..24
                          mol_type = other DNA
                          organism = synthetic construct
SEQUENCE: 285
gtttttgctg tgagctaaat ttag                                                24

SEQ ID NO: 286            moltype = DNA  length = 33
FEATURE                   Location/Qualifiers
misc_feature              1..33
                          note = primer #73 (IL2_K76C_F)
source                    1..33
                          mol_type = other DNA
                          organism = synthetic construct
SEQUENCE: 286
aatttagctc aaagctgtaa ctttcactta aga                                      33

SEQ ID NO: 287            moltype = DNA  length = 33
FEATURE                   Location/Qualifiers
misc_feature              1..33
                          note = primer #74 (IL2_K76C_R)
source                    1..33
                          mol_type = other DNA
                          organism = synthetic construct
SEQUENCE: 287
tcttaagtga agttacagc tttgagctaa att                                       33

SEQ ID NO: 288            moltype = DNA  length = 32
FEATURE                   Location/Qualifiers
misc_feature              1..32
                          note = primer #75 (IL2_L80D_R81E_F)
source                    1..32
                          mol_type = other DNA
                          organism = synthetic construct
SEQUENCE: 288
aaagcaaaaa ctttcacgac gaacccaggg ac                                       32

SEQ ID NO: 289            moltype = DNA  length = 32
```

```
FEATURE                 Location/Qualifiers
misc_feature            1..32
                        note = primer #76 (IL2_L80D_R81E_R)
source                  1..32
                        mol_type = other DNA
                        organism = synthetic construct
SEQUENCE: 289
gtccctgggt tcgtcgtgaa agttttgct tt                                    32

SEQ ID NO: 290          moltype = DNA  length = 29
FEATURE                 Location/Qualifiers
misc_feature            1..29
                        note = primer #77 (IL2_L80F_F)
source                  1..29
                        mol_type = other DNA
                        organism = synthetic construct
SEQUENCE: 290
gcaaaaactt tcactttaga cccagggac                                       29

SEQ ID NO: 291          moltype = DNA  length = 29
FEATURE                 Location/Qualifiers
misc_feature            1..29
                        note = primer #78 (IL2_L80F_R)
source                  1..29
                        mol_type = other DNA
                        organism = synthetic construct
SEQUENCE: 291
gtccctgggt ctaaagtgaa agttttgc                                        29

SEQ ID NO: 292          moltype = DNA  length = 29
FEATURE                 Location/Qualifiers
misc_feature            1..29
                        note = primer #79 (IL2_L80F_R81D_F)
source                  1..29
                        mol_type = other DNA
                        organism = synthetic construct
SEQUENCE: 292
gcaaaaactt tcactttgac cccagggac                                       29

SEQ ID NO: 293          moltype = DNA  length = 29
FEATURE                 Location/Qualifiers
misc_feature            1..29
                        note = primer #80 (IL2_L80F_R81D_R)
source                  1..29
                        mol_type = other DNA
                        organism = synthetic construct
SEQUENCE: 293
gtccctgggg tcaaagtgaa agttttgc                                        29

SEQ ID NO: 294          moltype = DNA  length = 32
FEATURE                 Location/Qualifiers
misc_feature            1..32
                        note = primer #81 (IL2_L80F_R81E_F)
source                  1..32
                        mol_type = other DNA
                        organism = synthetic construct
SEQUENCE: 294
aaagcaaaaa ctttcacttc gaacccaggg ac                                   32

SEQ ID NO: 295          moltype = DNA  length = 32
FEATURE                 Location/Qualifiers
misc_feature            1..32
                        note = primer #82 (IL2_L80F_R81E_R)
source                  1..32
                        mol_type = other DNA
                        organism = synthetic construct
SEQUENCE: 295
gtccctgggt tcgaagtgaa agttttgct tt                                    32

SEQ ID NO: 296          moltype = DNA  length = 32
FEATURE                 Location/Qualifiers
misc_feature            1..32
                        note = primer #83 (IL2_L80V_R81D_F)
source                  1..32
                        mol_type = other DNA
                        organism = synthetic construct
SEQUENCE: 296
aaagcaaaaa ctttcacgtg gatcccaggg ac                                   32
```

```
SEQ ID NO: 297          moltype = DNA   length = 32
FEATURE                 Location/Qualifiers
misc_feature            1..32
                        note = primer #84 (IL2_L80V_R81D_R)
source                  1..32
                        mol_type = other DNA
                        organism = synthetic construct
SEQUENCE: 297
gtccctggga tccacgtgaa agttttttgct tt                                32

SEQ ID NO: 298          moltype = DNA   length = 32
FEATURE                 Location/Qualifiers
misc_feature            1..32
                        note = primer #85 (IL2_L80W_R81E_F)
source                  1..32
                        mol_type = other DNA
                        organism = synthetic construct
SEQUENCE: 298
aaagcaaaaa ctttcactgg gaacccaggg ac                                 32

SEQ ID NO: 299          moltype = DNA   length = 32
FEATURE                 Location/Qualifiers
misc_feature            1..32
                        note = primer #86 (IL2_L80W_R81E_R)
source                  1..32
                        mol_type = other DNA
                        organism = synthetic construct
SEQUENCE: 299
gtccctgggt tcccagtgaa agttttttgct tt                                32

SEQ ID NO: 300          moltype = DNA   length = 29
FEATURE                 Location/Qualifiers
misc_feature            1..29
                        note = primer #87 (IL2_L80Y_R81D_F)
source                  1..29
                        mol_type = other DNA
                        organism = synthetic construct
SEQUENCE: 300
gcaaaaactt tcactatgac cccagggac                                     29

SEQ ID NO: 301          moltype = DNA   length = 29
FEATURE                 Location/Qualifiers
misc_feature            1..29
                        note = primer #88 (IL2_L80Y_R81D_R)
source                  1..29
                        mol_type = other DNA
                        organism = synthetic construct
SEQUENCE: 301
gtccctgggg tcatagtgaa agtttttgc                                     29

SEQ ID NO: 302          moltype = DNA   length = 32
FEATURE                 Location/Qualifiers
misc_feature            1..32
                        note = primer #89 (IL2_L80Y_R81E_F)
source                  1..32
                        mol_type = other DNA
                        organism = synthetic construct
SEQUENCE: 302
aaagcaaaaa ctttcactac gaacccaggg ac                                 32

SEQ ID NO: 303          moltype = DNA   length = 32
FEATURE                 Location/Qualifiers
misc_feature            1..32
                        note = primer #90 (IL2_L80Y_R81E_R)
source                  1..32
                        mol_type = other DNA
                        organism = synthetic construct
SEQUENCE: 303
gtccctgggt tcgtagtgaa agttttttgct tt                                32

SEQ ID NO: 304          moltype = DNA   length = 32
FEATURE                 Location/Qualifiers
misc_feature            1..32
                        note = primer #91 (IL2_L80Y_R81N_F)
source                  1..32
                        mol_type = other DNA
                        organism = synthetic construct
SEQUENCE: 304
aaagcaaaaa ctttcactac aacccaggg ac                                  32
```

```
SEQ ID NO: 305           moltype = DNA   length = 32
FEATURE                  Location/Qualifiers
misc_feature             1..32
                         note = primer #92 (IL2_L80Y_R81N_R)
source                   1..32
                         mol_type = other DNA
                         organism = synthetic construct
SEQUENCE: 305
gtccctgggg ttgtagtgaa agttttttgct tt                                       32

SEQ ID NO: 306           moltype = DNA   length = 29
FEATURE                  Location/Qualifiers
misc_feature             1..29
                         note = primer #93 (IL2_L80Y_R81R_F)
source                   1..29
                         mol_type = other DNA
                         organism = synthetic construct
SEQUENCE: 306
gcaaaaactt tcactataga cccagggac                                            29

SEQ ID NO: 307           moltype = DNA   length = 29
FEATURE                  Location/Qualifiers
misc_feature             1..29
                         note = primer #94 (IL2_L80Y_R81R_R)
source                   1..29
                         mol_type = other DNA
                         organism = synthetic construct
SEQUENCE: 307
gtccctgggt ctatagtgaa agttttttgc                                           29

SEQ ID NO: 308           moltype = DNA   length = 31
FEATURE                  Location/Qualifiers
misc_feature             1..31
                         note = primer #95 (IL2_R81D_D84E_F)
source                   1..31
                         mol_type = other DNA
                         organism = synthetic construct
SEQUENCE: 308
ctttcactta gaccccaggg agttaatcag c                                         31

SEQ ID NO: 309           moltype = DNA   length = 31
FEATURE                  Location/Qualifiers
misc_feature             1..31
                         note = primer #96 (IL2_R81D_D84E_R)
source                   1..31
                         mol_type = other DNA
                         organism = synthetic construct
SEQUENCE: 309
gctgattaac tccctggggt ctaagtgaaa g                                         31

SEQ ID NO: 310           moltype = DNA   length = 34
FEATURE                  Location/Qualifiers
misc_feature             1..34
                         note = primer #97 (IL2_R81D_F)
source                   1..34
                         mol_type = other DNA
                         organism = synthetic construct
SEQUENCE: 310
caaaaacttt cacttagacc ccagggactt aatc                                      34

SEQ ID NO: 311           moltype = DNA   length = 34
FEATURE                  Location/Qualifiers
misc_feature             1..34
                         note = primer #98 (IL2_R81D_R)
source                   1..34
                         mol_type = other DNA
                         organism = synthetic construct
SEQUENCE: 311
gattaagtcc ctggggtcta agtgaaagtt tttg                                      34

SEQ ID NO: 312           moltype = DNA   length = 51
FEATURE                  Location/Qualifiers
misc_feature             1..51
                         note = primer #99 (IL2_R81D_F_long)
source                   1..51
                         mol_type = other DNA
                         organism = synthetic construct
SEQUENCE: 312
```

```
ctcaaagcaa aaactttcac ttagacccca gggacttaat cagcaaatat c          51

SEQ ID NO: 313          moltype = DNA   length = 51
FEATURE                 Location/Qualifiers
misc_feature            1..51
                        note = primer #100 (IL2_R81D_R_long)
source                  1..51
                        mol_type = other DNA
                        organism = synthetic construct
SEQUENCE: 313
gatatttgct gattaagtcc ctgggtcta agtgaaagtt tttgctttga g           51

SEQ ID NO: 314          moltype = DNA   length = 43
FEATURE                 Location/Qualifiers
misc_feature            1..43
                        note = primer #101 (IL2_R81E_D84E_L85V_I86V_V91T_I92F_F)
source                  1..43
                        mol_type = other DNA
                        organism = synthetic construct
SEQUENCE: 314
gaacccaggg aggtagtcag caatatcaac acatttgttc tgg                   43

SEQ ID NO: 315          moltype = DNA   length = 43
FEATURE                 Location/Qualifiers
misc_feature            1..43
                        note = primer #102 (IL2_R81E_D84E_L85V_I86V_V91T_I92F_R)
source                  1..43
                        mol_type = other DNA
                        organism = synthetic construct
SEQUENCE: 315
ccagaacaaa tgtgttgata ttgctgacta cctccctggg ttc                   43

SEQ ID NO: 316          moltype = DNA   length = 31
FEATURE                 Location/Qualifiers
misc_feature            1..31
                        note = primer #103 (IL2_R81E_F)
source                  1..31
                        mol_type = other DNA
                        organism = synthetic construct
SEQUENCE: 316
aaactttcac ttagaaccca gggacttaat c                                31

SEQ ID NO: 317          moltype = DNA   length = 31
FEATURE                 Location/Qualifiers
misc_feature            1..31
                        note = primer #104 (IL2_R81E_R)
source                  1..31
                        mol_type = other DNA
                        organism = synthetic construct
SEQUENCE: 317
gattaagtcc ctgggttcta agtgaaagtt t                                31

SEQ ID NO: 318          moltype = DNA   length = 33
FEATURE                 Location/Qualifiers
misc_feature            1..33
                        note = primer #105 (IL2_P82G_F)
source                  1..33
                        mol_type = other DNA
                        organism = synthetic construct
SEQUENCE: 318
aactttcact tcgaaggcag ggacgtagtc agc                              33

SEQ ID NO: 319          moltype = DNA   length = 33
FEATURE                 Location/Qualifiers
misc_feature            1..33
                        note = primer #106 (IL2_P82G_R)
source                  1..33
                        mol_type = other DNA
                        organism = synthetic construct
SEQUENCE: 319
gctgactacg tccctgcctt cgaagtgaaa gtt                              33

SEQ ID NO: 320          moltype = DNA   length = 33
FEATURE                 Location/Qualifiers
misc_feature            1..33
                        note = primer #107 (IL2_P82V_F)
source                  1..33
                        mol_type = other DNA
                        organism = synthetic construct
```

```
SEQUENCE: 320
aactttcact tcgaagtcag ggacgtagtc agc                                  33

SEQ ID NO: 321          moltype = DNA   length = 33
FEATURE                 Location/Qualifiers
misc_feature            1..33
                        note = primer #108 (IL2_P82V_R)
source                  1..33
                        mol_type = other DNA
                        organism = synthetic construct
SEQUENCE: 321
gctgactacg tccctgactt cgaagtgaaa gtt                                  33

SEQ ID NO: 322          moltype = DNA   length = 34
FEATURE                 Location/Qualifiers
misc_feature            1..34
                        note = primer #109 (IL2_D84E_F)
source                  1..34
                        mol_type = other DNA
                        organism = synthetic construct
SEQUENCE: 322
cttaagaccc agggagttaa tcagcaatat caac                                 34

SEQ ID NO: 323          moltype = DNA   length = 34
FEATURE                 Location/Qualifiers
misc_feature            1..34
                        note = primer #110 (IL2_D84E_R)
source                  1..34
                        mol_type = other DNA
                        organism = synthetic construct
SEQUENCE: 323
gttgatattg ctgattaact ccctgggtct taag                                 34

SEQ ID NO: 324          moltype = DNA   length = 32
FEATURE                 Location/Qualifiers
misc_feature            1..32
                        note = primer #111 (IL2_D84F_F)
source                  1..32
                        mol_type = other DNA
                        organism = synthetic construct
SEQUENCE: 324
cacttagacc ccaggttctt aatcagcaat at                                   32

SEQ ID NO: 325          moltype = DNA   length = 32
FEATURE                 Location/Qualifiers
misc_feature            1..32
                        note = primer #112 (IL2_D84F_R)
source                  1..32
                        mol_type = other DNA
                        organism = synthetic construct
SEQUENCE: 325
atattgctga ttaagaacct ggggtctaag tg                                   32

SEQ ID NO: 326          moltype = DNA   length = 31
FEATURE                 Location/Qualifiers
misc_feature            1..31
                        note = primer #113 (IL2_D84V_F)
source                  1..31
                        mol_type = other DNA
                        organism = synthetic construct
SEQUENCE: 326
acttagaccc cagggtctta atcagcaata t                                    31

SEQ ID NO: 327          moltype = DNA   length = 31
FEATURE                 Location/Qualifiers
misc_feature            1..31
                        note = primer #114 (IL2_D84V_R)
source                  1..31
                        mol_type = other DNA
                        organism = synthetic construct
SEQUENCE: 327
atattgctga ttaagaccct ggggtctaag t                                    31

SEQ ID NO: 328          moltype = DNA   length = 35
FEATURE                 Location/Qualifiers
misc_feature            1..35
                        note = primer #115 (IL2_L85A_I86A_F)
source                  1..35
                        mol_type = other DNA
```

```
                        organism = synthetic construct
SEQUENCE: 328
ctttgacccc agggacgctg ccagcaatat caacg                               35

SEQ ID NO: 329          moltype = DNA  length = 35
FEATURE                 Location/Qualifiers
misc_feature            1..35
                        note = primer #116 (IL2_L85A_I86A_R)
source                  1..35
                        mol_type = other DNA
                        organism = synthetic construct
SEQUENCE: 329
cgttgatatt gctggcagcg tccctggggt caaag                               35

SEQ ID NO: 330          moltype = DNA  length = 30
FEATURE                 Location/Qualifiers
misc_feature            1..30
                        note = primer #117 (IL2_L85E_I86V_F)
source                  1..30
                        mol_type = other DNA
                        organism = synthetic construct
SEQUENCE: 330
cccagggacg aagtgagcaa tatcaacgta                                     30

SEQ ID NO: 331          moltype = DNA  length = 30
FEATURE                 Location/Qualifiers
misc_feature            1..30
                        note = primer #118 (IL2_L85E_I86V_R)
source                  1..30
                        mol_type = other DNA
                        organism = synthetic construct
SEQUENCE: 331
tacgttgata ttgctcactt cgtccctggg                                     30

SEQ ID NO: 332          moltype = DNA  length = 27
FEATURE                 Location/Qualifiers
misc_feature            1..27
                        note = primer #119 (IL2_L85F_I86L_F)
source                  1..27
                        mol_type = other DNA
                        organism = synthetic construct
SEQUENCE: 332
cccagggact tcctcagcaa tatcaac                                        27

SEQ ID NO: 333          moltype = DNA  length = 27
FEATURE                 Location/Qualifiers
misc_feature            1..27
                        note = primer #120 (IL2_L85F_I86L_R)
source                  1..27
                        mol_type = other DNA
                        organism = synthetic construct
SEQUENCE: 333
gttgatattg ctgaggaagt ccctggg                                        27

SEQ ID NO: 334          moltype = DNA  length = 27
FEATURE                 Location/Qualifiers
misc_feature            1..27
                        note = primer #121 (IL2_L85F_I86V_F)
source                  1..27
                        mol_type = other DNA
                        organism = synthetic construct
SEQUENCE: 334
cccagggact tcgtcagcaa tatcaac                                        27

SEQ ID NO: 335          moltype = DNA  length = 27
FEATURE                 Location/Qualifiers
misc_feature            1..27
                        note = primer #122 (IL2_L85F_I86V_R)
source                  1..27
                        mol_type = other DNA
                        organism = synthetic construct
SEQUENCE: 335
gttgatattg ctgacgaagt ccctggg                                        27

SEQ ID NO: 336          moltype = DNA  length = 27
FEATURE                 Location/Qualifiers
misc_feature            1..27
                        note = primer #123 (IL2_L85G_I86A_F)
source                  1..27
```

```
                                    mol_type = other DNA
                                    organism = synthetic construct
SEQUENCE: 336
cccaggacg gagccagcaa tatcaac                                              27

SEQ ID NO: 337           moltype = DNA   length = 27
FEATURE                  Location/Qualifiers
misc_feature             1..27
                         note = primer #124 (IL2_L85G_I86A_R)
source                   1..27
                         mol_type = other DNA
                         organism = synthetic construct
SEQUENCE: 337
gttgatattg ctggctccgt ccctggg                                             27

SEQ ID NO: 338           moltype = DNA   length = 35
FEATURE                  Location/Qualifiers
misc_feature             1..35
                         note = primer #125 (IL2_L85G_I86V_F)
source                   1..35
                         mol_type = other DNA
                         organism = synthetic construct
SEQUENCE: 338
ctttgacccc agggacggtg ttagcaatat caacg                                    35

SEQ ID NO: 339           moltype = DNA   length = 35
FEATURE                  Location/Qualifiers
misc_feature             1..35
                         note = primer #126 (IL2_L85G_I86V_R)
source                   1..35
                         mol_type = other DNA
                         organism = synthetic construct
SEQUENCE: 339
cgttgatatt gctaacccag tccctggggt caaag                                    35

SEQ ID NO: 340           moltype = DNA   length = 27
FEATURE                  Location/Qualifiers
misc_feature             1..27
                         note = primer #127 (IL2_L85I_I86V_F)
source                   1..27
                         mol_type = other DNA
                         organism = synthetic construct
SEQUENCE: 340
cccagggaca tagtcagcaa tatcaac                                             27

SEQ ID NO: 341           moltype = DNA   length = 27
FEATURE                  Location/Qualifiers
misc_feature             1..27
                         note = primer #128 (IL2_L85I_I86V_R)
source                   1..27
                         mol_type = other DNA
                         organism = synthetic construct
SEQUENCE: 341
gttgatattg ctgactatgt ccctggg                                             27

SEQ ID NO: 342           moltype = DNA   length = 34
FEATURE                  Location/Qualifiers
misc_feature             1..34
                         note = primer #129 (IL2_L85L_I86A_F)
source                   1..34
                         mol_type = other DNA
                         organism = synthetic construct
SEQUENCE: 342
cttcgaaccc agggacctgg ccagcaatat caac                                     34

SEQ ID NO: 343           moltype = DNA   length = 34
FEATURE                  Location/Qualifiers
misc_feature             1..34
                         note = primer #130 (IL2_L85L_I86A_R)
source                   1..34
                         mol_type = other DNA
                         organism = synthetic construct
SEQUENCE: 343
gttgatattg ctggccaggt ccctgggttc gaag                                     34

SEQ ID NO: 344           moltype = DNA   length = 34
FEATURE                  Location/Qualifiers
misc_feature             1..34
                         note = primer #131 (IL2_L85L_I86V_F)
```

```
source                   1..34
                         mol_type = other DNA
                         organism = synthetic construct
SEQUENCE: 344
ctttgagccc agggacttag tcagcaatat caac                               34

SEQ ID NO: 345           moltype = DNA  length = 34
FEATURE                  Location/Qualifiers
misc_feature             1..34
                         note = primer #132 (IL2_L85L_I86V_R)
source                   1..34
                         mol_type = other DNA
                         organism = synthetic construct
SEQUENCE: 345
gttgatattg ctgactaagt ccctgggctc aaag                               34

SEQ ID NO: 346           moltype = DNA  length = 27
FEATURE                  Location/Qualifiers
misc_feature             1..27
                         note = primer #133 (IL2_L85T_I86G_F)
source                   1..27
                         mol_type = other DNA
                         organism = synthetic construct
SEQUENCE: 346
cccagggaca caggcagcaa tatcaac                                       27

SEQ ID NO: 347           moltype = DNA  length = 27
FEATURE                  Location/Qualifiers
misc_feature             1..27
                         note = primer #134 (IL2_L85T_I86G_R)
source                   1..27
                         mol_type = other DNA
                         organism = synthetic construct
SEQUENCE: 347
gttgatattg ctgcctgtgt ccctggg                                       27

SEQ ID NO: 348           moltype = DNA  length = 29
FEATURE                  Location/Qualifiers
misc_feature             1..29
                         note = primer #135 (IL2_L85V_I86G_F)
source                   1..29
                         mol_type = other DNA
                         organism = synthetic construct
SEQUENCE: 348
cccagggacg taggcagcaa tatcaacgt                                     29

SEQ ID NO: 349           moltype = DNA  length = 29
FEATURE                  Location/Qualifiers
misc_feature             1..29
                         note = primer #136 (IL2_L85V_I86G_R)
source                   1..29
                         mol_type = other DNA
                         organism = synthetic construct
SEQUENCE: 349
acgttgatat tgctgcctac gtccctggg                                     29

SEQ ID NO: 350           moltype = DNA  length = 31
FEATURE                  Location/Qualifiers
misc_feature             1..31
                         note = primer #137 (IL2_L85V_I86I_codon_F)
source                   1..31
                         mol_type = other DNA
                         organism = synthetic construct
SEQUENCE: 350
gaacccaggg acgtaatcag caatatcaac g                                  31

SEQ ID NO: 351           moltype = DNA  length = 31
FEATURE                  Location/Qualifiers
misc_feature             1..31
                         note = primer #138 (IL2_L85V_I86I_codon_R)
source                   1..31
                         mol_type = other DNA
                         organism = synthetic construct
SEQUENCE: 351
cgttgatatt gctgattacg tccctgggtt c                                  31

SEQ ID NO: 352           moltype = DNA  length = 30
FEATURE                  Location/Qualifiers
misc_feature             1..30
```

```
                    note        = primer #139 (IL2_L85V_I86V_F)
source              1..30
                    mol_type    = other DNA
                    organism    = synthetic construct
SEQUENCE: 352
gacccaggga cgtagtcagc aatatcaacg                                     30

SEQ ID NO: 353      moltype = DNA   length = 30
FEATURE             Location/Qualifiers
misc_feature        1..30
                    note        = primer #140 (IL2_L85V_I86V_R)
source              1..30
                    mol_type    = other DNA
                    organism    = synthetic construct
SEQUENCE: 353
cgttgatatt gctgactacg tccctgggtc                                     30

SEQ ID NO: 354      moltype = DNA   length = 29
FEATURE             Location/Qualifiers
misc_feature        1..29
                    note        = primer #141 (IL2_L85W_I86V_F)
source              1..29
                    mol_type    = other DNA
                    organism    = synthetic construct
SEQUENCE: 354
cccagggact gggtcagcaa tatcaacgt                                      29

SEQ ID NO: 355      moltype = DNA   length = 29
FEATURE             Location/Qualifiers
misc_feature        1..29
                    note        = primer #142 (IL2_L85W_I86V_R)
source              1..29
                    mol_type    = other DNA
                    organism    = synthetic construct
SEQUENCE: 355
acgttgatat tgctgaccca gtccctggg                                      29

SEQ ID NO: 356      moltype = DNA   length = 30
FEATURE             Location/Qualifiers
misc_feature        1..30
                    note        = primer #143 (IL2_L85W_I86V_Long_F)
source              1..30
                    mol_type    = other DNA
                    organism    = synthetic construct
SEQUENCE: 356
tttgacccca gggactgggt cagcaatatc                                     30

SEQ ID NO: 357      moltype = DNA   length = 30
FEATURE             Location/Qualifiers
misc_feature        1..30
                    note        = primer #144 (IL2_L85W_I86V_Long_R)
source              1..30
                    mol_type    = other DNA
                    organism    = synthetic construct
SEQUENCE: 357
gatattgctg acccagtccc tggggtcaaa                                     30

SEQ ID NO: 358      moltype = DNA   length = 34
FEATURE             Location/Qualifiers
misc_feature        1..34
                    note        = primer #145 (IL2_L85Y_I86V_F)
source              1..34
                    mol_type    = other DNA
                    organism    = synthetic construct
SEQUENCE: 358
cttcgaaccc agggactacg tcagcaatat caac                                34

SEQ ID NO: 359      moltype = DNA   length = 34
FEATURE             Location/Qualifiers
misc_feature        1..34
                    note        = primer #146 (IL2_L85Y_I86V_R)
source              1..34
                    mol_type    = other DNA
                    organism    = synthetic construct
SEQUENCE: 359
gttgatattg ctgacgtagt ccctgggttc gaag                                34

SEQ ID NO: 360      moltype = DNA   length = 31
FEATURE             Location/Qualifiers
```

```
misc_feature           1..31
                       note = primer #147 (IL2_I86V_V91T_I92F_F)
source                 1..31
                       mol_type = other DNA
                       organism = synthetic construct
SEQUENCE: 360
gtcagcaata tcaacacatt tgttctggaa c                                  31

SEQ ID NO: 361         moltype = DNA  length = 31
FEATURE                Location/Qualifiers
misc_feature           1..31
                       note = primer #148 (IL2_I86V_V91T_I92F_R)
source                 1..31
                       mol_type = other DNA
                       organism = synthetic construct
SEQUENCE: 361
gttccagaac aaatgtgttg atattgctga c                                  31

SEQ ID NO: 362         moltype = DNA  length = 33
FEATURE                Location/Qualifiers
misc_feature           1..33
                       note = primer #149 (IL2_S87C_F)
source                 1..33
                       mol_type = other DNA
                       organism = synthetic construct
SEQUENCE: 362
cccagggact taatctgcaa tatcaacgta ata                                33

SEQ ID NO: 363         moltype = DNA  length = 33
FEATURE                Location/Qualifiers
misc_feature           1..33
                       note = primer #150 (IL2_S87C_R)
source                 1..33
                       mol_type = other DNA
                       organism = synthetic construct
SEQUENCE: 363
tattacgttg atattgcaga ttaagtccct ggg                                33

SEQ ID NO: 364         moltype = DNA  length = 34
FEATURE                Location/Qualifiers
misc_feature           1..34
                       note = primer #151 (IL2_N88F_F)
source                 1..34
                       mol_type = other DNA
                       organism = synthetic construct
SEQUENCE: 364
cagggactta atcagcttta tcaacgtatt tgtt                               34

SEQ ID NO: 365         moltype = DNA  length = 34
FEATURE                Location/Qualifiers
misc_feature           1..34
                       note = primer #152 (IL2_N88F_R)
source                 1..34
                       mol_type = other DNA
                       organism = synthetic construct
SEQUENCE: 365
aacaaatacg ttgataaagc tgattaagtc cctg                               34

SEQ ID NO: 366         moltype = DNA  length = 33
FEATURE                Location/Qualifiers
misc_feature           1..33
                       note = primer #153 (IL2_N88Q_F)
source                 1..33
                       mol_type = other DNA
                       organism = synthetic construct
SEQUENCE: 366
gggacttaat cagccaaatc aacgtaatag ttc                                33

SEQ ID NO: 367         moltype = DNA  length = 33
FEATURE                Location/Qualifiers
misc_feature           1..33
                       note = primer #154 (IL2_N88Q_R)
source                 1..33
                       mol_type = other DNA
                       organism = synthetic construct
SEQUENCE: 367
gaactattac gttgatttgg ctgattaagt ccc                                33

SEQ ID NO: 368         moltype = DNA  length = 34
```

```
FEATURE                 Location/Qualifiers
misc_feature            1..34
                        note = primer #155 (IL2_N88V_F)
source                  1..34
                        mol_type = other DNA
                        organism = synthetic construct
SEQUENCE: 368
cagggactta atcagcgtta tcaacgtatt tgtt                                34

SEQ ID NO: 369          moltype = DNA  length = 34
FEATURE                 Location/Qualifiers
misc_feature            1..34
                        note = primer #156 (IL2_N88V_R)
source                  1..34
                        mol_type = other DNA
                        organism = synthetic construct
SEQUENCE: 369
aacaaatacg ttgataacgc tgattaagtc cctg                                34

SEQ ID NO: 370          moltype = DNA  length = 33
FEATURE                 Location/Qualifiers
misc_feature            1..33
                        note = primer #157 (IL2_I89F_F)
source                  1..33
                        mol_type = other DNA
                        organism = synthetic construct
SEQUENCE: 370
gacttaatca gcaatttcaa cgtaatagtt ctg                                 33

SEQ ID NO: 371          moltype = DNA  length = 33
FEATURE                 Location/Qualifiers
misc_feature            1..33
                        note = primer #158 (IL2_I89F_R)
source                  1..33
                        mol_type = other DNA
                        organism = synthetic construct
SEQUENCE: 371
cagaactatt acgttgaaat tgctgattaa gtc                                 33

SEQ ID NO: 372          moltype = DNA  length = 33
FEATURE                 Location/Qualifiers
misc_feature            1..33
                        note = primer #159 (IL2_V91E_I92F_F)
source                  1..33
                        mol_type = other DNA
                        organism = synthetic construct
SEQUENCE: 372
agcaatatca acgaattcgt tctggaacta aag                                 33

SEQ ID NO: 373          moltype = DNA  length = 33
FEATURE                 Location/Qualifiers
misc_feature            1..33
                        note = primer #160 (IL2_V91E_I92F_R)
source                  1..33
                        mol_type = other DNA
                        organism = synthetic construct
SEQUENCE: 373
ctttagttcc agaacgaatt cgttgatatt gct                                 33

SEQ ID NO: 374          moltype = DNA  length = 33
FEATURE                 Location/Qualifiers
misc_feature            1..33
                        note = primer #161 (IL2_V91E_I92W_F)
source                  1..33
                        mol_type = other DNA
                        organism = synthetic construct
SEQUENCE: 374
agcaatatca acgaatgggt tctggaacta aag                                 33

SEQ ID NO: 375          moltype = DNA  length = 33
FEATURE                 Location/Qualifiers
misc_feature            1..33
                        note = primer #162 (IL2_V91E_I92W_R)
source                  1..33
                        mol_type = other DNA
                        organism = synthetic construct
SEQUENCE: 375
ctttagttcc agaacccatt cgttgatatt gct                                 33
```

```
SEQ ID NO: 376          moltype = DNA   length = 34
FEATURE                 Location/Qualifiers
misc_feature            1..34
                        note = primer #163 (IL2_V91F_F)
source                  1..34
                        mol_type = other DNA
                        organism = synthetic construct
SEQUENCE: 376
cagcaatatc aactttatag ttctggaact aaag                                34

SEQ ID NO: 377          moltype = DNA   length = 34
FEATURE                 Location/Qualifiers
misc_feature            1..34
                        note = primer #164 (IL2_V91F_R)
source                  1..34
                        mol_type = other DNA
                        organism = synthetic construct
SEQUENCE: 377
ctttagttcc agaactataa agttgatatt gctg                                34

SEQ ID NO: 378          moltype = DNA   length = 34
FEATURE                 Location/Qualifiers
misc_feature            1..34
                        note = primer #165 (IL2_V91T_F)
source                  1..34
                        mol_type = other DNA
                        organism = synthetic construct
SEQUENCE: 378
cagcaatatc aacacaatag ttctggaact aaag                                34

SEQ ID NO: 379          moltype = DNA   length = 34
FEATURE                 Location/Qualifiers
misc_feature            1..34
                        note = primer #166 (IL2_V91T_R)
source                  1..34
                        mol_type = other DNA
                        organism = synthetic construct
SEQUENCE: 379
ctttagttcc agaactattg tgttgatatt gctg                                34

SEQ ID NO: 380          moltype = DNA   length = 32
FEATURE                 Location/Qualifiers
misc_feature            1..32
                        note = primer #167 (IL2_I92F_F)
source                  1..32
                        mol_type = other DNA
                        organism = synthetic construct
SEQUENCE: 380
gcaatatcaa cgtatttgtt ctggaactaa ag                                  32

SEQ ID NO: 381          moltype = DNA   length = 32
FEATURE                 Location/Qualifiers
misc_feature            1..32
                        note = primer #168 (IL2_I92F_R)
source                  1..32
                        mol_type = other DNA
                        organism = synthetic construct
SEQUENCE: 381
ctttagttcc agaacaaata cgttgatatt gc                                  32

SEQ ID NO: 382          moltype = DNA   length = 49
FEATURE                 Location/Qualifiers
misc_feature            1..49
                        note = primer #169 (IL2_I92F_F_long)
source                  1..49
                        mol_type = other DNA
                        organism = synthetic construct
SEQUENCE: 382
gacttaatca gcaatatcaa cgtatttgtt ctggaactaa agggatctg                49

SEQ ID NO: 383          moltype = DNA   length = 49
FEATURE                 Location/Qualifiers
misc_feature            1..49
                        note = primer #170 (IL2_I92F_R_long)
source                  1..49
                        mol_type = other DNA
                        organism = synthetic construct
SEQUENCE: 383
cagatccctt tagttccaga acaaatacgt tgatattgct gattaagtc                49
```

```
SEQ ID NO: 384          moltype = DNA  length = 45
FEATURE                 Location/Qualifiers
misc_feature            1..45
                        note = primer #171 (IL2_I92F_F_long2)
source                  1..45
                        mol_type = other DNA
                        organism = synthetic construct
SEQUENCE: 384
cttaatcagc aatatcaacg tatttgttct ggaactaaag ggatc              45

SEQ ID NO: 385          moltype = DNA  length = 45
FEATURE                 Location/Qualifiers
misc_feature            1..45
                        note = primer #172 (IL2_I92F_R_long2)
source                  1..45
                        mol_type = other DNA
                        organism = synthetic construct
SEQUENCE: 385
gatcccttta gttccagaac aaatacgttg atattgctga ttaag              45

SEQ ID NO: 386          moltype = DNA  length = 32
FEATURE                 Location/Qualifiers
misc_feature            1..32
                        note = primer #173 (IL2_I92F_L94F_L96F_F)
source                  1..32
                        mol_type = other DNA
                        organism = synthetic construct
SEQUENCE: 386
caacgtattt gttttcgaat tcaagggatc tg                            32

SEQ ID NO: 387          moltype = DNA  length = 32
FEATURE                 Location/Qualifiers
misc_feature            1..32
                        note = primer #174 (IL2_I92F_L94F_L96F_R)
source                  1..32
                        mol_type = other DNA
                        organism = synthetic construct
SEQUENCE: 387
cagatccctt gaattcgaaa acaaatacgt tg                            32

SEQ ID NO: 388          moltype = DNA  length = 39
FEATURE                 Location/Qualifiers
misc_feature            1..39
                        note = primer #175 (IL2_I92F_L94F_L96F_F)
source                  1..39
                        mol_type = other DNA
                        organism = synthetic construct
SEQUENCE: 388
gcaatatcaa cgtatttgtt ttcgaattta agggatctg                     39

SEQ ID NO: 389          moltype = DNA  length = 39
FEATURE                 Location/Qualifiers
misc_feature            1..39
                        note = primer #176 (IL2_I92F_L94F_L96F_R)
source                  1..39
                        mol_type = other DNA
                        organism = synthetic construct
SEQUENCE: 389
cagatccctt aaattcgaaa acaaatacgt tgatattgc                     39

SEQ ID NO: 390          moltype = DNA  length = 39
FEATURE                 Location/Qualifiers
misc_feature            1..39
                        note = primer #177 (IL2_I92F_L94F_L96I_F)
source                  1..39
                        mol_type = other DNA
                        organism = synthetic construct
SEQUENCE: 390
gcaatatcaa cgtatttgtt ttcgaaatta agggatctg                     39

SEQ ID NO: 391          moltype = DNA  length = 39
FEATURE                 Location/Qualifiers
misc_feature            1..39
                        note = primer #178 (IL2_I92F_L94F_L96I_R)
source                  1..39
                        mol_type = other DNA
                        organism = synthetic construct
SEQUENCE: 391
```

```
cagatccctt aatttcgaaa acaaatacgt tgatattgc                              39

SEQ ID NO: 392          moltype = DNA   length = 39
FEATURE                 Location/Qualifiers
misc_feature            1..39
                        note = primer #179 (IL2_I92F_L94F_L96V_F)
source                  1..39
                        mol_type = other DNA
                        organism = synthetic construct
SEQUENCE: 392
gcaatatcaa cgtatttgtt ttcgaagtaa agggatctg                              39

SEQ ID NO: 393          moltype = DNA   length = 39
FEATURE                 Location/Qualifiers
misc_feature            1..39
                        note = primer #180 (IL2_I92F_L94F_L96V_R)
source                  1..39
                        mol_type = other DNA
                        organism = synthetic construct
SEQUENCE: 393
cagatccctt tacttcgaaa acaaatacgt tgatattgc                              39

SEQ ID NO: 394          moltype = DNA   length = 33
FEATURE                 Location/Qualifiers
misc_feature            1..33
                        note = primer #181 (IL2_I92I_F)
source                  1..33
                        mol_type = other DNA
                        organism = synthetic construct
SEQUENCE: 394
gcaatatcaa cgtaattgtt ctggaactaa agg                                    33

SEQ ID NO: 395          moltype = DNA   length = 33
FEATURE                 Location/Qualifiers
misc_feature            1..33
                        note = primer #182 (IL2_I92I_R)
source                  1..33
                        mol_type = other DNA
                        organism = synthetic construct
SEQUENCE: 395
cctttagttc cagaacaatt acgttgatat tgc                                    33

SEQ ID NO: 396          moltype = DNA   length = 33
FEATURE                 Location/Qualifiers
misc_feature            1..33
                        note = primer #183 (IL2_I92L_F)
source                  1..33
                        mol_type = other DNA
                        organism = synthetic construct
SEQUENCE: 396
gcaatatcaa cgtattagtt ctggaactaa agg                                    33

SEQ ID NO: 397          moltype = DNA   length = 33
FEATURE                 Location/Qualifiers
misc_feature            1..33
                        note = primer #184 (IL2_I92L_R)
source                  1..33
                        mol_type = other DNA
                        organism = synthetic construct
SEQUENCE: 397
cctttagttc cagaactaat acgttgatat tgc                                    33

SEQ ID NO: 398          moltype = DNA   length = 33
FEATURE                 Location/Qualifiers
misc_feature            1..33
                        note = primer #185 (IL2_I92W_F)
source                  1..33
                        mol_type = other DNA
                        organism = synthetic construct
SEQUENCE: 398
agcaatatca acgtatgggt tctggaacta aag                                    33

SEQ ID NO: 399          moltype = DNA   length = 33
FEATURE                 Location/Qualifiers
misc_feature            1..33
                        note = primer #186 (IL2_I92W_R)
source                  1..33
                        mol_type = other DNA
                        organism = synthetic construct
```

```
SEQUENCE: 399
ctttagttcc agaacccata cgttgatatt gct                                       33

SEQ ID NO: 400              moltype = DNA   length = 32
FEATURE                     Location/Qualifiers
misc_feature                1..32
                            note = primer #187 (IL2_I92Y_F)
source                      1..32
                            mol_type = other DNA
                            organism = synthetic construct
SEQUENCE: 400
gcaatatcaa cgtatatgtt ctggaactaa ag                                        32

SEQ ID NO: 401              moltype = DNA   length = 32
FEATURE                     Location/Qualifiers
misc_feature                1..32
                            note = primer #188 (IL2_I92Y_R)
source                      1..32
                            mol_type = other DNA
                            organism = synthetic construct
SEQUENCE: 401
ctttagttcc agaacatata cgttgatatt gc                                        32

SEQ ID NO: 402              moltype = DNA   length = 33
FEATURE                     Location/Qualifiers
misc_feature                1..33
                            note = primer #189 (IL2_L94F_L96F_F)
source                      1..33
                            mol_type = other DNA
                            organism = synthetic construct
SEQUENCE: 402
cgtaatagtt ttcgaattta agggatctga aac                                       33

SEQ ID NO: 403              moltype = DNA   length = 33
FEATURE                     Location/Qualifiers
misc_feature                1..33
                            note = primer #190 (IL2_L94F_L96F_R)
source                      1..33
                            mol_type = other DNA
                            organism = synthetic construct
SEQUENCE: 403
gtttcagatc ccttaaattc gaaaactatt acg                                       33

SEQ ID NO: 404              moltype = DNA   length = 33
FEATURE                     Location/Qualifiers
misc_feature                1..33
                            note = primer #191 (IL2_L94F_L96I_F)
source                      1..33
                            mol_type = other DNA
                            organism = synthetic construct
SEQUENCE: 404
cgtaatagtt ttcgaaatta agggatctga aac                                       33

SEQ ID NO: 405              moltype = DNA   length = 33
FEATURE                     Location/Qualifiers
misc_feature                1..33
                            note = primer #192 (IL2_L94F_L96I_R)
source                      1..33
                            mol_type = other DNA
                            organism = synthetic construct
SEQUENCE: 405
gtttcagatc ccttaatttc gaaaactatt acg                                       33

SEQ ID NO: 406              moltype = DNA   length = 33
FEATURE                     Location/Qualifiers
misc_feature                1..33
                            note = primer #193 (IL2_L94F_L96V_F)
source                      1..33
                            mol_type = other DNA
                            organism = synthetic construct
SEQUENCE: 406
cgtaatagtt ttcgaagtaa agggatctga aac                                       33

SEQ ID NO: 407              moltype = DNA   length = 33
FEATURE                     Location/Qualifiers
misc_feature                1..33
                            note = primer #194 (IL2_L94F_L96V_R)
source                      1..33
                            mol_type = other DNA
```

```
                        organism = synthetic construct
SEQUENCE: 407
gtttcagatc cctttacttc gaaaactatt acg                                     33

SEQ ID NO: 408          moltype = DNA  length = 30
FEATURE                 Location/Qualifiers
misc_feature            1..30
                        note = primer #195 (IL2_E95D_F)
source                  1..30
                        mol_type = other DNA
                        organism = synthetic construct
SEQUENCE: 408
gttctggacc taaagggatc tgaaacaaca                                         30

SEQ ID NO: 409          moltype = DNA  length = 30
FEATURE                 Location/Qualifiers
misc_feature            1..30
                        note = primer #196 (IL2_E95D_R)
source                  1..30
                        mol_type = other DNA
                        organism = synthetic construct
SEQUENCE: 409
tgttgtttca gatcccttta ggtccagaac                                         30

SEQ ID NO: 410          moltype = DNA  length = 33
FEATURE                 Location/Qualifiers
misc_feature            1..33
                        note = primer #197 (IL2_C125S_F)
source                  1..33
                        mol_type = other DNA
                        organism = synthetic construct
SEQUENCE: 410
agatggatta cctttagtca aagcatcatc tca                                     33

SEQ ID NO: 411          moltype = DNA  length = 33
FEATURE                 Location/Qualifiers
misc_feature            1..33
                        note = primer #198 (IL2_C125S_R)
source                  1..33
                        mol_type = other DNA
                        organism = synthetic construct
SEQUENCE: 411
tgagatgatg ctttgactaa aggtaatcca tct                                     33

SEQ ID NO: 412          moltype = DNA  length = 34
FEATURE                 Location/Qualifiers
misc_feature            1..34
                        note = primer #199 (IL2_Q126T_F)
source                  1..34
                        mol_type = other DNA
                        organism = synthetic construct
SEQUENCE: 412
gatggattac ctttagtaca agcatcatct caac                                    34

SEQ ID NO: 413          moltype = DNA  length = 34
FEATURE                 Location/Qualifiers
misc_feature            1..34
                        note = primer #200 (IL2_Q126T_R)
source                  1..34
                        mol_type = other DNA
                        organism = synthetic construct
SEQUENCE: 413
gttgagatga tgcttgtact aaaggtaatc catc                                    34

SEQ ID NO: 414          moltype = DNA  length = 33
FEATURE                 Location/Qualifiers
misc_feature            1..33
                        note = primer #201 (IL2_desA1_F)
source                  1..33
                        mol_type = other DNA
                        organism = synthetic construct
SEQUENCE: 414
taagaatata catatgccta cttcaagttc tac                                     33

SEQ ID NO: 415          moltype = DNA  length = 33
FEATURE                 Location/Qualifiers
misc_feature            1..33
                        note = primer #202 (IL2_desA1_R)
source                  1..33
```

```
                        mol_type = other DNA
                        organism = synthetic construct
SEQUENCE: 415
gtagaacttg aagtaggcat atgtatattc tta                              33

SEQ ID NO: 416          moltype = DNA  length = 34
FEATURE                 Location/Qualifiers
misc_feature            1..34
                        note = primer #203 (IL2_NdeI_desA1_N-term)
source                  1..34
                        mol_type = other DNA
                        organism = synthetic construct
SEQUENCE: 416
cgccatatgc ctacttcaag ttctacaaag aaaa                             34

SEQ ID NO: 417          moltype = DNA  length = 34
FEATURE                 Location/Qualifiers
misc_feature            1..34
                        note = primer #204 (IL2_BHI_C-term)
source                  1..34
                        mol_type = other DNA
                        organism = synthetic construct
SEQUENCE: 417
cgggatcctc aagtcagtgt tgagatgatg cttt                             34
```

US 12,415,842 B2

IMMUNOSTIMULATING IL-2 ANALOGS

CROSS REFERENCE TO RELATED APPLICATIONS

This application is a Divisional of U.S. application Ser. No. 17/915,808 filed Sep. 29, 2022, which is National Stage of International Application No. PCT/KR2021/004028 filed Mar. 31, 2021, claiming priority based on Korean Patent Application No. 10-2020-0039476 filed Mar. 31, 2020.

INCORPORATION BY REFERENCE OF SEQUENCE LISTING

The content of the electronically submitted sequence listing, file name: Q288594_SEQ_LIS_ST26_AS_FILED.XML; size: 595,082 bytes; and date of creation: Jul. 7, 2023, filed herewith, is incorporated herein by reference in its entirety.

TECHNICAL FIELD

The present invention relates to a novel interleukin-2 analog.

BACKGROUND ART

Interleukin-2 is an important immunostimulator with a molecular weight of about 15 kDa, which consists of a total of 133 amino acid residues, and activates various cells of the immune system including T cells and B cells. The high efficacy of interleukin-2 as an immune stimulant can be used for the treatment of various immune-related conditions including cancer and AIDS (Korean Patent Application Publication No. 10-2017-0070091). Currently, interleukin-2 (trademark name: Proleukin) is an FDA-approved drug for the treatment of metastatic renal cell carcinoma and metastatic melanoma. However, due to the severe toxicity associated with high-dose interleukin-2 therapy, the applicable patients are limited. In fact, this therapy is applied to only a small number of eligible patients. The toxicity associated with interleukin-2 includes severe fever, nausea, vomiting, vascular leak, severe hypotension, pulmonary edema, and vascular leak syndrome, which causes liver damage.

The interleukin-2 receptor has three kinds of subunit receptors. The subunit consists of an alpha chain (IL-2Rα, CD25), a beta chain (IL-2Rβ or CD122), and a gamma chain (IL-2Rγ or CD132). Interleukin-2 can exhibit various functions by binding to receptor subunits of various combinations. A single interleukin-2 alpha receptor is called a low-affinity interleukin-2 receptor, and it is not involved in signaling. A complex of interleukin-2 beta and gamma receptors binds to interleukin-2 with intermediate affinity. A complex of interleukin-2 alpha, beta, and gamma receptors binds to interleukin-2 with high affinity. The complex of interleukin-2 beta and gamma receptors is required for effective signal conversion through kinase activation in multiple signaling pathways. In particular, interleukin-2 beta- and gamma-binding receptors are prominent in CD8+ cells and natural killer (NK) cells. In addition, complexes of high-affinity interleukin-2 alpha, beta, and gamma receptors are usually found in CD4+ T regulatory cells (Treg), and recently they were also found in activated T cells. Since interleukin-2 beta receptors are distributed in CD8+ T cells or natural killer cells (NK cells) and are involved in the immune response in the body, studies have been conducted to develop therapeutic agents by increasing the activity of beta receptors for immune activation.

Meanwhile, despite the potential of interleukin-2 as a therapeutic agent for various immune-related conditions, there are still not many drugs which can reduce their doses while reducing toxicity and side effects, and thus there is an increasing demand for studies on new and improved drugs.

DISCLOSURE

Technical Problem

An object of the present invention is to provide an interleukin-2 analog.

Another object of the present invention is to provide an isolated nucleic acid encoding the interleukin-2 analog; a recombinant expression vector including the nucleic acid; and a transformant including the vector.

Still another object of the present invention is to provide a method for preparing the interleukin-2 analog.

Still another object of the present invention is to provide a method for increasing the binding affinity for interleukin-2 beta receptors, which includes modifying one or more amino acids in native interleukin-2.

Technical Solution

An aspect of the present invention provides a novel interleukin-2 analog (or IL-2 analog). The interleukin-2 analog is an interleukin-2 analog which has an increased binding affinity for interleukin-2 beta receptor compared to native interleukin-2 or aldesleukin (i.e., an interleukin-2 analog). In a specific embodiment, the interleukin-2 analog may include a sequence in which one or more amino acids in native interleukin-2 are modified.

In another specific embodiment, the interleukin-2 analog is characterized in that the interleukin-2 analog includes a sequence in which one or more amino acids corresponding to those at positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2 are modified.

The interleukin-2 analog according to any one of the previous specific embodiments is characterized in that it has an altered binding affinity for interleukin-2 alpha receptors and an increased binding affinity for interleukin-2 beta receptors compared to native interleukin-2 or aldesleukin.

The interleukin-2 analog according to any one of the previous specific embodiments is characterized in that one or more amino acids are added to the amino acid corresponding to position 133.

The interleukin-2 analog according to any one of the previous specific embodiments is characterized in that it is native interleukin-2, in which the amino acid at position 1 is removed and the amino acid at position 125 is substituted with a different amino acid.

The interleukin-2 analog according to any one of the previous specific embodiments is characterized in that it further includes 1 to 10 amino acid substitutions. The interleukin-2 analog according to any one of the previous specific embodiments is characterized in that one or more amino acids at positions 18, 19, 20, 22, 38, 42, 43, 45, 61, 68, 69, 74, 80, 81, 84, 85, 86, 88, 89, 91, 92, 94, and 96 are further substituted with different amino acids.

The interleukin-2 analog according to any one of the previous specific embodiments is characterized in that one or more amino acids at positions 18, 19, 22, 38, 42, 43, 45, 61, 68, 74, 80, 81, 84, 85, 86, 88, 91, 92, 94, and 96 are further substituted with different amino acids.

The interleukin-2 analog according to any one of the previous specific embodiments is characterized in that it is any one of the following analogs:

(a) an interleukin-2 analog, wherein the interleukin-2 analog is native interleukin-2 in which the amino acid at position 1 is removed and the amino acids at positions 125 and 32 are substituted with different amino acids;

(b) an interleukin-2 analog, wherein the interleukin-2 analog is native interleukin-2 in which the amino acid at position 1 is removed and the amino acids at positions 125 and 35 are substituted with different amino acids;

(c) an interleukin-2 analog, wherein the interleukin-2 analog is native interleukin-2 in which the amino acid at position 1 is removed and the amino acids at positions 125 and 38 are substituted with different amino acids;

(d) an interleukin-2 analog, wherein the interleukin-2 analog is native interleukin-2 in which the amino acid at position 1 is removed and the amino acids at positions 125 and 42 are substituted with different amino acids;

(e) an interleukin-2 analog, wherein the interleukin-2 analog is native interleukin-2 in which the amino acid at position 1 is removed and the amino acids at positions 125 and 43 are substituted with different amino acids;

(f) an interleukin-2 analog, wherein the interleukin-2 analog is native interleukin-2 in which the amino acid at position 1 is removed and the amino acids at positions 125 and 48 are substituted with different amino acids;

(g) an interleukin-2 analog, wherein the interleukin-2 analog is native interleukin-2 in which the amino acid at position 1 is removed and the amino acids at positions 125 and 49 are substituted with different amino acids;

(h) an interleukin-2 analog, wherein the interleukin-2 analog is native interleukin-2 in which the amino acid at position 1 is removed and the amino acids at positions 125 and 76 are substituted with different amino acids;

(i) an interleukin-2 analog, wherein the interleukin-2 analog is native interleukin-2 in which the amino acid at position 1 is removed and the amino acids at positions 125, 38, 42, 81, 92, 94, and 96 are substituted with different amino acids;

(j) an interleukin-2 analog, wherein the interleukin-2 analog is native interleukin-2 in which the amino acid at position 1 is removed and the amino acids at positions 125 and 87 are substituted with different amino acids;

(k) an interleukin-2 analog, wherein the interleukin-2 analog is native interleukin-2 in which the amino acid at position 1 is removed and the amino acids at positions 125, 38, and 42 are substituted with different amino acids;

(l) an interleukin-2 analog, wherein the interleukin-2 analog is native interleukin-2 in which the amino acid at position 1 is removed and the amino acids at positions 125, 38, and 80 are substituted with different amino acids;

(m) an interleukin-2 analog, wherein the interleukin-2 analog is native interleukin-2 in which the amino acid at position 1 is removed and the amino acids at positions 125, 38, and 84 are substituted with different amino acids;

(n) an interleukin-2 analog, wherein the interleukin-2 analog is native interleukin-2 in which the amino acid at position 1 is removed and the amino acids at positions 125, 19, 38, and 42 are substituted with different amino acids;

(o) an interleukin-2 analog, wherein the interleukin-2 analog is native interleukin-2 in which the amino acid at position 1 is removed and the amino acids at positions 125, 12, 38, and 42 are substituted with different amino acids;

(p) an interleukin-2 analog, wherein the interleukin-2 analog is native interleukin-2 in which the amino acid at position 1 is removed and the amino acids at positions 125, 38, 42, and 61 are substituted with different amino acids;

(q) an interleukin-2 analog, wherein the interleukin-2 analog is native interleukin-2 in which the amino acid at position 1 is removed and the amino acids at positions 125, 38, 42, and 84 are substituted with different amino acids;

(r) an interleukin-2 analog, wherein the interleukin-2 analog is native interleukin-2 in which the amino acid at position 1 is removed and the amino acids at positions 125, 38, 42, and 88 are substituted with different amino acids;

(s) an interleukin-2 analog, wherein the interleukin-2 analog is native interleukin-2 in which the amino acid at position 1 is removed and the amino acids at positions 125, 38, 42, and 89 are substituted with different amino acids;

(t) an interleukin-2 analog, wherein the interleukin-2 analog is native interleukin-2 in which the amino acid at position 1 is removed and the amino acids at positions 125, 38, 42, and 91 are substituted with different amino acids;

(u) an interleukin-2 analog, wherein the interleukin-2 analog is native interleukin-2 in which the amino acid at position 1 is removed and the amino acids at positions 125, 38, 42, and 94 are substituted with different amino acids;

(v) an interleukin-2 analog, wherein the interleukin-2 analog is native interleukin-2 in which the amino acid at position 1 is removed and the amino acids at positions 125, 38, 42, and 126 are substituted with different amino acids;

(w) an interleukin-2 analog, wherein the interleukin-2 analog is native interleukin-2 in which the amino acid at position 1 is removed and the amino acids at positions 125, 38, 80, and 84 are substituted with different amino acids;

(x) an interleukin-2 analog, wherein the interleukin-2 analog is native interleukin-2 in which the amino acid at position 1 is removed and the amino acids at positions 125, 38, 94, and 96 are substituted with different amino acids;

(y) an interleukin-2 analog, wherein the interleukin-2 analog is native interleukin-2 in which the amino acid at position 1 is removed and the amino acids at positions 125, 38, 81, and 92 are substituted with different amino acids;

(z) an interleukin-2 analog, wherein the interleukin-2 analog is native interleukin-2 in which the amino acid at position 1 is removed and the amino acids at positions 125, 61, 81, and 92 are substituted with different amino acids;

(aa) an interleukin-2 analog, wherein the interleukin-2 analog is native interleukin-2 in which the amino acid at position 1 is removed and the amino acids at positions 125, 38, 42, 81, and 92 are substituted with different amino acids;

(ab) an interleukin-2 analog, wherein the interleukin-2 analog is native interleukin-2 in which the amino acid at position 1 is removed and the amino acids at positions 125, 38, 80, 81, and 92 are substituted with different amino acids, (ac) an interleukin-2 analog, wherein the interleukin-2 analog is native interleukin-2 in which the amino acid at position 1 is removed and the amino acids at positions 125, 38, 81, 84, and 92 are substituted with different amino acids;

(ad) an interleukin-2 analog, wherein the interleukin-2 analog is native interleukin-2 in which the amino acid at position 1 is removed and the amino acids at positions 125, 20, 38, 42, 81, and 92 are substituted with different amino acids, (ae) an interleukin-2 analog, wherein the interleukin-2 analog is native interleukin-2 in which the amino acid at position 1 is removed and the amino acids at positions 125, 38, 42, 80, 81, and 92 are substituted with different amino acids, (af) an interleukin-2 analog, wherein the interleukin-2 analog is native interleukin-2 in which the amino acid at position 1 is removed and the amino acids at positions 125, 38, 42, 74, 81, and 92 are substituted with different amino acids;

(ag) an interleukin-2 analog, wherein the interleukin-2 analog is native interleukin-2 in which the amino acid at position 1 is removed and the amino acids at positions 125, 38, 42, 81, 84, and 92 are substituted with different amino acids, (ah) an interleukin-2 analog, wherein the interleukin-2 analog is native interleukin-2 in which the amino acid at position 1 is removed and the amino acids at positions 125, 38, 42, 81, 88, and 92 are substituted with different amino acids;

(ai) an interleukin-2 analog, wherein the interleukin-2 analog is native interleukin-2 in which the amino acid at position 1 is removed and the amino acids at positions 125, 38, 42, 85, 86, and 92 are substituted with different amino acids, (aj) an interleukin-2 analog, wherein the interleukin-2 analog is native interleukin-2 in which the amino acid at position 1 is removed and the amino acids at positions 125, 38, 80, 81, 85, and 92 are substituted with different amino acids;

(ak) an interleukin-2 analog, wherein the interleukin-2 analog is native interleukin-2 in which the amino acid at position 1 is removed and the amino acids at positions 125, 38, 80, 81, 86, and 92 are substituted with different amino acids;

(al) an interleukin-2 analog, wherein the interleukin-2 analog is native interleukin-2 in which the amino acid at position 1 is removed and the amino acids at positions 125, 80, 81, 85, 86, and 92 are substituted with different amino acids;

(am) an interleukin-2 analog, wherein the interleukin-2 analog is native interleukin-2 in which the amino acid at position 1 is removed and the amino acids at positions 125, 38, 42, 45, 74, 81, and 92 are substituted with different amino acids;

(an) an interleukin-2 analog, wherein the interleukin-2 analog is native interleukin-2 in which the amino acid at position 1 is removed and the amino acids at positions 125, 38, 42, 74, 80, 81, and 92 are substituted with different amino acids;

(ao) an interleukin-2 analog, wherein the interleukin-2 analog is native interleukin-2 in which the amino acid at position 1 is removed and the amino acids at positions 125, 38, 42, 80, 81, 84, and 92 are substituted with different amino acids;

(ap) an interleukin-2 analog, wherein the interleukin-2 analog is native interleukin-2 in which the amino acid at position 1 is removed and the amino acids at positions 125, 38, 45, 80, 85, 86, and 92 are substituted with different amino acids;

(aq) an interleukin-2 analog, wherein the interleukin-2 analog is native interleukin-2 in which the amino acid at position 1 is removed and the amino acids at positions 125, 38, 80, 81, 85, 86, and 92 are substituted with different amino acids;

(ar) an interleukin-2 analog, wherein the interleukin-2 analog is native interleukin-2 in which the amino acid at position 1 is removed and the amino acids at positions 125, 42, 80, 81, 85, 86, and 92 are substituted with different amino acids;

(as) an interleukin-2 analog, wherein the interleukin-2 analog is native interleukin-2 in which the amino acid at position 1 is removed and the amino acids at positions 125, 61, 80, 81, 85, 86, and 92 are substituted with different amino acids;

(at) an interleukin-2 analog, wherein the interleukin-2 analog is native interleukin-2 in which the amino acid at position 1 is removed and the amino acids at positions 125, 69, 80, 81, 85, 86, and 92 are substituted with different amino acids;

(au) an interleukin-2 analog, wherein the interleukin-2 analog is native interleukin-2 in which the amino acid at position 1 is removed and the amino acids at positions 125, 80, 81, 85, 86, 91, and 92 are substituted with different amino acids;

(av) an interleukin-2 analog, wherein the interleukin-2 analog is native interleukin-2 in which the amino acid at position 1 is removed and the amino acids at positions 125, 18, 22, 80, 81, 85, 86, and 92 are substituted with different amino acids;

(aw) an interleukin-2 analog, wherein the interleukin-2 analog is native interleukin-2 in which the amino acid at position 1 is removed and the amino acids at positions 125, 38, 42, 80, 81, 85, 86, and 92 are substituted with different amino acids;

(ax) an interleukin-2 analog, wherein the interleukin-2 analog is native interleukin-2 in which the amino acid at position 1 is removed and the amino acids at positions 125, 38, 42, 45, 74, 80, 81, and 92 are substituted with different amino acids;

(ay) an interleukin-2 analog, wherein the interleukin-2 analog is native interleukin-2 in which the amino acid at position 1 is removed and the amino acids at positions 125, 38, 68, 80, 81, 85, 86, and 92 are substituted with different amino acids;

(az) an interleukin-2 analog, wherein the interleukin-2 analog is native interleukin-2 in which the amino acid at position 1 is removed and the amino acids at positions 125, 69, 74, 80, 81, 85, 86, and 92 are substituted with different amino acids;
(ba) an interleukin-2 analog, wherein the interleukin-2 analog is native interleukin-2 in which the amino acid at position 1 is removed and the amino acids at positions 125, 80, 81, 84, 85, 86, 91, and 92 are substituted with different amino acids;
(bb) an interleukin-2 analog, wherein the interleukin-2 analog is native interleukin-2 in which the amino acid at position 1 is removed and the amino acids at positions 125, 80, 81, 85, 86, 92, 94, and 96 are substituted with different amino acids;
(bc) an interleukin-2 analog, wherein the interleukin-2 analog is native interleukin-2 in which the amino acid at position 1 is removed and the amino acids at positions 125, 18, 19, 22, 80, 81, 85, 86, and 92 are substituted with different amino acids;
(bd) an interleukin-2 analog, wherein the interleukin-2 analog is native interleukin-2 in which the amino acid at position 1 is removed and the amino acids at positions 125, 18, 22, 38, 80, 81, 85, 86, and 92 are substituted with different amino acids;
(be) an interleukin-2 analog, wherein the interleukin-2 analog is native interleukin-2 in which the amino acid at position 1 is removed and the amino acids at positions 125, 18, 22, 61, 80, 81, 85, 86, and 92 are substituted with different amino acids;
(bf) an interleukin-2 analog, wherein the interleukin-2 analog is native interleukin-2 in which the amino acid at position 1 is removed and the amino acids at positions 125, 18, 22, 68, 80, 81, 85, 86, and 92 are substituted with different amino acids;
(bg) an interleukin-2 analog, wherein the interleukin-2 analog is native interleukin-2 in which the amino acid at position 1 is removed and the amino acids at positions 125, 35, 38, 42, 80, 81, 85, 86, and 92 are substituted with different amino acids;
(bh) an interleukin-2 analog, wherein the interleukin-2 analog is native interleukin-2 in which the amino acid at position 1 is removed and the amino acids at positions 125, 38, 42, 45, 80, 81, 85, 86, and 92 are substituted with different amino acids;
(bi) an interleukin-2 analog, wherein the interleukin-2 analog is native interleukin-2 in which the amino acid at position 1 is removed and the amino acids at positions 125, 38, 42, 80, 81, 85, 86, 91, and 92 are substituted with different amino acids;
(bj) an interleukin-2 analog, wherein the interleukin-2 analog is native interleukin-2 in which the amino acid at position 1 is removed and the amino acids at positions 125, 38, 42, 80, 81, 85, 86, 92, and 95 are substituted with different amino acids;
(bk) an interleukin-2 analog, wherein the interleukin-2 analog is native interleukin-2 in which the amino acid at position 1 is removed and the amino acids at positions 125, 35, 38, 42, 74, 80, 81, 85, 86, and 92 are substituted with different amino acids;
(bl) an interleukin-2 analog, wherein the interleukin-2 analog is native interleukin-2 in which the amino acid at position 1 is removed and the amino acids at positions 125, 38, 42, 43, 61, 80, 81, 85, 86, and 92 are substituted with different amino acids;
(bm) an interleukin-2 analog, wherein the interleukin-2 analog is native interleukin-2 in which the amino acid at position 1 is removed and the amino acids at positions 125, 38, 42, 80, 81, 85, 86, 91, 92, and 95 are substituted with different amino acids;
(bn) an interleukin-2 analog, wherein the interleukin-2 analog is native interleukin-2 in which the amino acid at position 1 is removed and the amino acids at positions 125, 35, 38, 42, 74, 80, 81, 82, 85, 86, and 92 are substituted with different amino acids;
(bo) an interleukin-2 analog in which the amino acid at position 1 is removed and the amino acids at positions 125, 80, 81, 86, and 92 are substituted with different amino acids in native interleukin-2; and
(bp) an interleukin-2 analog in which the amino acid at position 1 is removed and the amino acids at positions 125, 80, 81, 85, and 86 are substituted with different amino acids in native interleukin-2.

The interleukin-2 analog according to any one of the previous specific embodiments is characterized in that it includes any one amino acid substitution selected from the group consisting of the following amino acid substitutions:
(a) a substitution in which the amino acid at position 12 is substituted with valine or phenylalanine;
(b) a substitution in which the amino acid at position 18 is substituted with arginine;
(c) a substitution in which the amino acid at position 19 is substituted with tyrosine, valine, phenylalanine, or arginine;
(d) a substitution in which the amino acid at position 20 is substituted with valine or phenylalanine;
(e) a substitution in which the amino acid at position 22 is substituted with glutamic acid;
(f) a substitution in which the amino acid at position 32 is substituted with cysteine;
(g) a substitution in which the amino acid at position 35 is substituted with cysteine or glutamic acid;
(h) a substitution in which the amino acid at position 38 is substituted with alanine or aspartic acid;
(i) a substitution in which the amino acid at position 42 is substituted with lysine, alanine, or tryptophan;
(j) a substitution in which the amino acid at position 43 is substituted with cysteine, glutamic acid, or glutamine;
(k) a substitution in which the amino acid at position 45 is substituted with alanine;
(l) a substitution in which the amino acid at position 48 is substituted with cysteine;
(m) a substitution in which the amino acid at position 49 is substituted with cysteine;
(n) a substitution in which the amino acid at position 61 is substituted with glutamine, arginine, or aspartic acid;
(o) a substitution in which the amino acid at position 68 is substituted with aspartic acid or glutamine;
(p) a substitution in which the amino acid at position 69 is substituted with glycine;
(q) a substitution in which the amino acid at position 74 is substituted with histidine or alanine;
(r) a substitution in which the amino acid at position 76 is substituted with cysteine;
(s) a substitution in which the amino acid at position 80 is substituted with phenylalanine, tyrosine, valine, aspartic acid, or tryptophan;
(t) a substitution in which the amino acid at position 81 is substituted with aspartic acid, glutamic acid, or asparagine;
(u) a substitution in which the amino acid at position 82 is substituted with glycine or valine;
(v) a substitution in which the amino acid at position 84 is substituted with glutamic acid, valine, or phenylalanine;

(w) a substitution in which the amino acid at position 85 is substituted with valine, alanine, glycine, tryptophan, tyrosine, threonine, isoleucine, glutamic acid, or phenylalanine;

(x) a substitution in which the amino acid at position 86 is substituted with valine, alanine, glycine, or leucine;

(y) a substitution in which the amino acid at position 87 is substituted with cysteine;

(z) a substitution in which the amino acid at position 88 is substituted with glutamine, valine, or phenylalanine;

(aa) a substitution in which the amino acid at position 89 is substituted with phenylalanine;

(ab) a substitution in which the amino acid at position 91 is substituted with threonine, phenylalanine, or glutamic acid;

(ac) a substitution in which the amino acid at position 92 is substituted with phenylalanine, leucine, tyrosine, or tryptophan;

(ad) a substitution in which the amino acid at position 95 is substituted with aspartic acid;

(ae) a substitution in which the amino acid at position 96 is substituted with phenylalanine, valine, or isoleucine; and (af) a substitution in which the amino acid at position 126 is substituted with threonine.

The interleukin-2 analog according to any one of the previous specific embodiments is characterized in that it is selected from the group consisting of SEQ ID NOS: 3 to 106.

Another aspect to implement the present invention provides an isolated nucleic acid encoding the interleukin-2 analog; a recombinant expression vector which includes the nucleic acid; and a transformant which includes the vector.

Still another aspect to implement the present invention provides a method for preparing the interleukin-2 analog.

Still another aspect to implement the present invention provides a method for increasing the binding affinity for interleukin-2 beta receptors, which includes modifying one or more amino acids in native interleukin-2, in which the modification may be modifications in one or more amino acids selected from the group consisting of amino acids corresponding to positions at 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133.

Still another aspect to implement the present invention provides an interleukin-2 analog which includes any one sequence selected from the group consisting of amino acid sequences of SEQ ID NOS: 3 to 106.

Still another aspect to implement the present invention provides an interleukin-2 analog which includes an amino acid sequence represented by General Formula 1 below:

[General Formula 1]
(General Formula 1, SEQ ID NO: 212)
X1-P-T-S-S-S-T-K-K-T-Q-L-Q-L-E-H-L-X18-X19-D-L-

X22-M-I-L-N-G-I-N-N-Y-K-N-P-K-L-T-X38-M-L-T-X42-

X43-F-X45-M-P-K-K-A-T-E-L-K-H-L-Q-C-L-E-X61-E-L-K-

P-L-E-X68-V-L-N-L-A-X74-S-K-N-F-H-X80-X81-P-R-X84-

X85-X86-S-N-I-N-X91-X92-V-X94-E-X96-K-G-S-E-T-T-F-

M-C-E-Y-A-D-E-T-A-T-I-V-E-F-L-N-R-W-I-T-F-S-Q-S-I-

I-S-T-L-T wherein in General Formula 1 above,

X1 is a deletion;
X18 is leucine (L) or arginine (R);
X19 is leucine (L) or tyrosine (Y);
X22 is glutamic acid (E) or glutamine (Q);
X38 is alanine (A), aspartic acid (D), or arginine (R);
X42 is alanine (A), phenylalanine (F), lysine (K), or tryptophan (W);
X43 is glutamic acid (E), lysine (K), or glutamine (Q);
X45 is alanine (A) or tyrosine (Y);
X61 is aspartic acid (D), glutamic acid (E), glutamine (Q), or arginine (R);
X68 is aspartic acid (D) or glutamic acid (E);
X74 is histidine (H) or glutamine (Q);
X80 is phenylalanine (F), leucine (L), valine (V), or tyrosine (Y);
X81 is aspartic acid (D), glutamic acid (E), or arginine (R);
X84 is aspartic acid (D) or glutamic acid (E);
X85 is alanine (A), glutamic acid (E), glycine (G), leucine (L), valine (V), tryptophan (W), or tyrosine (Y);
X86 is alanine (A), glycine (G), isoleucine (I), or valine (V);
X91 is threonine (T) or valine (V);
X92 is phenylalanine (F), isoleucine (I), or tyrosine (Y);
X94 is phenylalanine (F) or leucine (L); and
X96 is phenylalanine (F) or leucine (L).

In a specific embodiment, the interleukin-2 analog is characterized in that it includes any one sequence selected from the group consisting of amino acid sequences of SEQ ID NOS: 10, 13, 14, 15, 16, 17, 20, 21, 22, 32, 35, 36, 42, 53, 54, 56, 58, 59, 60, 62, 71, 72, 74, 75, 76, 77, 78, 85, 87, 89, 91, 92, 93, 94, 95, 98, 99, 100, 101, 103, 104, 105, and 106.

In another specific embodiment, the interleukin-2 analog is characterized in that in General Formula 1 above, X43 is lysine (K);
X45 is tyrosine (Y);
X61 is aspartic acid (D), glutamic acid (E), or glutamine (Q);
X68 is glutamic acid (E);
X74 is glutamine (Q);
X80 is phenylalanine (F) or leucine (L);
X85 is leucine (L), valine (V), or tyrosine (Y);
X86 is isoleucine (I) or valine (V); and
X92 is phenylalanine (F) or isoleucine (I).

The interleukin-2 analog according to any one of the previous specific embodiments is characterized in that it includes any one sequence selected from the group consisting of amino acid sequences of SEQ ID NOS: 10, 13, 14, 16, 17, 20, 21, 22, 32, 35, 36, 42, 53, 54, 87, 89, 91, 92, 93, 94, 98, 99, 100, 101, 103, 104, and 105.

The interleukin-2 analog according to any one of the previous specific embodiments is characterized in that it further includes one or more amino acids at the C-terminus thereof.

Still another aspect to implement the present invention provides an interleukin-2 analog which includes an amino acid sequence represented by General Formula 2 below:

[General Formula 2]
(General Formula 2, SEQ ID NO: 213)
X1-P-T-S-S-S-T-K-K-T-Q-L-Q-L-E-H-L-X18-L-D-L-X22-

M-I-L-N-G-I-N-N-Y-K-N-P-K-L-T-X38-M-L-T-X42-K-F-Y-

M-P-K-K-A-T-E-L-K-H-L-Q-C-L-E-X61-E-L-K-P-L-E-X68-

-continued

```
V-L-N-L-A-Q-S-K-N-F-H-F-X81-P-R-D-X85-X86-S-N-I-N-

V-F-V-L-E-L-K-G-S-E-T-T-F-M-C-E-Y-A-D-E-T-A-T-I-V-

E-F-L-N-R-W-I-T-F-S-Q-S-I-I-S-T-L-T
``` wherein in General Formula 2 above,
X1 is a deletion,
X18 is leucine (L) or arginine (R);
X22 is glutamic acid (E) or glutamine (Q);
X38 is alanine (A) or arginine (R);
X42 is phenylalanine (F) or lysine (K);
X61 is aspartic acid (D) or glutamic acid (E);
X68 is aspartic acid (D) or glutamic acid (E);
X81 is aspartic acid (D) or glutamic acid (E);
X85 is leucine (L) or valine (V); and
X86 is isoleucine (I) or valine (V).

In a specific embodiment, the interleukin-2 analog is characterized in that it includes any one sequence selected from the group consisting of amino acid sequences of SEQ ID NOS: 22, 42, 53, 87, 105, and 106.

In another specific embodiment, the interleukin-2 analog is characterized in that it further includes one or more amino acids at the C-terminus thereof.

Advantageous Effects

The interleukin-2 analog according to the present invention is an analog which has increased binding affinity for interleukin-2 beta receptors in vivo and can be for various purposes.

BRIEF DESCRIPTION OF DRAWINGS

FIG. 1(A)-FIG. 1(C) show the results confirming the binding affinity of an interleukin-2 analog for interleukin-2 alpha receptors, in which FIG. 1(A) represents interleukin-2 analog #86, FIG. 1(B) represents interleukin-2 analog #104, and FIG. 1(C) represents interleukin-2 analog #105.

FIG. 2(A)-FIG. 2(C) show the results confirming the binding affinity of an interleukin-2 analog for interleukin-2 beta receptors, in which FIG. 2(A) represents interleukin-2 analog #86, FIG. 2(B) represents interleukin-2 analog #104, and FIG. 2(C) represents interleukin-2 analog #105.

DETAILED DESCRIPTION FOR CARRYING OUT THE INVENTION

Figure 1A:
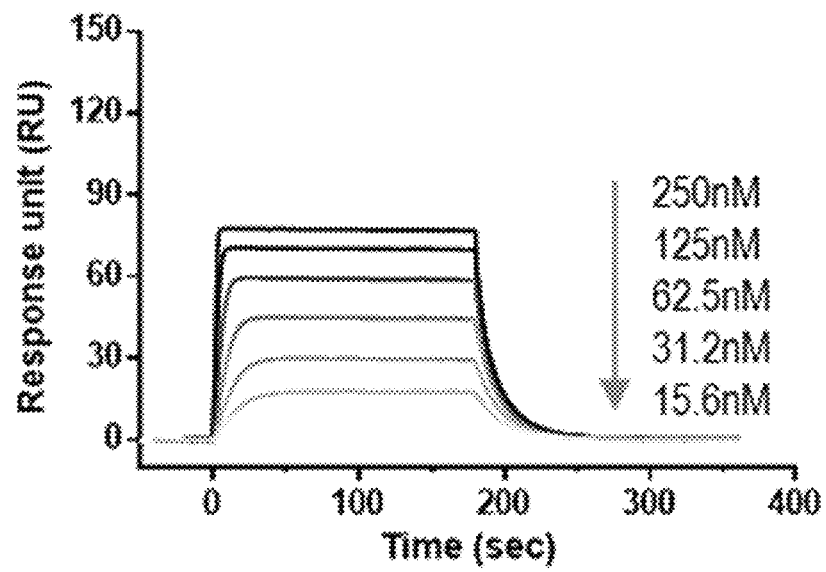

The details for carrying out the present invention will be described as follows. Meanwhile, respective descriptions and embodiments disclosed in the present invention may also be applied to other descriptions and embodiments. That is, all combinations of various elements disclosed in the present invention fall within the scope of the present invention. Further, the scope of the present invention cannot be considered to be limited by the specific description below.

Over the entire specification of the present invention, the conventional one-letter and three-letter codes for amino acids are used. Additionally, the amino acids mentioned herein are abbreviated according to the nomenclature rules of the IUPAC-IUB as follows:

| alanine | A | arginine | R |
|---|---|---|---|
| asparagine | N | aspartic acid | D |
| cysteine | C | glutamic acid | E |
| glutamine | Q | glycine | G |
| histidine | H | isoleucine | I |
| leucine | L | lysine | K |
| methionine | M | phenylalanine | F |
| proline | P | serine | S |
| threonine | T | tryptophan | W |
| tyrosine | Y | valine | V |

Still another aspect of the present invention provides an interleukin-2 analog. The interleukin-2 analog of the present invention is characterized in that its binding affinity for interleukin-2 receptors is altered, and in particular in that it has increased binding affinity for interleukin-2 beta receptors. Specifically, the interleukin-2 analog of the present invention may be one which has increased binding affinity for interleukin-2 beta receptors, and more specifically one which has altered (increased or decreased) binding affinity for interleukin-2 alpha receptors compared to native interleukin-2 or known aldesleukin.

As used herein, the term "interleukin-2 (IL-2)" refers to a type of cytokine which transmits signals in the immune system in vivo. The interleukin-2 is generally known as an important immunostimulator with a size of about 15 kDa.

As used herein, the term "interleukin-2 analog" refers to native interleukin-2 in which one or more amino acids in the sequence thereof are modified. Particularly in the present invention, the interleukin-2 analog may be one which has reduced or increased binding affinity for interleukin-2 receptors compared to native interleukin-2, in which amino acid(s) in native interleukin-2 is(are) modified. The interleukin-2 analog of the present invention may be one which is not naturally occurring.

The native interleukin-2 may be a human interleukin-2, and its sequence may be obtained from known databases, etc. Specifically, the native interleukin-2 may have an amino acid sequence of SEQ ID NO: 1, but is not limited thereto.

In the present invention, what is meant by "native interleukin-2 may have an amino acid sequence of SEQ ID NO: 1" is that not only the sequence which is the same as SEQ ID NO: 1, but also sequences which have a homology of 80% or higher, 85% or higher, 90% or higher, 91% or higher, 92% or higher, 93% or higher, 94% or higher, 95% or higher, 96% or higher, 97% or higher, 98% or higher, and 99% or higher to SEQ ID NO: 1 belong to the scope of native interleukin-2 of the present invention; and that the corresponding position(s) of amino acid modification is(are) altered on the amino acid sequence of SEQ ID NO: 1 when sequences having a homology of 80% or higher, 85% or higher, 90% or higher, 91% or higher, 92% or higher, 93% or higher, 94% or higher, 95% or higher, 96% or higher, 97% or higher, 98% or higher, and 99% or higher are aligned based on SEQ ID NO: 1.

In the present invention, what is meant by "one or more amino acids in the native sequence are altered" may be that a modification selected from the group consisting of substitution, addition, deletion, modification, and a combination thereof has occurred in at least one amino acid in the native sequence.

Specifically, the interleukin-2 analog of the present invention may include a sequence in which one or more amino acids corresponding to positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2 are modified. Specifically, the interleukin-2 analog of the present invention may be native interleukin-2 in which the amino acid at position 1 is removed and the amino acid at position 125 is substituted with a different amino acid; and which further includes 1, 2, 3, 4, 5, 6, 7, 8, 9, 10, or more amino acid substitutions. Although not limited thereto, the amino acid at position 125 (i.e., cysteine) may be substituted with serine, and the amino acid(s) at which a further substitution occurs may be amino acids corresponding to positions 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 126, and 133.

Additionally, interleukin-2 analogs which include substitution, addition, deletion, modification, etc. of amino acid residues in addition to the positions for modification above to the extent that can be performed for the stability and increase of half-life of a peptide known in the art are also included within the scope of the present invention.

As used herein, the term "aldesleukin" or "interleukin-2 analog (aldesleukin)", which is a commercially available interleukin-2 analog, may be aldesleukin (trademark name: Proleukin®), and specifically may be one which has the amino acid sequence of SEQ ID NO: 2. In the present invention, these terms are used interchangeably with "interleukin-2 analog 1". The interleukin analog according to the present invention may have altered binding affinity for interleukin-2 alpha receptors and/or increased binding affinity for interleukin-2 beta receptors compared to the interleukin-2 analog 1.

Although interleukin-2 alpha receptors are not known to be involved in the signaling system of interleukin-2, they increase the binding affinity of interleukin-2 for other interleukin-2 receptors (beta or gamma receptors) by 10 to 100 times and are expressed in CD4$^+$ regulatory T cells, etc.

Since interleukin-2 beta receptors are mainly distributed in CD8$^+$ T cells or natural killer cells (NK cells) and have an important role of activating immune responses and macrophages, it is expected that tumor cell death and activation of the body's immune responses can be promoted through the activation of interleukin-2 beta receptors.

Accordingly, the interleukin-2 analog of the present invention which has increased binding affinity for interleukin-2 beta receptors can have a therapeutic effect where the suppression and death of tumors is increased while side effects are reduced.

In the present invention, the interleukin-2 analog may include a sequence of native interleukin-2 in which the amino acid at position 1 is removed and the amino acid at position 125 is substituted with a different amino acid, and which further includes 1 to 10 amino acid modifications. For example, the interleukin-2 analog may include a sequence of native interleukin-2 in which the amino acid at position 125 is substituted with serine and one or more amino acids at positions 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, and 126 are substituted with different amino acids and/or one or more amino acids are added on the amino acid at position 133, but the sequence is not limited thereto, and any interleukin-2 analog which has altered binding affinity for interleukin-2 alpha receptors and increased binding affinity for interleukin-2 beta receptors compared to native interleukin-2 and/or aldesleukin is included without limitation.

In an embodiment, the interleukin-2 analog may be one in which one or more amino acids are added to the amino acid corresponding to position 133, but the interleukin-2 analog is not limited thereto. For the purpose of the present invention, the amino acids to be added are not limited with regard to the type or length thereof as long as the interleukin-2 analog has altered binding affinity for interleukin-2 alpha receptors and increased binding affinity for interleukin-2 beta receptors compared to native interleukin-2 and/or aldesleukin, and amino acids which are not naturally occurring and amino acids with a chemical modification can also be added in addition to natural amino acids.

In another embodiment, the interleukin-2 analog may be native interleukin-2 in which the amino acid at position 1 is removed; the amino acid at position 125 is substituted with a different amino acid; and 1, 2, 3, 4, 5, 6, 7, 8, 9, or more amino acids among the amino acids at positions 18, 19, 20, 22, 38, 42, 43, 45, 61, 68, 69, 74, 80, 81, 84, 85, 86, 88, 89, 91, 92, 94, and 96 are substituted with different amino acids, but the interleukin-2 analog is not limited thereto.

In still another embodiment, the interleukin-2 analog may be native interleukin-2 in which the amino acid at position 1 is removed; the amino acid at position 125 is substituted with a different amino acid; and 1, 2, 3, 4, 5, 6, 7, 8, 9, or more amino acids among the amino acids at positions 18, 19, 22, 38, 42, 43, 45, 61, 68, 74, 80, 81, 84, 85, 86, 88, 91, 92, 94, and 96 are substituted with different amino acids, but the interleukin-2 analog is not limited thereto.

In still another embodiment, the interleukin-2 analog may be any one selected from the group consisting of the following analogs:
(a) an interleukin-2 analog, wherein the interleukin-2 analog is native interleukin-2 in which the amino acid at position 1 is removed and the amino acids at positions 125 and 32 are substituted with different amino acids;
(b) an interleukin-2 analog, wherein the interleukin-2 analog is native interleukin-2 in which the amino acid at position 1 is removed and the amino acids at positions 125 and 35 are substituted with different amino acids;
(c) an interleukin-2 analog, wherein the interleukin-2 analog is native interleukin-2 in which the amino acid at position 1 is removed and the amino acids at positions 125 and 38 are substituted with different amino acids;
(d) an interleukin-2 analog, wherein the interleukin-2 analog is native interleukin-2 in which the amino acid at position 1 is removed and the amino acids at positions 125 and 42 are substituted with different amino acids;
(e) an interleukin-2 analog, wherein the interleukin-2 analog is native interleukin-2 in which the amino acid at position 1 is removed and the amino acids at positions 125 and 43 are substituted with different amino acids;
(f) an interleukin-2 analog, wherein the interleukin-2 analog is native interleukin-2 in which the amino acid at position 1 is removed and the amino acids at positions 125 and 48 are substituted with different amino acids;
(g) an interleukin-2 analog, wherein the interleukin-2 analog is native interleukin-2 in which the amino acid at position 1 is removed and the amino acids at positions 125 and 49 are substituted with different amino acids;
(h) an interleukin-2 analog, wherein the interleukin-2 analog is native interleukin-2 in which the amino acid at position 1 is removed and the amino acids at positions 125 and 76 are substituted with different amino acids;
(i) an interleukin-2 analog, wherein the interleukin-2 analog is native interleukin-2 in which the amino acid at position 1 is removed and the amino acids at positions 125, 38, 42, 81, 92, 94, and 96 are substituted with different amino acids;

(j) an interleukin-2 analog, wherein the interleukin-2 analog is native interleukin-2 in which the amino acid at position 1 is removed and the amino acids at positions 125 and 87 are substituted with different amino acids;

(k) an interleukin-2 analog, wherein the interleukin-2 analog is native interleukin-2 in which the amino acid at position 1 is removed and the amino acids at positions 125, 38, and 42 are substituted with different amino acids;

(l) an interleukin-2 analog, wherein the interleukin-2 analog is native interleukin-2 in which the amino acid at position 1 is removed and the amino acids at positions 125, 38, and 80 are substituted with different amino acids;

(m) an interleukin-2 analog, wherein the interleukin-2 analog is native interleukin-2 in which the amino acid at position 1 is removed and the amino acids at positions 125, 38, and 84 are substituted with different amino acids;

(n) an interleukin-2 analog, wherein the interleukin-2 analog is native interleukin-2 in which the amino acid at position 1 is removed and the amino acids at positions 125, 19, 38, and 42 are substituted with different amino acids;

(o) an interleukin-2 analog, wherein the interleukin-2 analog is native interleukin-2 in which the amino acid at position 1 is removed and the amino acids at positions 125, 12, 38, and 42 are substituted with different amino acids;

(p) an interleukin-2 analog, wherein the interleukin-2 analog is native interleukin-2 in which the amino acid at position 1 is removed and the amino acids at positions 125, 38, 42, and 61 are substituted with different amino acids;

(q) an interleukin-2 analog, wherein the interleukin-2 analog is native interleukin-2 in which the amino acid at position 1 is removed and the amino acids at positions 125, 38, 42, and 84 are substituted with different amino acids;

(r) an interleukin-2 analog, wherein the interleukin-2 analog is native interleukin-2 in which the amino acid at position 1 is removed and the amino acids at positions 125, 38, 42, and 88 are substituted with different amino acids;

(s) an interleukin-2 analog, wherein the interleukin-2 analog is native interleukin-2 in which the amino acid at position 1 is removed and the amino acids at positions 125, 38, 42, and 89 are substituted with different amino acids;

(t) an interleukin-2 analog, wherein the interleukin-2 analog is native interleukin-2 in which the amino acid at position 1 is removed and the amino acids at positions 125, 38, 42, and 91 are substituted with different amino acids;

(u) an interleukin-2 analog, wherein the interleukin-2 analog is native interleukin-2 in which the amino acid at position 1 is removed and the amino acids at positions 125, 38, 42, and 94 are substituted with different amino acids;

(v) an interleukin-2 analog, wherein the interleukin-2 analog is native interleukin-2 in which the amino acid at position 1 is removed and the amino acids at positions 125, 38, 42, and 126 are substituted with different amino acids;

(w) an interleukin-2 analog, wherein the interleukin-2 analog is native interleukin-2 in which the amino acid at position 1 is removed and the amino acids at positions 125, 38, 80, and 84 are substituted with different amino acids;

(x) an interleukin-2 analog, wherein the interleukin-2 analog is native interleukin-2 in which the amino acid at position 1 is removed and the amino acids at positions 125, 38, 94, and 96 are substituted with different amino acids;

(y) an interleukin-2 analog, wherein the interleukin-2 analog is native interleukin-2 in which the amino acid at position 1 is removed and the amino acids at positions 125, 38, 81, and 92 are substituted with different amino acids;

(z) an interleukin-2 analog, wherein the interleukin-2 analog is native interleukin-2 in which the amino acid at position 1 is removed and the amino acids at positions 125, 61, 81, and 92 are substituted with different amino acids;

(aa) an interleukin-2 analog, wherein the interleukin-2 analog is native interleukin-2 in which the amino acid at position 1 is removed and the amino acids at positions 125, 38, 42, 81, and 92 are substituted with different amino acids;

(ab) an interleukin-2 analog, wherein the interleukin-2 analog is native interleukin-2 in which the amino acid at position 1 is removed and the amino acids at positions 125, 38, 80, 81, and 92 are substituted with different amino acids;

(ac) an interleukin-2 analog, wherein the interleukin-2 analog is native interleukin-2 in which the amino acid at position 1 is removed and the amino acids at positions 125, 38, 81, 84, and 92 are substituted with different amino acids, (ad) an interleukin-2 analog, wherein the interleukin-2 analog is native interleukin-2 in which the amino acid at position 1 is removed and the amino acids at positions 125, 20, 38, 42, 81, and 92 are substituted with different amino acids;

(ae) an interleukin-2 analog, wherein the interleukin-2 analog is native interleukin-2 in which the amino acid at position 1 is removed and the amino acids at positions 125, 38, 42, 80, 81, and 92 are substituted with different amino acids, (af) an interleukin-2 analog, wherein the interleukin-2 analog is native interleukin-2 in which the amino acid at position 1 is removed and the amino acids at positions 125, 38, 42, 74, 81, and 92 are substituted with different amino acids, (ag) an interleukin-2 analog, wherein the interleukin-2 analog is native interleukin-2 in which the amino acid at position 1 is removed and the amino acids at positions 125, 38, 42, 81, 84, and 92 are substituted with different amino acids;

(ah) an interleukin-2 analog, wherein the interleukin-2 analog is native interleukin-2 in which the amino acid at position 1 is removed and the amino acids at positions 125, 38, 42, 81, 88, and 92 are substituted with different amino acids;

(ai) an interleukin-2 analog, wherein the interleukin-2 analog is native interleukin-2 in which the amino acid at position 1 is removed and the amino acids at positions 125, 38, 42, 85, 86, and 92 are substituted with different amino acids, (aj) an interleukin-2 analog, wherein the interleukin-2 analog is native interleukin-2 in which the amino acid at position 1 is removed and the amino acids at positions 125, 38, 80, 81, 85, and 92 are substituted with different amino acids;

(ak) an interleukin-2 analog, wherein the interleukin-2 analog is native interleukin-2 in which the amino acid at position 1 is removed and the amino acids at positions 125, 38, 80, 81, 86, and 92 are substituted with different amino acids, (al) an interleukin-2 analog, wherein the interleukin-2 analog is native interleukin-2 in which the amino acid at position 1 is removed and the amino acids at positions 125, 80, 81, 85, 86, and 92 are substituted with different amino acids;

(am) an interleukin-2 analog, wherein the interleukin-2 analog is native interleukin-2 in which the amino acid at position 1 is removed and the amino acids at positions 125, 38, 42, 45, 74, 81, and 92 are substituted with different amino acids;

(an) an interleukin-2 analog, wherein the interleukin-2 analog is native interleukin-2 in which the amino acid at position 1 is removed and the amino acids at positions 125, 38, 42, 74, 80, 81, and 92 are substituted with different amino acids;

(ao) an interleukin-2 analog, wherein the interleukin-2 analog is native interleukin-2 in which the amino acid at position 1 is removed and the amino acids at positions 125, 38, 42, 80, 81, 84, and 92 are substituted with different amino acids;

(ap) an interleukin-2 analog, wherein the interleukin-2 analog is native interleukin-2 in which the amino acid at position 1 is removed and the amino acids at positions 125, 38, 45, 80, 85, 86, and 92 are substituted with different amino acids;

(aq) an interleukin-2 analog, wherein the interleukin-2 analog is native interleukin-2 in which the amino acid at position 1 is removed and the amino acids at positions 125, 38, 80, 81, 85, 86, and 92 are substituted with different amino acids;

(ar) an interleukin-2 analog, wherein the interleukin-2 analog is native interleukin-2 in which the amino acid at position 1 is removed and the amino acids at positions 125, 42, 80, 81, 85, 86, and 92 are substituted with different amino acids;

(as) an interleukin-2 analog, wherein the interleukin-2 analog is native interleukin-2 in which the amino acid at position 1 is removed and the amino acids at positions 125, 61, 80, 81, 85, 86, and 92 are substituted with different amino acids;

(at) an interleukin-2 analog, wherein the interleukin-2 analog is native interleukin-2 in which the amino acid at position 1 is removed and the amino acids at positions 125, 69, 80, 81, 85, 86, and 92 are substituted with different amino acids;

(au) an interleukin-2 analog, wherein the interleukin-2 analog is native interleukin-2 in which the amino acid at position 1 is removed and the amino acids at positions 125, 80, 81, 85, 86, 91, and 92 are substituted with different amino acids;

(av) an interleukin-2 analog, wherein the interleukin-2 analog is native interleukin-2 in which the amino acid at position 1 is removed and the amino acids at positions 125, 18, 22, 80, 81, 85, 86, and 92 are substituted with different amino acids;

(aw) an interleukin-2 analog, wherein the interleukin-2 analog is native interleukin-2 in which the amino acid at position 1 is removed and the amino acids at positions 125, 38, 42, 80, 81, 85, 86, and 92 are substituted with different amino acids;

(ax) an interleukin-2 analog, wherein the interleukin-2 analog is native interleukin-2 in which the amino acid at position 1 is removed and the amino acids at positions 125, 38, 42, 45, 74, 80, 81, and 92 are substituted with different amino acids;

(ay) an interleukin-2 analog, wherein the interleukin-2 analog is native interleukin-2 in which the amino acid at position 1 is removed and the amino acids at positions 125, 38, 68, 80, 81, 85, 86, and 92 are substituted with different amino acids;

(az) an interleukin-2 analog, wherein the interleukin-2 analog is native interleukin-2 in which the amino acid at position 1 is removed and the amino acids at positions 125, 69, 74, 80, 81, 85, 86, and 92 are substituted with different amino acids;

(ba) an interleukin-2 analog, wherein the interleukin-2 analog is native interleukin-2 in which the amino acid at position 1 is removed and the amino acids at positions 125, 80, 81, 84, 85, 86, 91, and 92 are substituted with different amino acids;

(bb) an interleukin-2 analog, wherein the interleukin-2 analog is native interleukin-2 in which the amino acid at position 1 is removed and the amino acids at positions 125, 80, 81, 85, 86, 92, 94, and 96 are substituted with different amino acids;

(bc) an interleukin-2 analog, wherein the interleukin-2 analog is native interleukin-2 in which the amino acid at position 1 is removed and the amino acids at positions 125, 18, 19, 22, 80, 81, 85, 86, and 92 are substituted with different amino acids;

(bd) an interleukin-2 analog, wherein the interleukin-2 analog is native interleukin-2 in which the amino acid at position 1 is removed and the amino acids at positions 125, 18, 22, 38, 80, 81, 85, 86, and 92 are substituted with different amino acids;

(be) an interleukin-2 analog, wherein the interleukin-2 analog is native interleukin-2 in which the amino acid at position 1 is removed and the amino acids at positions 125, 18, 22, 61, 80, 81, 85, 86, and 92 are substituted with different amino acids;

(bf) an interleukin-2 analog, wherein the interleukin-2 analog is native interleukin-2 in which the amino acid at position 1 is removed and the amino acids at positions 125, 18, 22, 68, 80, 81, 85, 86, and 92 are substituted with different amino acids;

(bg) an interleukin-2 analog, wherein the interleukin-2 analog is native interleukin-2 in which the amino acid at position 1 is removed and the amino acids at positions 125, 35, 38, 42, 80, 81, 85, 86, and 92 are substituted with different amino acids;

(bh) an interleukin-2 analog, wherein the interleukin-2 analog is native interleukin-2 in which the amino acid at position 1 is removed and the amino acids at positions 125, 38, 42, 45, 80, 81, 85, 86, and 92 are substituted with different amino acids;

(bi) an interleukin-2 analog, wherein the interleukin-2 analog is native interleukin-2 in which the amino acid at position 1 is removed and the amino acids at positions 125, 38, 42, 80, 81, 85, 86, 91, and 92 are substituted with different amino acids;
(bj) an interleukin-2 analog, wherein the interleukin-2 analog is native interleukin-2 in which the amino acid at position 1 is removed and the amino acids at positions 125, 38, 42, 80, 81, 85, 86, 92, and 95 are substituted with different amino acids;
(bk) an interleukin-2 analog, wherein the interleukin-2 analog is native interleukin-2 in which the amino acid at position 1 is removed and the amino acids at positions 125, 35, 38, 42, 74, 80, 81, 85, 86, and 92 are substituted with different amino acids;
(bl) an interleukin-2 analog, wherein the interleukin-2 analog is native interleukin-2 in which the amino acid at position 1 is removed and the amino acids at positions 125, 38, 42, 43, 61, 80, 81, 85, 86, and 92 are substituted with different amino acids;
(bm) an interleukin-2 analog, wherein the interleukin-2 analog is native interleukin-2 in which the amino acid at position 1 is removed and the amino acids at positions 125, 38, 42, 80, 81, 85, 86, 91, 92, and 95 are substituted with different amino acids;
(bn) an interleukin-2 analog, wherein the interleukin-2 analog is native interleukin-2 in which the amino acid at position 1 is removed and the amino acids at positions 125, 35, 38, 42, 74, 80, 81, 82, 85, 86, and 92 are substituted with different amino acids;
(bo) an interleukin-2 analog, wherein the interleukin-2 analog is native interleukin-2 in which the amino acid at position 1 is removed and the amino acids at positions 125, 80, 81, 86, and 92 are substituted with different amino acids; and
(bp) an interleukin-2 analog, wherein the interleukin-2 analog is native interleukin-2 in which the amino acid at position 1 is removed and the amino acids at positions 125, 80, 81, 85, and 86 are substituted with different amino acids.

In particular, the amino acid substitutions included in the interleukin-2 analog may be any one or more selected from the group consisting of the following amino acid substitutions:
(a) a substitution in which the amino acid at position 12 is substituted with valine or phenylalanine;
(b) a substitution in which the amino acid at position 18 is substituted with arginine;
(c) a substitution in which the amino acid at position 19 is substituted with tyrosine, valine, phenylalanine, or arginine;
(d) a substitution in which the amino acid at position 20 is substituted with valine or phenylalanine;
(e) a substitution in which the amino acid at position 22 is substituted with glutamic acid;
(f) a substitution in which the amino acid at position 32 is substituted with cysteine;
(g) a substitution in which the amino acid at position 35 is substituted with cysteine or glutamic acid;
(h) a substitution in which the amino acid at position 38 is substituted with alanine or aspartic acid;
(i) a substitution in which the amino acid at position 42 is substituted with lysine, alanine, or tryptophan;
(j) a substitution in which the amino acid at position 43 is substituted with cysteine, glutamic acid, or glutamine;
(k) a substitution in which the amino acid at position 45 is substituted with alanine;
(l) a substitution in which the amino acid at position 48 is substituted with cysteine;
(m) a substitution in which the amino acid at position 49 is substituted with cysteine;
(n) a substitution in which the amino acid at position 61 is substituted with glutamine, arginine, or aspartic acid;
(o) a substitution in which the amino acid at position 68 is substituted with aspartic acid or glutamine;
(p) a substitution in which the amino acid at position 69 is substituted with glycine;
(q) a substitution in which the amino acid at position 74 is substituted with histidine or alanine;
(r) a substitution in which the amino acid at position 76 is substituted with cysteine;
(s) a substitution in which the amino acid at position 80 is substituted with phenylalanine, tyrosine, valine, aspartic acid, or tryptophan;
(t) a substitution in which the amino acid at position 81 is substituted with aspartic acid, glutamic acid, or asparagine;
(u) a substitution in which the amino acid at position 82 is substituted with glycine or valine;
(v) a substitution in which the amino acid at position 84 is substituted with glutamic acid, valine, or phenylalanine;
(w) a substitution in which the amino acid at position 85 is substituted with valine, alanine, glycine, tryptophan, tyrosine, threonine, isoleucine, glutamic acid, or phenylalanine;
(x) a substitution in which the amino acid at position 86 is substituted with valine, alanine, glycine, or leucine;
(y) a substitution in which the amino acid at position 87 is substituted with cysteine;
(z) a substitution in which the amino acid at position 88 is substituted with glutamine, valine, or phenylalanine;
(aa) a substitution in which the amino acid at position 89 is substituted with phenylalanine;
(ab) a substitution in which the amino acid at position 91 is substituted with threonine, phenylalanine, or glutamic acid;
(ac) a substitution in which the amino acid at position 92 is substituted with phenylalanine, leucine, tyrosine, or tryptophan;
(ad) a substitution in which the amino acid at position 95 is substituted with aspartic acid;
(ae) a substitution in which the amino acid at position 96 is substituted with phenylalanine, valine, or isoleucine; and
(af) a substitution in which the amino acid at position 126 is substituted with threonine.

As used herein, the term "corresponding to" refers to an amino acid residue at a position listed in a peptide, or an amino acid residue which is similar, identical, or homologous to a residue listed in a peptide. Confirmation of the amino acid at the corresponding position may be determining a specific amino acid in a sequence that refers to a specific sequence.

In an embodiment, each amino acid residue in the amino acid sequence can be numbered by aligning any amino acid sequence with SEQ ID NO: 1, and based on the same, referring to the numerical position of the amino acid residue corresponding to the amino acid residue of SEQ ID NO: 1.

As such an alignment, for example, the Needleman-Wunsch algorithm (Needleman and Wunsch, 1970, *J. Mol. Biol.* 48:443-453), the Needle program of the EMBOSS package (EMBOSS: The European Molecular Biology Open Software Suite, Rice et al., 2000), (*Trends Genet.* 16:276-277), etc. may be used, but the available programs are not limited thereto, and a sequence alignment program known in the art, a pairwise sequence comparison algorithm, etc. may be used appropriately.

In the present invention, even if expressed as a specific position of an amino acid in a peptide, such expression may refer to a corresponding position in a reference sequence.

In another embodiment, the interleukin-2 analog may include, consist of or essentially consist of an amino acid sequence which is selected from the group consisting of SEQ ID NOS: 3 to 106, but the interleukin-2 analog is not limited thereto.

Additionally, even if the interleukin-2 analog is expressed as "an interleukin-2 analog consisting of a particular SEQ ID NO" in the present invention, it does not exclude a mutation that may occur by the addition of a meaningless sequence upstream or downstream of the amino acid sequence of the corresponding SEQ ID NO, or a mutation that may occur naturally, or a silent mutation thereof, as long as the interleukin-2 analog has an activity identical or equivalent to the interleukin-2 analog consisting of the amino acid sequence of the corresponding SEQ ID NO, and even if the sequence addition or mutation is present, the interleukin-2 analog apparently belongs to the scope of the present invention.

The interleukin-2 analog of the present invention may include an amino acid sequence which has a homology of 40% or higher, 45% or higher, 50% or higher, 55% or higher, 60% or higher, 65% or higher, 70% or higher, 75% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher to the amino acid sequences of SEQ ID NOS: 3 to 106, but the interleukin-2 analog is not limited thereto.

In the present invention, the terms "homology" and "identity" refer to a degree of relatedness between two given amino acid sequences or nucleotide sequences and may be expressed as a percentage.

Sequence homology or identity of a conserved polynucleotide or polypeptide may be determined by a standard alignment algorithm, and default gap penalties established by a program to be used may be used in combination. Substantially, homologous or identical sequences may generally hybridize with all or part of the sequences under moderately or highly stringent conditions. It is apparent that hybridization also includes hybridization of a polynucleotide with a polynucleotide, which includes a general codon or a codon where codon degeneracy is considered.

The terms homology and identity can frequently be used interchangeably.

Whether any two nucleotide or peptide sequences have homology, similarity, or identity may be determined by, for example, a known computer algorithm (e.g., the "FASTA" program) using default parameters as in Pearson et al. (1988) *Proc. Natl. Acad. Sci. USA* 85:2444). Alternatively, they may be determined using the Needleman-Wunsch algorithm (Needleman and Wunsch, 1970, *J. Mol. Biol.* 48:443-453) as performed in the Needleman program of the EMBOSS package (EMBOSS: The European Molecular Biology Open Software Suite, Rice et al., 2000, *Trends Genet.* 16:276-277) (version 5.0.0 or later) (including GCG program package (Devereux, J. et al., *Nucleic Acids Research* 12:387 (1984)), BLASTP, BLASTN, FASTA (Atschul, S. F. et al., *J Molec Biol* 215:403 (1990); *Guide to Huge Computers*, Martin J. Bishop, ed., Academic Press, San Diego, 1994, and CARILLO et al. (1988) *SIAM J Applied Math* 48:1073). For example, homology, similarity, or identity may be determined using BLAST or ClustalW of the National Center for Biotechnology Information.

Homology, similarity, or identity of nucleotide or peptide sequences may be determined by comparing sequence information using the GAP computer program (e.g., Needleman et al. (1970), *J Mol Biol* 48:443) as disclosed in Smith and Waterman, *Adv. Appl. Math* (1981) 2:482. Briefly, the GAP program defines homology, similarity, or identity as the number of similar aligned symbols (i.e., nucleotides or amino acids), divided by the total number of symbols in the shorter of the two sequences. The default parameters for the GAP program may include: (1) a unary comparison matrix (containing a value of 1 for identities and 0 for non-identities) and the weighted comparison matrix (or EDNAFULL (EMBOSS version of NCBI NUC4.4) substitution matrix) of Gribskov et al. (1986) *Nucl. Acids Res.* 14:6745, as disclosed by Schwartz and Dayhoff, eds., *Atlas Of Protein Sequence And Structure*, National Biomedical Research Foundation, pp. 353-358 (1979); (2) a penalty of 3.0 for each gap and an additional 0.10 penalty for each symbol in each gap (or gap open penalty 10, gap extension penalty 0.5); and (3) no penalty for end gaps. Therefore, the terms "homology" and "identity", as used herein, represent relevance between sequences.

The above may be applied to other embodiments or other aspects of the present invention, but is not limited thereto.

The interleukin-2 analog of the present invention may be used as a novel interleukin-2 substitute that alters its in vitro activity by weakening or increasing the binding affinity of the interleukin-2 analog for interleukin-2 alpha and/or beta receptors. In particular, the interleukin-2 analog of the present invention can be used as an effective therapeutic agent due to its activities for the two types of receptors because it not only has an increased binding affinity for beta receptors but also has altered (i.e., increased or decreased) binding affinity for alpha receptors.

In the present invention, such modification for preparing analogs of interleukin-2 includes all of the modifications using L-type or D-type amino acids and/or non-natural amino acids; and/or a modification of native sequence, for example, a modification of a side chain functional group, an intramolecular covalent bonding (e.g., a ring formation between side chains), methylation, acylation, ubiquitination, phosphorylation, aminohexanation, biotinylation, etc.

Additionally, the modification includes all of those where one or more amino acids are added to the amino and/or carboxy terminus of native interleukin-2.

As the amino acids to be substituted or added, not only the 20 amino acids commonly observed in human proteins, but also atypical amino acids or those which are not naturally occurring can be used. Commercial sources of atypical amino acids include Sigma-Aldrich, Chem Pep Inc., and Genzyme Pharmaceuticals. The peptides including these amino acids and typical peptide sequences may be synthesized and purchased from commercial suppliers, e.g., American Peptide Company, Bachem (USA), or Anygen (Korea).

Amino acid derivatives may be obtained in the same manner, and as one such example, 4-imidazoacetic acid, etc. may be used.

Additionally, the interleukin-2 analog according to the present invention may be in a modified form where the N-terminus and/or C-terminus, etc. of the interleukin-2 is chemically modified or protected by organic groups, or amino acids may be added to the terminus of the peptide, etc. for its protection from proteases in vivo while increasing its stability.

In particular, in the case of a chemically synthesized peptide, its N- and C-termini are electrically charged, and thus the N-terminus of the peptide may be acetylated and/or C-terminus of the peptide may be amidated, but the peptide is not particularly limited thereto.

Additionally, since the interleukin-2 analog according to the present invention is in a peptide form, it may include all of those in the form of the peptide itself, a salt thereof (e.g., a pharmaceutically acceptable salt of the peptide), or a solvate thereof. Additionally, the peptide may be in any pharmaceutically acceptable form.

The kind of the salt is not particularly limited. However, it is desirable that the salt be in a safe and effective form for a subject (e.g., a mammal), but the salt type is not particularly limited thereto.

The term "pharmaceutically acceptable" refers to a material which can be effectively used for a desired purpose without causing excessive toxicity, irritation, allergic reactions, etc. within the scope of medical judgment.

As used herein, the term "pharmaceutically acceptable salt" includes salts which are derived from pharmaceutically acceptable inorganic acids, organic acids, or bases. Examples of suitable acids include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Salts derived from suitable bases may include alkali metals (e.g., sodium, potassium, etc.), alkaline earth metals (e.g., magnesium, etc.), ammonium, etc.

Additionally, as used herein, the term "solvate" refers to a complex formed between the peptide according to the present invention or a salt thereof and a solvent molecule.

In the present invention, the binding affinity of any interleukin-2 analog for native interleukin-2 receptors can be measured using various known techniques, which are methods for measuring the affinity for the receptors. For example, surface plasmon resonance (SPR) may be used, but the measurement method is not limited thereto.

More specifically, the interleukin-2 analog of the present invention may have reduced or increased binding affinity for interleukin-2 alpha receptors compared to native interleukin-2 or aldesleukin.

Specifically, the interleukin-2 analog of the present invention may have binding affinity for interleukin-2 alpha receptors of about 0.001-fold or greater, about 0.005-fold or greater, about 0.01-fold or greater, about 0.05-fold or greater, about 0.1-fold or greater, about 0.3-fold or greater, about 0.5-fold or greater, about 0.7-fold or about 0.9-fold or greater, about 1.1-fold or greater, about 1.3-fold or greater, about 1.5-fold or greater, or about 1.7-fold or greater compared to the binding affinity of native interleukin-2 or aldesleukin for interleukin-2 alpha receptors, but the numerical value of the binding affinity is not limited, and the value will belong to the scope of the present invention as long as there is a change in the binding affinity compared to that of native interleukin-2 or aldesleukin.

Alternatively, based on the binding affinity of aldesleukin for interleukin-2 alpha receptors (set at 100%), the interleukin-2 analog of the present invention may have no binding affinity for interleukin-2 alpha receptors or have binding affinity for interleukin-2 alpha receptors of about 1% or greater, about 5% or greater, about 7% or greater, about 10% or greater, about 15% or greater, about 20% or greater, about 30% or greater, about 50% or greater, about 70% or greater, about 90% or greater, about 100% or greater, about 150% or greater, or about 200% or greater, but the numerical value of the binding affinity is not limited, and the value will belong to the scope of the present invention as long as there is a change in the binding affinity compared to that of native interleukin-2 or aldesleukin.

Additionally, the interleukin-2 analog of the present invention may specifically have binding affinity for interleukin-2 beta receptors of about 0.1-fold or greater, about 0.3-fold or greater, about 0.5-fold or greater, about 0.7-fold or greater, about 1.0-fold or greater, about 10-fold or greater, about 20-fold or greater, about 30-fold or greater, about 40-fold or greater, about 50-fold or greater, about 60-fold or greater, about 70-fold or greater, about 80-fold or greater, about 90-fold or greater, or about 100-fold or greater compared to the binding affinity of native interleukin-2 or aldesleukin for interleukin-2 beta receptors, but the numerical value of the binding affinity is not limited, and the value will belong to the scope of the present invention as long as there is a change or increase in the binding affinity compared to that of native interleukin-2 or aldesleukin.

Alternatively, based on the binding affinity of aldesleukin for interleukin-2 beta receptors (set at 100%), the interleukin-2 analog of the present invention may have binding affinity for interleukin-2 beta receptors of about 5% or greater, about 9% or greater, about 10% or greater, about 20% or greater, about 30% or greater, about 50% or greater, about 100% or greater, about 200% or greater, about 500% or greater, about 700% or greater, about 1,000% or greater, about 1,500% or greater, about 3,000% or greater, about 5,000% or greater, about 7,000% or greater, about 10,000% or greater, about 12,000% or greater, about 15,000% or greater, about 20,000% or greater, or about 25,000%, but the numerical value of the binding affinity is not limited, and the value will belong to the scope of the present invention as long as there is an increase in the binding affinity compared to that of native interleukin-2 or aldesleukin.

As used herein, the term "about" refers to a range which includes all of ±0.5, ±0.4, ±0.3, ±0.2, ±0.1, etc. and includes all of the values that are equivalent or similar to those following the values, but the range is not limited thereto.

The interleukin-2 analog of the present invention is characterized in that it has altered binding affinity for interleukin-2 alpha receptors and increased binding affinity for interleukin-2 beta receptors compared to native interleukin-2 or aldesleukin.

In a specific embodiment of the present invention, for the preparation of the interleukin-2 analog of the present invention, an interleukin-2 analog was prepared into which a modification was introduced based on native interleukin-2 (SEQ ID NO: 1). The interleukin-2 analog prepared in the present invention may be one which includes any one amino acid sequence among SEQ ID NOS: 3 to 106, or may be one which is encoded by any one nucleotide sequence among SEQ ID NOS: 108 to 211.

Still another aspect to implement the present invention provides a nucleic acid (polynucleotide) encoding the interleukin-2 analog, a recombinant expression vector including the nucleic acid, and a transformant which includes the nucleic acid or recombinant expression vector.

The nucleic acid encoding the interleukin-2 analog of the present invention may be one which is modified so that a modification (deletion, substitution, and/or addition of an amino acid) can be introduced into an amino acid at a particular position in a native interleukin-2 of SEQ ID NO: 1, and specifically, the interleukin-2 analog of the present invention may include a nucleotide sequence encoding any one amino acid sequence among SEQ ID NOS: 3 to 106. For example, the nucleic acid of the present invention may have or include a nucleotide sequence of any one among SEQ ID NOS: 108 to 211.

The nucleotide sequence of the present invention may be modified variously in the coding region within a range not altering the amino acid sequence of the interleukin-2 analog of the present invention, considering codon degeneracy or the codons preferred in the organism where the nucleic acid of the present invention is to be expressed. Specifically, the nucleic acid of the present invention may have or include a nucleotide sequence which has a homology or identity of 70% or higher, 75% or higher, 80% or higher, 85% or higher, 90% or higher, 95% or higher, 96% or higher, 97% or higher, 98% or higher, and less than 100% to any one of the sequences of SEQ ID NOS: 108 to 211; or may consist of or essentially consist of a nucleotide sequence which has a homology or identity of 70% or higher, 75% or higher, 80% or higher, 85% or higher, 90% or higher, 95% or higher, 96% or higher, 97% or higher, 98% or higher, and less than 100% to any one of the sequences of SEQ ID NOS: 108 to 211, but the nucleic acid is not limited thereto.

Additionally, the nucleic acid of the present invention can include, without limitation, a probe which can be prepared from a known gene sequence (e.g., a sequence that can hybridize with a sequence complementary to all or part of the nucleic acid sequence of the present invention under stringent conditions). The "stringent conditions" refer to conditions that enable specific hybridization between polynucleotides. Such conditions are described in detail in the literature (see J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*, John Wiley & Sons, Inc., New York, 9.50-9.51, 11.7-11.8).

Hybridization requires that two nucleic acids have complementary sequences, although mismatches between bases may be possible depending on hybridization stringency. The term "complementary" is used to describe the relationship between nucleotide bases that can hybridize to each other. For example, with respect to DNA, adenine is complementary to thymine, and cytosine is complementary to guanine. Accordingly, the nucleic acid of the present invention can include isolated nucleic acid fragments complementary to the entire sequence as well as to substantially similar nucleic acid sequences.

The appropriate stringency for hybridizing polynucleotides depends on the length of the polynucleotides and the degree of complementarity, and variables are well known in the art (e.g., Sambrook et al., supra).

The homology and identity are as described above.

The recombination vector according to the present invention may be constructed as a vector for typical cloning or a vector for expression, and may be constructed as a vector for use of eukaryotic or prokaryotic cells as a host cell.

As used herein, the term "vector", which is a recombination vector capable of expressing a target protein in an appropriate host cell, refers to a nucleic acid construct that includes essential control elements operably linked to enable the expression of the nucleic acid insert. In the present invention, it is possible to prepare a recombination vector which includes a nucleic acid encoding an interleukin-2 analog, and the interleukin-2 analog of the present invention can be obtained by transforming or transfecting a host cell with the recombination vector.

As used herein, the term "transformation" refers to a phenomenon in which DNA is introduced into a host cell to allow DNA to be replicated as a factor of a chromosome or by completion of chromosome integration, and external DNA is introduced into cells to artificially cause genetic changes.

The host suitable for the present invention is not particularly limited as long as it enables the expression of the nucleic acid of the present invention. Specific examples of the host that can be used in the present invention include bacteria of the genus *Escherichia* (e.g., *E. coli*); bacteria of the genus *Bacillus* (e.g., *Bacillus subtilis*); bacteria of the genus *Pseudomonas* (e.g., *Pseudomonas putida*); yeasts (e.g., *Pichia pastoris, Saccharomyces cerevisiae,* and *Schizosaccharomyces pombe*); insect cells (e.g., *Spodoptera frugiperda* (SF9)); and animal cells (e.g., CHO, COS, BSC, etc.).

Still another aspect to implement the present invention provides a method for preparing an interleukin-2 analog which includes one or more modifications.

Specifically, the method may include introducing a modification into one or more amino acids selected from the group consisting of amino acids corresponding to those at positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2.

More specifically, the method may be:
(a) a method, wherein in native interleukin-2, the amino acid at position 1 is removed and the amino acids at positions 125 and 32 are substituted with different amino acids;
(b) a method, wherein in native interleukin-2, the amino acid at position 1 is removed and the amino acids at positions 125 and 35 are substituted with different amino acids;
(c) a method, wherein in native interleukin-2, the amino acid at position 1 is removed and the amino acids at positions 125 and 38 are substituted with different amino acids;
(d) a method, wherein in native interleukin-2, the amino acid at position 1 is removed and the amino acids at positions 125 and 42 are substituted with different amino acids;
(e) a method, wherein in native interleukin-2, the amino acid at position 1 is removed and the amino acids at positions 125 and 43 are substituted with different amino acids;
(f) a method, wherein in native interleukin-2, the amino acid at position 1 is removed and the amino acids at positions 125 and 48 are substituted with different amino acids;
(g) a method, wherein in native interleukin-2, the amino acid at position 1 is removed and the amino acids at positions 125 and 49 are substituted with different amino acids;
(h) a method, wherein in native interleukin-2, the amino acid at position 1 is removed and the amino acids at positions 125 and 76 are substituted with different amino acids;
(i) a method, wherein in native interleukin-2, the amino acid at position 1 is removed and the amino acids at positions 125, 38, 42, 81, 92, 94, and 96 are substituted with different amino acids;
(j) a method, wherein in native interleukin-2, the amino acid at position 1 is removed and the amino acids at positions 125 and 87 are substituted with different amino acids;

(k) a method, wherein in native interleukin-2, the amino acid at position 1 is removed and the amino acids at positions 125, 38, and 42 are substituted with different amino acids;

(l) a method, wherein in native interleukin-2, the amino acid at position 1 is removed and the amino acids at positions 125, 38, and 80 are substituted with different amino acids;

(m) a method, wherein in native interleukin-2, the amino acid at position 1 is removed and the amino acids at positions 125, 38, and 84 are substituted with different amino acids;

(n) a method, wherein in native interleukin-2, the amino acid at position 1 is removed and the amino acids at positions 125, 19, 38, and 42 are substituted with different amino acids;

(o) a method, wherein in native interleukin-2, the amino acid at position 1 is removed and the amino acids at positions 125, 12, 38, and 42 are substituted with different amino acids;

(p) a method, wherein in native interleukin-2, the amino acid at position 1 is removed and the amino acids at positions 125, 38, 42, and 61 are substituted with different amino acids;

(q) a method, wherein in native interleukin-2, the amino acid at position 1 is removed and the amino acids at positions 125, 38, 42, and 84 are substituted with different amino acids;

(r) a method, wherein in native interleukin-2, the amino acid at position 1 is removed and the amino acids at positions 125, 38, 42, and 88 are substituted with different amino acids;

(s) a method, wherein in native interleukin-2, the amino acid at position 1 is removed and the amino acids at positions 125, 38, 42, and 89 are substituted with different amino acids;

(t) a method, wherein in native interleukin-2, the amino acid at position 1 is removed and the amino acids at positions 125, 38, 42, and 91 are substituted with different amino acids;

(u) a method, wherein in native interleukin-2, the amino acid at position 1 is removed and the amino acids at positions 125, 38, 42, and 94 are substituted with different amino acids;

(v) a method, wherein in native interleukin-2, the amino acid at position 1 is removed and the amino acids at positions 125, 38, 42, and 126 are substituted with different amino acids;

(w) a method, wherein in native interleukin-2, the amino acid at position 1 is removed and the amino acids at positions 125, 38, 80, and 84 are substituted with different amino acids;

(x) a method, wherein in native interleukin-2, the amino acid at position 1 is removed and the amino acids at positions 125, 38, 94, and 96 are substituted with different amino acids;

(y) a method, wherein in native interleukin-2, the amino acid at position 1 is removed and the amino acids at positions 125, 38, 81, and 92 are substituted with different amino acids;

(z) a method, wherein in native interleukin-2, the amino acid at position 1 is removed and the amino acids at positions 125, 61, 81, and 92 are substituted with different amino acids;

(aa) a method, wherein in native interleukin-2, the amino acid at position 1 is removed and the amino acids at positions 125, 38, 42, 81, and 92 are substituted with different amino acids;

(ab) a method, wherein in native interleukin-2, the amino acid at position 1 is removed and the amino acids at positions 125, 38, 80, 81, and 92 are substituted with different amino acids;

(ac) a method, wherein in native interleukin-2, the amino acid at position 1 is removed and the amino acids at positions 125, 38, 81, 84, and 92 are substituted with different amino acids;

(ad) a method, wherein in native interleukin-2, the amino acid at position 1 is removed and the amino acids at positions 125, 20, 38, 42, 81, and 92 are substituted with different amino acids;

(ae) a method, wherein in native interleukin-2, the amino acid at position 1 is removed and the amino acids at positions 125, 38, 42, 80, 81, and 92 are substituted with different amino acids;

(af) a method, wherein in native interleukin-2, the amino acid at position 1 is removed and the amino acids at positions 125, 38, 42, 74, 81, and 92 are substituted with different amino acids;

(ag) a method, wherein in native interleukin-2, the amino acid at position 1 is removed and the amino acids at positions 125, 38, 42, 81, 84, and 92 are substituted with different amino acids;

(ah) a method, wherein in native interleukin-2, the amino acid at position 1 is removed and the amino acids at positions 125, 38, 42, 81, 88, and 92 are substituted with different amino acids;

(ai) a method, wherein in native interleukin-2, the amino acid at position 1 is removed and the amino acids at positions 125, 38, 42, 85, 86, and 92 are substituted with different amino acids;

(aj) a method, wherein in native interleukin-2, the amino acid at position 1 is removed and the amino acids at positions 125, 38, 80, 81, 85, and 92 are substituted with different amino acids;

(ak) a method, wherein in native interleukin-2, the amino acid at position 1 is removed and the amino acids at positions 125, 38, 80, 81, 86, and 92 are substituted with different amino acids;

(al) a method, wherein in native interleukin-2, the amino acid at position 1 is removed and the amino acids at positions 125, 80, 81, 85, 86, and 92 are substituted with different amino acids;

(am) a method, wherein in native interleukin-2, the amino acid at position 1 is removed and the amino acids at positions 125, 38, 42, 45, 74, 81, and 92 are substituted with different amino acids;

(an) a method, wherein in native interleukin-2, the amino acid at position 1 is removed and the amino acids at positions 125, 38, 42, 74, 80, 81, and 92 are substituted with different amino acids;

(ao) a method, wherein in native interleukin-2, the amino acid at position 1 is removed and the amino acids at positions 125, 38, 42, 80, 81, 84, and 92 are substituted with different amino acids;

(ap) a method, wherein in native interleukin-2, the amino acid at position 1 is removed and the amino acids at positions 125, 38, 45, 80, 85, 86, and 92 are substituted with different amino acids;

(aq) a method, wherein in native interleukin-2, the amino acid at position 1 is removed and the amino acids at positions 125, 38, 80, 81, 85, 86, and 92 are substituted with different amino acids;

(ar) a method, wherein in native interleukin-2, the amino acid at position 1 is removed and the amino acids at positions 125, 42, 80, 81, 85, 86, and 92 are substituted with different amino acids;

(as) a method, wherein in native interleukin-2, the amino acid at position 1 is removed and the amino acids at positions 125, 61, 80, 81, 85, 86, and 92 are substituted with different amino acids;

(at) a method, wherein in native interleukin-2, the amino acid at position 1 is removed and the amino acids at positions 125, 69, 80, 81, 85, 86, and 92 are substituted with different amino acids;

(au) a method, wherein in native interleukin-2, the amino acid at position 1 is removed and the amino acids at positions 125, 80, 81, 85, 86, 91, and 92 are substituted with different amino acids;

(av) a method, wherein in native interleukin-2, the amino acid at position 1 is removed and the amino acids at positions 125, 18, 22, 80, 81, 85, 86, and 92 are substituted with different amino acids;

(aw) a method, wherein in native interleukin-2, the amino acid at position 1 is removed and the amino acids at positions 125, 38, 42, 80, 81, 85, 86, and 92 are substituted with different amino acids;

(ax) a method, wherein in native interleukin-2, the amino acid at position 1 is removed and the amino acids at positions 125, 38, 42, 45, 74, 80, 81, and 92 are substituted with different amino acids;

(ay) a method, wherein in native interleukin-2, the amino acid at position 1 is removed and the amino acids at positions 125, 38, 68, 80, 81, 85, 86, and 92 are substituted with different amino acids;

(az) a method, wherein in native interleukin-2, the amino acid at position 1 is removed and the amino acids at positions 125, 69, 74, 80, 81, 85, 86, and 92 are substituted with different amino acids;

(ba) a method, wherein in native interleukin-2, the amino acid at position 1 is removed and the amino acids at positions 125, 80, 81, 84, 85, 86, 91, and 92 are substituted with different amino acids;

(bb) a method, wherein in native interleukin-2, the amino acid at position 1 is removed and the amino acids at positions 125, 80, 81, 85, 86, 92, 94, and 96 are substituted with different amino acids;

(bc) a method, wherein in native interleukin-2, the amino acid at position 1 is removed and the amino acids at positions 125, 18, 19, 22, 80, 81, 85, 86, and 92 are substituted with different amino acids;

(bd) a method, wherein in native interleukin-2, the amino acid at position 1 is removed and the amino acids at positions 125, 18, 22, 38, 80, 81, 85, 86, and 92 are substituted with different amino acids;

(be) a method, wherein in native interleukin-2, the amino acid at position 1 is removed and the amino acids at positions 125, 18, 22, 61, 80, 81, 85, 86, and 92 are substituted with different amino acids;

(bf) a method, wherein in native interleukin-2, the amino acid at position 1 is removed and the amino acids at positions 125, 18, 22, 68, 80, 81, 85, 86, and 92 are substituted with different amino acids;

(bg) a method, wherein in native interleukin-2, the amino acid at position 1 is removed and the amino acids at positions 125, 35, 38, 42, 80, 81, 85, 86, and 92 are substituted with different amino acids;

(bh) a method, wherein in native interleukin-2, the amino acid at position 1 is removed and the amino acids at positions 125, 38, 42, 45, 80, 81, 85, 86, and 92 are substituted with different amino acids;

(bi) a method, wherein in native interleukin-2, the amino acid at position 1 is removed and the amino acids at positions 125, 38, 42, 80, 81, 85, 86, 91, and 92 are substituted with different amino acids;

(bj) a method, wherein in native interleukin-2, the amino acid at position 1 is removed and the amino acids at positions 125, 38, 42, 80, 81, 85, 86, 92, and 95 are substituted with different amino acids;

(bk) a method, wherein in native interleukin-2, the amino acid at position 1 is removed and the amino acids at positions 125, 35, 38, 42, 74, 80, 81, 85, 86, and 92 are substituted with different amino acids;

(bl) a method, wherein in native interleukin-2, the amino acid at position 1 is removed and the amino acids at positions 125, 38, 42, 43, 61, 80, 81, 85, 86, and 92 are substituted with different amino acids;

(bm) a method, wherein in native interleukin-2, the amino acid at position 1 is removed and the amino acids at positions 125, 38, 42, 80, 81, 85, 86, 91, 92, and 95 are substituted with different amino acids; or (bn) a method, wherein in native interleukin-2, the amino acid at position 1 is removed and the amino acids at positions 125, 35, 38, 42, 74, 80, 81, 82, 85, 86, and 92 are substituted with different amino acids, (bo) a method, wherein in native interleukin-2, the amino acid at position 1 is removed and the amino acids at positions 125, 80, 81, 86, and 92 are substituted with different amino acids; or (bp) a method, wherein in native interleukin-2, the amino acid at position 1 is removed and the amino acids at positions 125, 80, 81, 85, and 86 are substituted with different amino acids;

but the method is not limited thereto.

The interleukin-2 analog and modification are the same as above.

In another embodiment of a method for preparing the interleukin-2 analog of the present invention, the method for preparing the interleukin-2 analog may include (a) culturing a transformant which includes a nucleic acid encoding the interleukin-2 analog and expressing the interleukin-2 analog; and (b) isolating and purifying the expressed interleukin-2 analog, but the method is not limited to any particular method, and any method known in the art may be used as long as the interleukin-2 analog can be prepared by the same.

In the present invention, the nucleic acid encoding the interleukin-2 analog may include or (essentially) consist of any one nucleotide sequence among SEQ ID NOS: 108 to 211.

The medium used for culturing a transformant in the present invention must meet the requirements for culturing host cells in an appropriate manner. The carbon sources that can be included in the medium for the growth of host cells can be appropriately selected as a decision by those skilled in the art according to the type of transformants being produced, and appropriate culture conditions can be adopted to control the time and amount of culture.

Sugar sources that can be used may include sugars and carbohydrates (e.g., glucose, saccharose, lactose, fructose, maltose, starch, and cellulose); oils and fats (e.g., soybean oil, sunflower oil, castor oil, coconut oil, etc.); fatty acids (e.g., palmitic acid, stearic acid, and linoleic acid); alcohols (e.g., glycerol and ethanol); and organic acids (e.g., acetic acid). These materials can be used individually or as a mixture.

Nitrogen sources that can be used may include peptone, yeast extract, gravy, malt extract, corn steep liquor, soybean meal, and urea, or inorganic compounds (e.g., ammonium sulfate, ammonium chloride, ammonium phosphate, ammonium carbonate, and ammonium nitrate). Nitrogen sources can also be used individually or as a mixture.

Phosphorous sources that can be used may include potassium dihydrogen phosphate or dipotassium hydrogen phosphate, or corresponding sodium-containing salts thereof. In addition, the culture medium may contain a metal salt (e.g., magnesium sulfate and iron sulfate) required for growth.

Finally, in addition to these materials, essential growth materials (e.g., amino acids and vitamins) may be used. In addition, suitable precursors for culture media may be used. The above-mentioned raw materials can be added in a batch or continuous mode in a manner appropriate to the culture during the cultivation. Basic compounds (e.g., sodium hydroxide, potassium hydroxide, and ammonia) or acidic compounds (e.g., phosphoric acid and sulfuric acid) can be used in an appropriate manner to adjust the pH of the culture. In addition, antifoaming agents (e.g., fatty acid polyglycol esters) may be used to inhibit bubble generation. In order to maintain aerobic conditions, oxygen or oxygen-containing gas (e.g., air) is injected into the culture.

Culturing of the transformant according to the present invention is usually performed at a temperature of 20° C. to 45° C., specifically 25° C. to 40° C. In addition, the culture is continued until the maximum amount of the desired interleukin-2 analog is obtained, and for this purpose, the culture can usually last for 10 to 160 hours.

As described above, if the appropriate culture conditions are established depending on the host cell, the transformant according to the present invention will produce an interleukin-2 analog, and depending on the composition of the vector and the characteristics of the host cell, the interleukin-2 analog produced can be secreted into the cytoplasm of the host cell, into the periplasmic space, or extracellularly.

Proteins expressed in the host cell or outside thereof can be purified in a conventional manner. Examples of purification methods include salting out (e.g.: ammonium sulfate precipitation, sodium phosphate precipitation, etc.), solvent precipitation (e.g., protein fractionation precipitation using acetone, ethanol, etc.), dialysis, gel filtration, ion exchange, chromatography (e.g., reverse-phase column chromatography), ultrafiltration, etc. and can be used alone or in combination.

In a specific embodiment of the present invention, a method for preparing an interleukin-2 analog may include:
 (a) expressing the interleukin-2 analog; and
 (b) isolating the expressed interleukin-2 analog.

In a specific embodiment of the present invention, the following steps may be further included to isolate and purify the interleukin-2 analog expressed in the form of an inclusion body from a transformant:
 (b-1) collecting and disrupting a transformant from the culture medium of the step (a) above;
 (b-2) recovering and refolding an interleukin-2 analog expressed in a disrupted cell lysate; and
 (b-3) purifying the refolded interleukin-2 analog by size-exclusion chromatography.

Still another aspect to implement the present invention provides a method for preparing the interleukin-2 analog by way of a peptide synthesis method. Since the sequences of the interleukin-2 analogs of the present invention are already provided, the synthesis of peptides can be performed using a known peptide synthesis method.

The interleukin-2 analog and modification are as described above.

Still another aspect to implement the present invention provides a method for increasing the binding affinity for interleukin-2 beta receptors, which includes modifying one or more amino acids in native interleukin-2.

The method for increasing the binding affinity for interleukin-2 beta receptors according to the present invention may be one which not only increases the binding affinity for interleukin-2 beta receptors but also alters the binding affinity for interleukin-2 alpha receptors compared to native interleukin-2 or aldesleukin.

Specifically, the method may include a step of introducing a modification into one or more amino acids corresponding to those at positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2.

More specifically, the method may be:
 (a) a method, wherein in native interleukin-2, the amino acid at position 1 is removed and the amino acids at positions 125 and 32 are substituted with different amino acids;
 (b) a method, wherein in native interleukin-2, the amino acid at position 1 is removed and the amino acids at positions 125 and 35 are substituted with different amino acids;
 (c) a method, wherein in native interleukin-2, the amino acid at position 1 is removed and the amino acids at positions 125 and 38 are substituted with different amino acids;
 (d) a method, wherein in native interleukin-2, the amino acid at position 1 is removed and the amino acids at positions 125 and 42 are substituted with different amino acids;
 (e) a method, wherein in native interleukin-2, the amino acid at position 1 is removed and the amino acids at positions 125 and 43 are substituted with different amino acids;
 (f) a method, wherein in native interleukin-2, the amino acid at position 1 is removed and the amino acids at positions 125 and 48 are substituted with different amino acids;
 (g) a method, wherein in native interleukin-2, the amino acid at position 1 is removed and the amino acids at positions 125 and 49 are substituted with different amino acids;
 (h) a method, wherein in native interleukin-2, the amino acid at position 1 is removed and the amino acids at positions 125 and 76 are substituted with different amino acids;
 (i) a method, wherein in native interleukin-2, the amino acid at position 1 is removed and the amino acids at positions 125, 38, 42, 81, 92, 94, and 96 are substituted with different amino acids;
 (j) a method, wherein in native interleukin-2, the amino acid at position 1 is removed and the amino acids at positions 125 and 87 are substituted with different amino acids;
 (k) a method, wherein in native interleukin-2, the amino acid at position 1 is removed and the amino acids at positions 125, 38, and 42 are substituted with different amino acids;

(l) a method, wherein in native interleukin-2, the amino acid at position 1 is removed and the amino acids at positions 125, 38, and 80 are substituted with different amino acids;

(m) a method, wherein in native interleukin-2, the amino acid at position 1 is removed and the amino acids at positions 125, 38, and 84 are substituted with different amino acids;

(n) a method, wherein in native interleukin-2, the amino acid at position 1 is removed and the amino acids at positions 125, 19, 38, and 42 are substituted with different amino acids;

(o) a method, wherein in native interleukin-2, the amino acid at position 1 is removed and the amino acids at positions 125, 12, 38, and 42 are substituted with different amino acids;

(p) a method, wherein in native interleukin-2, the amino acid at position 1 is removed and the amino acids at positions 125, 38, 42, and 61 are substituted with different amino acids;

(q) a method, wherein in native interleukin-2, the amino acid at position 1 is removed and the amino acids at positions 125, 38, 42, and 84 are substituted with different amino acids;

(r) a method, wherein in native interleukin-2, the amino acid at position 1 is removed and the amino acids at positions 125, 38, 42, and 88 are substituted with different amino acids;

(s) a method, wherein in native interleukin-2, the amino acid at position 1 is removed and the amino acids at positions 125, 38, 42, and 89 are substituted with different amino acids;

(t) a method, wherein in native interleukin-2, the amino acid at position 1 is removed and the amino acids at positions 125, 38, 42, and 91 are substituted with different amino acids;

(u) a method, wherein in native interleukin-2, the amino acid at position 1 is removed and the amino acids at positions 125, 38, 42, and 94 are substituted with different amino acids;

(v) a method, wherein in native interleukin-2, the amino acid at position 1 is removed and the amino acids at positions 125, 38, 42, and 126 are substituted with different amino acids;

(w) a method, wherein in native interleukin-2, the amino acid at position 1 is removed and the amino acids at positions 125, 38, 80, and 84 are substituted with different amino acids;

(x) a method, wherein in native interleukin-2, the amino acid at position 1 is removed and the amino acids at positions 125, 38, 94, and 96 are substituted with different amino acids;

(y) a method, wherein in native interleukin-2, the amino acid at position 1 is removed and the amino acids at positions 125, 38, 81, and 92 are substituted with different amino acids;

(z) a method, wherein in native interleukin-2, the amino acid at position 1 is removed and the amino acids at positions 125, 61, 81, and 92 are substituted with different amino acids;

(aa) a method, wherein in native interleukin-2, the amino acid at position 1 is removed and the amino acids at positions 125, 38, 42, 81, and 92 are substituted with different amino acids;

(ab) a method, wherein in native interleukin-2, the amino acid at position 1 is removed and the amino acids at positions 125, 38, 80, 81, and 92 are substituted with different amino acids;

(ac) a method, wherein in native interleukin-2, the amino acid at position 1 is removed and the amino acids at positions 125, 38, 81, 84, and 92 are substituted with different amino acids;

(ad) a method, wherein in native interleukin-2, the amino acid at position 1 is removed and the amino acids at positions 125, 20, 38, 42, 81, and 92 are substituted with different amino acids;

(ae) a method, wherein in native interleukin-2, the amino acid at position 1 is removed and the amino acids at positions 125, 38, 42, 80, 81, and 92 are substituted with different amino acids;

(af) a method, wherein in native interleukin-2, the amino acid at position 1 is removed and the amino acids at positions 125, 38, 42, 74, 81, and 92 are substituted with different amino acids;

(ag) a method, wherein in native interleukin-2, the amino acid at position 1 is removed and the amino acids at positions 125, 38, 42, 81, 84, and 92 are substituted with different amino acids;

(ah) a method, wherein in native interleukin-2, the amino acid at position 1 is removed and the amino acids at positions 125, 38, 42, 81, 88, and 92 are substituted with different amino acids;

(ai) a method, wherein in native interleukin-2, the amino acid at position 1 is removed and the amino acids at positions 125, 38, 42, 85, 86, and 92 are substituted with different amino acids;

(aj) a method, wherein in native interleukin-2, the amino acid at position 1 is removed and the amino acids at positions 125, 38, 80, 81, 85, and 92 are substituted with different amino acids;

(ak) a method, wherein in native interleukin-2, the amino acid at position 1 is removed and the amino acids at positions 125, 38, 80, 81, 86, and 92 are substituted with different amino acids;

(al) a method, wherein in native interleukin-2, the amino acid at position 1 is removed and the amino acids at positions 125, 80, 81, 85, 86, and 92 are substituted with different amino acids;

(am) a method, wherein in native interleukin-2, the amino acid at position 1 is removed and the amino acids at positions 125, 38, 42, 45, 74, 81, and 92 are substituted with different amino acids;

(an) a method, wherein in native interleukin-2, the amino acid at position 1 is removed and the amino acids at positions 125, 38, 42, 74, 80, 81, and 92 are substituted with different amino acids;

(ao) a method, wherein in native interleukin-2, the amino acid at position 1 is removed and the amino acids at positions 125, 38, 42, 80, 81, 84, and 92 are substituted with different amino acids;

(ap) a method, wherein in native interleukin-2, the amino acid at position 1 is removed and the amino acids at positions 125, 38, 45, 80, 85, 86, and 92 are substituted with different amino acids;

(aq) a method, wherein in native interleukin-2, the amino acid at position 1 is removed and the amino acids at positions 125, 38, 80, 81, 85, 86, and 92 are substituted with different amino acids;

(ar) a method, wherein in native interleukin-2, the amino acid at position 1 is removed and the amino acids at positions 125, 42, 80, 81, 85, 86, and 92 are substituted with different amino acids;
(as) a method, wherein in native interleukin-2, the amino acid at position 1 is removed and the amino acids at positions 125, 61, 80, 81, 85, 86, and 92 are substituted with different amino acids;
(at) a method, wherein in native interleukin-2, the amino acid at position 1 is removed and the amino acids at positions 125, 69, 80, 81, 85, 86, and 92 are substituted with different amino acids;
(au) a method, wherein in native interleukin-2, the amino acid at position 1 is removed and the amino acids at positions 125, 80, 81, 85, 86, 91, and 92 are substituted with different amino acids;
(av) a method, wherein in native interleukin-2, the amino acid at position 1 is removed and the amino acids at positions 125, 18, 22, 80, 81, 85, 86, and 92 are substituted with different amino acids;
(aw) a method, wherein in native interleukin-2, the amino acid at position 1 is removed and the amino acids at positions 125, 38, 42, 80, 81, 85, 86, and 92 are substituted with different amino acids;
(ax) a method, wherein in native interleukin-2, the amino acid at position 1 is removed and the amino acids at positions 125, 38, 42, 45, 74, 80, 81, and 92 are substituted with different amino acids;
(ay) a method, wherein in native interleukin-2, the amino acid at position 1 is removed and the amino acids at positions 125, 38, 68, 80, 81, 85, 86, and 92 are substituted with different amino acids;
(az) a method, wherein in native interleukin-2, the amino acid at position 1 is removed and the amino acids at positions 125, 69, 74, 80, 81, 85, 86, and 92 are substituted with different amino acids;
(ba) a method, wherein in native interleukin-2, the amino acid at position 1 is removed and the amino acids at positions 125, 80, 81, 84, 85, 86, 91, and 92 are substituted with different amino acids;
(bb) a method, wherein in native interleukin-2, the amino acid at position 1 is removed and the amino acids at positions 125, 80, 81, 85, 86, 92, 94, and 96 are substituted with different amino acids;
(bc) a method, wherein in native interleukin-2, the amino acid at position 1 is removed and the amino acids at positions 125, 18, 19, 22, 80, 81, 85, 86, and 92 are substituted with different amino acids;
(bd) a method, wherein in native interleukin-2, the amino acid at position 1 is removed and the amino acids at positions 125, 18, 22, 38, 80, 81, 85, 86, and 92 are substituted with different amino acids;
(be) a method, wherein in native interleukin-2, the amino acid at position 1 is removed and the amino acids at positions 125, 18, 22, 61, 80, 81, 85, 86, and 92 are substituted with different amino acids;
(bf) a method, wherein in native interleukin-2, the amino acid at position 1 is removed and the amino acids at positions 125, 18, 22, 68, 80, 81, 85, 86, and 92 are substituted with different amino acids;
(bg) a method, wherein in native interleukin-2, the amino acid at position 1 is removed and the amino acids at positions 125, 35, 38, 42, 80, 81, 85, 86, and 92 are substituted with different amino acids;
(bh) a method, wherein in native interleukin-2, the amino acid at position 1 is removed and the amino acids at positions 125, 38, 42, 45, 80, 81, 85, 86, and 92 are substituted with different amino acids;
(bi) a method, wherein in native interleukin-2, the amino acid at position 1 is removed and the amino acids at positions 125, 38, 42, 80, 81, 85, 86, 91, and 92 are substituted with different amino acids;
(bj) a method, wherein in native interleukin-2, the amino acid at position 1 is removed and the amino acids at positions 125, 38, 42, 80, 81, 85, 86, 92, and 95 are substituted with different amino acids;
(bk) a method, wherein in native interleukin-2, the amino acid at position 1 is removed and the amino acids at positions 125, 35, 38, 42, 74, 80, 81, 85, 86, and 92 are substituted with different amino acids;
(bl) a method, wherein in native interleukin-2, the amino acid at position 1 is removed and the amino acids at positions 125, 38, 42, 43, 61, 80, 81, 85, 86, and 92 are substituted with different amino acids;
(bm) a method, wherein in native interleukin-2, the amino acid at position 1 is removed and the amino acids at positions 125, 38, 42, 80, 81, 85, 86, 91, 92, and 95 are substituted with different amino acids;
(bn) a method, wherein in native interleukin-2, the amino acid at position 1 is removed and the amino acids at positions 125, 35, 38, 42, 74, 80, 81, 82, 85, 86, and 92 are substituted with different amino acids;
(bo) a method, wherein in native interleukin-2, the amino acid at position 1 is removed and the amino acids at positions 125, 80, 81, 86, and 92 are substituted with different amino acids; or
(bp) a method, wherein in native interleukin-2, the amino acid at position 1 is removed and the amino acids at positions 125, 80, 81, 85, and 86 are substituted with different amino acids, but the method is not limited thereto.

The interleukin-2 analog and modification are the same as above.

Still another aspect to implement the present invention provides an interleukin-2 analog which includes any one sequence selected from the group consisting of amino acid sequences of SEQ ID NOS: 3 to 106.

The definitions of the interleukin-2 analog, modification, and analog represented by a SEQ ID NO are the same as above.

Specifically, the interleukin-2 analog may include, essentially consist of, or consist of any one nucleotide sequence selected from the group consisting of SEQ ID NOS: 3 to 106, but the interleukin-2 analog is not limited thereto.

Still another aspect to implement the present invention provides an interleukin-2 analog which includes an amino acid sequence represented by General Formula 1 below:

[General Formula 1]
                (General Formula 1, SEQ ID NO: 212)
X1-P-T-S-S-S-T-K-K-T-Q-L-Q-L-E-H-L-X18-X19-D-L-

X22-M-I-L-N-G-I-N-N-Y-K-N-P-K-L-T-X38-M-L-T-X42-

X43-F-X45-M-P-K-K-A-T-E-L-K-H-L-Q-C-L-E-X61-E-L-K-

P-L-E-X68-V-L-N-L-A-X74-S-K-N-F-H-X80-X81-P-R-X84-

X85-X86-S-N-I-N-X91-X92-V-X94-E-X96-K-G-S-E-T-T-F-

M-C-E-Y-A-D-E-T-A-T-I-V-E-F-L-N-R-W-I-T-F-S-Q-S-I-

I-S-T-L-T wherein in General Formula 1 above,
X1 is a deletion;
X18 is leucine (L) or arginine (R);
X19 is leucine (L) or tyrosine (Y);
X22 is glutamic acid (E) or glutamine (Q);
X38 is alanine (A), aspartic acid (D), or arginine (R);
X42 is alanine (A), phenylalanine (F), lysine (K), or tryptophan (W);
X43 is glutamic acid (E), lysine (K), or glutamine (Q);
X45 is alanine (A) or tyrosine (Y);
X61 is aspartic acid (D), glutamic acid (E), glutamine (Q), or arginine (R);
X68 is aspartic acid (D) or glutamic acid (E);
X74 is histidine (H) or glutamine (Q);
X80 is phenylalanine (F), leucine (L), valine (V), or tyrosine (Y);
X81 is aspartic acid (D), glutamic acid (E), or arginine (R);
X84 is aspartic acid (D) or glutamic acid (E);
X85 is alanine (A), glutamic acid (E), glycine (G), leucine (L), valine (V), tryptophan (W), or tyrosine (Y);
X86 is alanine (A), glycine (G), isoleucine (I), or valine (V);
X91 is threonine (T) or valine (V);
X92 is phenylalanine (F), isoleucine (I), or tyrosine (Y);
X94 is phenylalanine (F) or leucine (L); and
X96 is phenylalanine (F) or leucine (L).

Additionally, in General Formula 1 above, one or more amino acids may be added to threonine (T), which corresponds to X133, but the sequence is not limited thereto.

Specifically, the interleukin-2 analog may include, essentially consist of, or consist of any one sequence selected from the group consisting of amino acid sequences of SEQ ID NOS: 10, 13, 14, 15, 16, 17, 20, 21, 22, 32, 35, 36, 42, 53, 54, 56, 58, 59, 60, 62, 71, 72, 74, 75, 76, 77, 78, 85, 87, 89, 91, 92, 93, 94, 95, 98, 99, 100, 101, 103, 104, 105, and 106, but the interleukin-2 analog is not limited thereto.

Such an interleukin-2 analog may have increased binding affinity for beta receptors compared to aldesleukin or native interleukin-2, but the binding affinity of the interleukin-2 analog is not limited thereto.

In another embodiment, the interleukin-2 analog of the present invention may be: in General Formula 1 above,
X43 is lysine (K);
X45 is tyrosine (Y);
X61 is aspartic acid (D), glutamic acid (E), or glutamine (Q);
X68 is glutamic acid (E);
X74 is glutamine (Q);
X80 is phenylalanine (F) or leucine (L);
X85 is leucine (L), valine (V), or tyrosine (Y);
X86 is isoleucine (I) or valine (V); and
X92 is phenylalanine (F) or isoleucine (I), but the interleukin-2 analog is not limited thereto.

Specifically, the interleukin-2 analog is characterized in that it includes any one sequence selected from the group consisting of amino acid sequences of SEQ ID NOS: 10, 13, 14, 16, 17, 20, 21, 22, 32, 35, 36, 42, 53, 54, 87, 89, 91, 92, 93, 94, 98, 99, 100, 101, 103, 104, and 105.

In the interleukin-2 analog of the present invention, one or more amino acids may be further added to a C-terminus thereof, but the interleukin-2 analog is not limited thereto.

Still another aspect to implement the present invention provides an interleukin-2 analog which includes an amino acid sequence expressed by General Formula 2 below:

[General Formula 2]
(General Formula 2, SEQ ID NO: 213)
X1-P-T-S-S-S-T-K-K-T-Q-L-Q-L-E-H-L-X18-L-D-L-X22-
M-I-L-N-G-I-N-N-Y-K-N-P-K-L-T-X38-M-L-T-X42-K-F-Y-
M-P-K-K-A-T-E-L-K-H-L-Q-C-L-E-X61-E-L-K-P-L-E-X68-
V-L-N-L-A-Q-S-K-N-F-H-F-X81-P-R-D-X85-X86-S-N-I-N-
V-F-V-L-E-L-K-G-S-E-T-T-F-M-C-E-Y-A-D-E-T-A-T-I-V-
E-F-L-N-R-W-I-T-F-S-Q-S-I-I-S-T-L-T wherein in General Formula 2 above,
X1 is a deletion,
X18 is leucine (L) or arginine (R);
X22 is glutamic acid (E) or glutamine (Q);
X38 is alanine (A) or arginine (R);
X42 is phenylalanine (F) or lysine (K);
X61 is aspartic acid (D) or glutamic acid (E);
X68 is aspartic acid (D) or glutamic acid (E);
X81 is aspartic acid (D) or glutamic acid (E);
X85 is leucine (L) or valine (V); and
X86 is isoleucine (I) or valine (V).

Specifically, the interleukin-2 analog may include any one sequence selected from the group consisting of amino acid sequences of SEQ ID NO: 22, 42, 53, 87, 105, and 106, but the sequence of the interleukin-2 analog is not limited thereto.

Additionally, in General Formula 2 above, one or more amino acids may be added to threonine (T), which corresponds to X133, or alternatively, in the interleukin-2 analog, one or more amino acids may be further added to a C-terminus thereof, but the present invention is not limited thereto.

Meanwhile, unless otherwise required by context in the present specification, expressions such as "include", "including", "containing", etc. mean that they include a specified integer or group of integers, but it should be understood that these expressions do not exclude other integers or a set of integers.

Hereinafter, the present invention will be described in more detail through examples. These Examples are only for describing the present invention in more detail, and the scope of the present invention is not limited by these Examples.

Example 1: Preparation of Expression Vectors for Native Interleukin-2 and Interleukin-2 Analogs For the preparation of expression vectors for native interleukin-2 encoding 133 amino acids, an interleukin-2 that was synthesized based on the reported interleukin-2 sequence (NM_000586.3; SEQ ID NO: 1) was cloned into the pET-22b vector (Novagen). Additionally, a novel interleukin-2 analog was prepared in which an amino acid(s) of interleukin-2 were modified using the interleukin-2 as a template. The PCR conditions for the amplification of the interleukin-2 analog were 16 cycles of a process consisting of 95° C. for 30 seconds, 55° C. for 60 seconds, and 65° C. for 6.5 minutes. In order to confirm whether the amino acid(s) at the desired position had been correctly substituted, sequence analysis was performed on the mutagenesis product obtained under the conditions above. As a result, it was confirmed that the modifications shown in Table 1 below were found based on the native type at the desired mutation positions for each interleukin-2 analog. The thus-obtained expression vectors were named pET22b-interleukin-2 analogs 1 to 105.

Table 1 below shows the altered sequences of amino acids and analog names for each. In order to prepare these interleukin-2 analogs, forward (F) and reverse (R) primers were synthesized, and then PCR was performed to amplify each analog gene.

In Table 1 below, analog 1 represents aldesleukin and primer nos 1 to 203 correspond to SEQ ID NOS: 214 to 417, respectively.

TABLE 1

Types of interleukin-2 analog, positions for modification, and altered sequences thereof

| Analog | Positions for Modification and Altered Sequences Thereof | Primer No. |
|---|---|---|
| 1 | desA1, C125S | 197, 198, 201, 202 |
| 2 | desA1, C125S, S87C | 197, 198, 201, 202, 149, 150 |
| 3 | desA1, C125S, K32C | 197, 198, 201, 202, 19, 20 |
| 4 | desA1, C125S, K35C | 197, 198, 201, 202, 21, 22 |
| 5 | desA1, C125S, K43C | 197, 198, 201, 202, 47, 48 |
| 6 | desA1, C125S, K48C | 197, 198, 201, 202, 53, 54 |
| 7 | desA1, C125S, K49C | 197, 198, 201, 202, 55, 56 |
| 8 | desA1, C125S, K76C | 197, 198, 201, 202, 73, 74 |
| 9 | desA1, C125S, R38A | 197, 198, 201, 202, 25, 26 |
| 10 | desA1, C125S, F42K | 197, 198, 201, 202, 35, 36 |
| 11 | desA1, C125S, F42A | 197, 198, 201, 202, 33, 34 |
| 12 | desA1, C125S, R38A, F42K | 197, 198, 201, 202, 25, 26, 35, 36 |
| 13 | desA1, C125S, R38A, F42A | 197, 198, 201, 202, 25, 26, 33, 34 |
| 14 | desA1, C125S, L19Y, R38A, F42K | 197, 198, 201, 202, 13, 14, 25, 26, 35, 36 |
| 15 | desA1, C125S, R38A, F42K, D84E | 197, 198, 201, 202, 25, 26, 35, 36, 109, 110 |
| 16 | desA1, C125S, R38A, F42K, N88Q | 197, 198, 201, 202, 25, 26, 35, 36, 153, 154 |
| 17 | desA1, C125S, R38A, F42K, V91T | 197, 198, 201, 202, 25, 26, 35, 36, 165, 166 |
| 18 | desA1, C125S, R38A, F42K, E61Q | 197, 198, 201, 202, 25, 26, 35, 36, 59, 60 |
| 19 | desA1, C125S, R38A, F42K, R81D, I92F | 197, 198, 201, 202, 25, 26, 35, 36, 97, 98, 167, 168 |
| 20 | desA1, C125S, R38A, F42K, L85V, I86V, I92F | 197, 198, 201, 202, 25, 26, 35, 36, 139, 140, 167, 168 |
| 21 | desA1, C125S, R38A, F42K, L80F, R81D, L85V, I86V, I92F | 197, 198, 201, 202, 25, 26, 35, 36, 79, 80, 167, 168 |
| 22 | desA1, C125S, L12V, R38A, F42K | 197, 198, 201, 202, 3, 4, 25, 26, 35, 36 |
| 23 | desA1, C125S, L12F, R38A, F42K | 197, 198, 201, 202, 1, 2, 25, 26, 35, 36 |
| 24 | desA1, C125S, L19V, R38A, F42K | 197, 198, 201, 202, 11, 12, 25, 26, 35, 36 |
| 25 | desA1, C125S, L19F, R38A, F42K | 197, 198, 201, 202, 9, 10, 25, 26, 35, 36 |
| 26 | desA1, C125S, R38A, F42K, I89F | 197, 198, 201, 202, 25, 26, 35, 36, 157, 158 |
| 27 | desA1, C125S, R38A, F42K, V91F | 197, 198, 201, 202, 25, 26, 35, 36, 163, 164 |
| 28 | desA1, C125S, R38A, F42K, L94V | 197, 198, 201, 202, 25, 26, 35, 36 |
| 29 | desA1, C125S, R38A, F42K, Q126T | 197, 198, 201, 202, 25, 26, 35, 36, 199, 200 |
| 30 | desA1, C125S, R38A, R81D, I92F | 197, 198, 201, 202, 27, 28, 97, 98, 169, 170 |
| 31 | desA1, C125S, R38A, D84E | 197, 198, 201, 202, 27, 28, 109, 110 |

TABLE 1-continued

Types of interleukin-2 analog, positions for modification, and altered sequences thereof

| Analog | Positions for Modification and Altered Sequences Thereof | Primer No. |
|---|---|---|
| 32 | desA1, C125S, R38A, R81D, D84E, I92F | 197, 198, 201, 202, 27, 28, 95, 96, 169, 170 |
| 33 | desA1, C125S, R38A, L80F | 197, 198, 201, 202, 27, 28, 77, 78 |
| 34 | desA1, C125S, R38A, L80F, D84E | 197, 198, 201, 202, 27, 28, 77, 78, 109, 110 |
| 35 | desA1, C125S, R38A, L94F, L96F | 197, 198, 201, 202, 27, 28, 189, 190 |
| 36 | desA1, C125S, R38A, L94F, L96V | 197, 198, 201, 202, 27, 28, 193, 194 |
| 37 | desA1, C125S, R38A, L94F, L96I | 197, 198, 201, 202, 27, 28, 191, 192 |
| 38 | desA1, C125S, R38A, F42K, R81D, I92F, L94F, L96F | 197, 198, 201, 202, 25, 26, 35, 36, 97, 98, 175, 176 |
| 39 | desA1, C125S, R38A, F42K, R81D, I92F, L94F, L96V | 197, 198, 201, 202, 25, 26, 35, 36, 97, 98, 179, 180 |
| 40 | desA1, C125S, R38A, F42K, R81D, I92F, L94F, L96I | 197, 198, 201, 202, 25, 26, 35, 36, 97, 98, 177, 178 |
| 41 | desA1, C125S, L80F, R81D, L85V, I86V, I92F | 197, 198, 201, 202, 25, 26, 29, 30, 35, 36, 41, 42, 79, 80, 167, 168 |
| 42 | desA1, C125S, R38A, F42K, R81E, I92F | 197, 198, 201, 202, 25, 26, 35, 36, 103, 104, 169, TABLE 1-continued Types of interleukin-2 analog, positions for
modification, and altered sequences thereof

| Analog | Positions for Modification and Altered Sequences Thereof | Primer No. |
|---|---|---|
| 59 | desA1, C125S, R38A, F42K, L80F, R81D, L85A, I86A, I92Y | 197, 198, 201, 202, 25, 26, 35, 36, 79, 80, 115, 116, 187, 188 |
| 60 | desA1, C125S, R38A, Y45A, L80Y, L85A, I86A, I92Y | 197, 198, 201, 202, 27, 28, 35, 36, 41, 42, 51, 52, 93, 94, 115, 116, 187, 188 |
| 61 | desA1, C125S, R38A, F42K, L80Y, R81D, L85G, I86V, I92Y | 197, 198, 201, 202, 25, 26, 35, 36, 87, 88, 125, 126, 187, 188 |
| 62 | desA1, C125S, R38A, L80W, R81E, L85G, I86A, I92F | 197, 198, 201, 202, 27, 28, 35, 36, 41, 42, 85, 86, 123, 124, 171, 172 |
| 63 | desA1, C125S, R38A, F42K, L80D, R81E, L85T, I86G, I92F | 197, 198, 201, 202, 25, 26, 35, 36, 75, 76, 133, 134, 167, 168 |
| 64 | desA1, C125S, R38A, F42K, L80Y, R81N, L85V, I86V, I92F | 197, 198, 201, 202, 25, 26, 35, 36, 91, 92, 139, 140, 167, 168 |
| 65 | desA1, C125S, R38A, F42K, L80Y, R81E, L85V, I86V, I92F | 197, 198, 201, 202, 25, 26, 35, 36, 89, 90, 139, 140, 167, 168 |
| 66 | desA1, C125S, R38A, F42K, L80F, R81E, L85F, I86V, I92F | 197, 198, 201, 202, 25, 26, 35, 36, 81, 82, 121, 122, 167, 168 |
| 67 | desA1, C125S, R38A, F42K, L80Y, R81D, L85F, I86V, I92W, E95D | 197, 198, 201, 202, 25, 26, 35, 36, 87, 88, 121, 122, 185, 186, 195, 196 |
| 68 | desA1, C125S, R38A, F42K, L80F, R81E, L85I, I86V, V91E, I92F | 197, 198, 201, 202, 25, 26, 35, 36, 81, 82, 127, 128, 159, 160, 167, 168 |
| 69 | desA1, C125S, R38A, F42K, L80Y, R81E, L85F, I86L, V91E, I92W, E95D | 197, 198, 201, 202, 25, 26, 35, 36, 89, 90, 119, 120, 161, 162, 185, 186, 195, 196 |
| 70 | desA1, C125S, R38A, F42K, L80Y, R81D, L85V, I86V, I92F | 197, 198, 201, 202, 25, 26, 35, 36, 87, 88, 139, 140, 167, 168 |
| 71 | desA1, C125S, R38A, F42K, L80F, R81E, L85V, I86V, I92F | 197, 198, 201, 202, 25, 26, 35, 36, 81, 82, 139, 140, 167, 168 |
| 72 | desA1, C125S, R38A, F42K, L80F, R81D, L85V, I86G, I92F | 197, 198, 201, 202, 25, 26, 35, 36, 79, 80, 135, 136, 167, 168 |
| 73 | desA1, C125S, R38A, F42K, L80F, R81D, L85W, I86V, I92F | 197, 198, 201, 202, 25, 26, 35, 36, 79, 80, 141, 142, 167, 168 |
| 74 | desA1, C125S, R38D, F42K, L80Y, R81D, L85V, I86V, I92F | 197, 198, 201, 202, 31, 32, 35, 36, 87, 88, 139, 140, 167, 168 |
| 75 | desA1, C125S, R38A, F42K, Y45A, L80F, R81E, L85V, I86V, I92F | 197, 198, 201, 202, 25, 26, 35, 36, 51, 52, 81, 82, 139, 140, 167, 168 |
| 76 | desA1, C125S, R38A, F42K, K43Q, E61R, L80F, R81D, L85V, I86G, I92F | 197, 198, 201, 202, 25, 26, 39, 40, 61, 62, 79, 80, 135, 136, 167, 168 |
| 77 | desA1, C125S, R38A, F42K, K43E, E61R, L80F, R81D, L85W, I86V, I92F | 197, 198, 201, 202, 25, 26, 37, 38, 61, 62, 79, 80, 143, 144, 167, 168 |
| 78 | desA1, C125S, K35E, R38A, F42K, L80F, R81E, L85V, I86V, I92F | 197, 198, 201, 202, 23, 24, 25, 26, 35, 36, 81, 82, 139, 140, 167, 168 |
| 79 | desA1, C125S, K35E, R38A, F42K, Q74H, L80F, R81E, L85V, I86V, I92F | 197, 198, 201, 202, 23, 24, 25, 26, 35, 36, 71, 72, 81, 82, 139, 140, 167, 168 |
| 80 | desA1, C125S, K35E, R38A, F42K, Q74H, L80F, R81E, P82G, L85V, I86V, I92F | 197, 198, 201, 202, 23, 24, 25, 26, 35, 36, 71, 72, 81, 82, 105, 106, 139, 140, 167, 168 |
| 81 | desA1, C125S, K35E, R38A, F42K, Q74H, L80F, R81E, P82V, L85V, I86V, I92F | 197, 198, 201, 202, 23, 24, 25, 26, 35, 36, 71, 72, 81, 82, 107, 108, 139, 140, 167, 168 |

TABLE 1-continued

Types of interleukin-2 analog, positions for modification, and altered sequences thereof

| Analog | Positions for Modification and Altered Sequences Thereof | Primer No. |
|---|---|---|
| 82 | desA1, C125S, L18R, Q22E, L80F, R81D, L85E, I86V, I92F | 197, 198, 201, 202, 7, 8, 25, 26, 29, 30, 35, 36, 43, 44, 79, 80, 117, 118, 167, 168 |
| 83 | desA1, C125S, L18R, L19R, Q22E, L80F, R81D, L85E, I86V, I92F | 197, 198, 201, 202, 5, 6, 25, 26, 29, 30, 35, 36, 43, 44, 79, 80, 117, 118, 167, 168 |
| 84 | desA1, C125S, L18R, Q22E, L80V, R81D, L85E, I86V, I92F | 197, 198, 201, 202, 7, 8, 25, 26, 29, 30, 35, 36, 43, 44, 83, 84, 117, 118, 167, 168 |
| 85 | desA1, C125S, L80F, R81E, L85V, I86V, I92F | 197, 198, 201, 202, 25, 26, 29, 30, 35, 36, 43, 44, 81, 82, 139, 140, 167, 168 |
| 86 | desA1, C125S, L18R, Q22E, L80F, R81E, L85V, I86V, I92F | 197, 198, 201, 202, 7, 8, 25, 26, 29, 30, 35, 36, 43, 44, 81, 82, 139, 140, 167, 168 |
| 87 | desA1, C125S, L18R, L19R, Q22E, L80F, R81E, L85V, I86V, I92F | 197, 198, 201, 202, 5, 6, 25, 26, 29, 30, 35, 36, 43, 44, 81, 82, 139, 140, 167, 168 |
| 88 | desA1, C125S, E61D, L80F, R81E, L85V, I86V, I92F | 197, 198, 201, 202, 25, 26, 29, 30, 35, 36, 43, 44, 57, 58, 81, 82, 139, 140, 167, 168 |
| 89 | desA1, C125S, R38A, E68Q, L80F, R81E, L85V, I86V, I92F | 197, 198, 201, 202, 27, 28, 35, 36, 43, 44, 65, 66, 81, 82, 139, 140, 167, 168 |
| 90 | desA1, C125S, F42W, L80F, R81E, L85V, I86V, I92F | 197, 198, 201, 202, 25, 26, 29, 30, 45, 46, 81, 82, 139, 140, 167, 168 |
| 91 | desA1, C125S, E61Q, L80F, R81E, L85V, I86V, I92F | 197, 198, 201, 202, 25, 26, 29, 30, 35, 36, 43, 44, 59, 60, 81, 82, 139, 140, 167, 168 |
| 92 | desA1, C125S, L80F, R81E, L85V, I86V, V91T, I92F | 197, 198, 201, 202, 25, 26, 29, 30, 35, 36, 43, 44, 81, 82, 139, 140, 147, 148, 167, 168 |
| 93 | desA1, C125S, L80F, R81E, D84E, L85V, I86V, V91T, I92F | 197, 198, 201, 202, 25, 26, 29, 30, 35, 36, 43, 44, 81, 82, 101, 102, 139, 140, 167, 168 |
| 94 | desA1, C125S, L80F, R81E, L85V, I86V, I92F, L94F, L96F | 197, 198, 201, 202, 25, 26, 29, 30, 35, 36, 43, 44, 81, 82, 139, 140, 173, 174 |
| 95 | desA1, C125S, V69G, L80F, R81E, L85V, I86V, I92F | 197, 198, 201, 202, 25, 26, 29, 30, 35, 36, 43, 44, 67, 68, 81, 82, 139, 140, 167, 168 |
| 96 | desA1, C125S, V69G, Q74A, L80F, R81E, L85V, I86V, I92F | 197, 198, 201, 202, 25, 26, 29, 30, 35, 36, 43, 44, 69, 70, 81, 82, 139, 140, 167, 168 |
| 97 | desA1, C125S, R38A, L80F, R81D, I92F | 197, 198, 201, 202, 27, 28, 35, 36, 41, 42, 79, 80, 167, 168 |
| 98 | desA1, C125S, R38A, L80F, R81E, L85V, I92F | 197, 198, 201, 202, 27, 28, 35, 36, 41, 42, 81, 82, 137, 138, 167, 168 |
| 99 | desA1, C125S, R38A, L80F, R81E, I86V, I92F | 197, 198, 201, 202, 27, 28, 35, 36, 41, 42, 81, 82, 131, 132, 167, 168 |
| 100 | desA1, C125S, L80F, R81E, L85Y, I86V, I92F | 197, 198, 201, 202, 25, 26, 29, 30, 35, 36, 41, 42, 81, 82, 145, 146, 167, 168 |
| 101 | desA1, C125S, L80F, R81E, I86A, I92F | 197, 198, 201, 202, 25, 26, 29, 30, 35, 36, 41, |

TABLE 1-continued

Types of interleukin-2 analog, positions for modification, and altered sequences thereof

| Analog | Positions for Modification and Altered Sequences Thereof | Primer No. |
|---|---|---|
| 102 | desA1, C125S, L80F, R81E, L85V, I86V | 42, 81, 82, 129, 130, 167, 168<br>197, 198, 201, 202, 25, 26, 29, 30, 35, 36, 41, 42, 81, 82, 139, 140, 181, 182 |
| 103 | desA1, C125S, L18R, Q22E, R38A, L80F, R81E, L85V, I86V, I92F | 197, 198, 201, 202, 7, 8, 27, 28, 35, 36, 41, 42, 81, 82, 139, 140, 167, 168 |
| 104 | desA1, C125S, L18R, Q22E, E61D, L80F, R81E, L85V, I86V, I92F | 197, 198, 201, 202, 7, 8, 25, 26, 29, 30, 35, 36, 41, 42, 57, 58, 81, 82, 139, 140, 167, 168 |
| 105 | desA1, C125S, L18R, Q22E, E68D, L80F, R81E, L85V, I86V, I92F | 197, 198, 201, 202, 7, 8, 25, 26, 29, 30, 35, 36, 41, 42, 63, 64, 81, 82, 139, 140, 167, 168 |

In Table 1 above, desA1 represents a deletion of alanine, which is the first amino acid in interleukin-2.

Table 2 below shows full-length protein sequences of interleukin-2 analogs. The letters shown in bold in Table 2 represent the positions for modification.

TABLE 2

Sequences of interleukin-2 analogs

| Analog | Protein Sequence | SEQ ID NO of Proteins | SEQ ID NO of Nucleotides |
|---|---|---|---|
| 1 | PTSSSTKKT QLQLEHLLLD LQMILNGINN YKNPKLTRML<br>TFKFYMPKKA TELKHLQCLE EELKPLEEVL NLAQSKNFHL<br>RPRDLISNIN VIVLELKGSE TTFMCEYADE TATIVEFLNR<br>WITFSQSIIS TLT | 2 | 107 |
| 2 | PTSSSTKKT QLQLEHLLLD LQMILNGINN YKNPKLTRML<br>TFKFYMPKKA TELKHLQCLE EELKPLEEVL NLAQSKNFHL<br>RPRDLICNIN VIVLELKGSE TTFMCEYADE TATIVEFLNR<br>WITFSQSIIS TLT | 3 | 108 |
| 3 | PTSSSTKKT QLQLEHLLLD LQMILNGINN YCNPKLTRML<br>TFKFYMPKKA TELKHLQCLE EELKPLEEVL NLAQSKNFHL<br>RPRDLISNIN VIVLELKGSE TTFMCEYADE TATIVEFLNR<br>WITFSQSIIS TLT | 4 | 109 |
| 4 | PTSSSTKKT QLQLEHLLLD LQMILNGINN YKNPCLTRML<br>TFKFYMPKKA TELKHLQCLE EELKPLEEVL NLAQSKNFHL<br>RPRDLISNIN VIVLELKGSE TTFMCEYADE TATIVEFLNR<br>WITFSQSIIS TLT | 5 | 110 |
| 5 | PTSSSTKKT QLQLEHLLLD LQMILNGINN YKNPKLTRML<br>TFCFYMPKKA TELKHLQCLE EELKPLEEVL NLAQSKNFHL<br>RPRDLISNIN VIVLELKGSE TTFMCEYADE TATIVEFLNR<br>WITFSQSIIS TLT | 6 | 111 |
| 6 | PTSSSTKKT QLQLEHLLLD LQMILNGINN YKNPKLTRML<br>TFKFYMPCKA TELKHLQCLE EELKPLEEVL NLAQSKNFHL<br>RPRDLISNIN VIVLELKGSE TTFMCEYADE TATIVEFLNR<br>WITFSQSIIS TLT | 7 | 112 |
| 7 | PTSSSTKKT QLQLEHLLLD LQMILNGINN YKNPKLTRML<br>TFKFYMPKCA TELKHLQCLE EELKPLEEVL NLAQSKNFHL<br>RPRDLISNIN VIVLELKGSE TTFMCEYADE TATIVEFLNR<br>WITFSQSIIS TLT | 8 | 113 |

TABLE 2-continued

Sequences of interleukin-2 analogs

| Analog | Protein Sequence | SEQ ID NO of Proteins | SEQ ID NO of Nucleotides |
|---|---|---|---|
| 8 | PTSSSTKKT QLQLEHLLLD LQMILNGINN YKNPKLTRML TFKFYMPKKA TELKHLQCLE EELKPLEEVL NLAQSCNFHL RPRDLISNIN VIVLELKGSE TTFMCEYADE TATIVEFLNR WITFSQSIIS TLT | 9 | 114 |
| 9 | PTSSSTKKT QLQLEHLLLD LQMILNGINN YKNPKLTAML TFKFYMPKKA TELKHLQCLE EELKPLEEVL NLAQSKNFHL RPRDLISNIN VIVLELKGSE TTFMCEYADE TATIVEFLNR WITFSQSIIS TLT | 10 | 115 |
| 10 | PTSSSTKKT QLQLEHLLLD LQMILNGINN YKNPKLTRML TKKFYMPKKA TELKHLQCLE EELKPLEEVL NLAQSKNFHL RPRDLISNIN VIVLELKGSE TTFMCEYADE TATIVEFLNR WITFSQSIIS TLT | 11 | 116 |
| 11 | PTSSSTKKT QLQLEHLLLD LQMILNGINN YKNPKLTRML TAKFYMPKKA TELKHLQCLE EELKPLEEVL NLAQSKNFHL RPRDLISNIN VIVLELKGSE TTFMCEYADE TATIVEFLNR WITFSQSIIS TLT | 12 | 117 |
| 12 | PTSSSTKKT QLQLEHLLLD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 13 | 118 |
| 13 | PTSSSTKKT QLQLEHLLLD LQMILNGINN YKNPKLTAML TAKFYMPKKA TELKHLQCLE EELKPLEEVL NLAQSKNFHL RPRDLISNIN VIVLELKGSE TTFMCEYADE TATIVEFLNR WITFSQSIIS TLT | 14 | 119 |
| 14 | PTSSSTKKT QLQLEHLLYD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 15 | 120 |
| 15 | PTSSSTKKT QLQLEHLLLD LQMILNGINN YKNPKLTAML TKKFYMPKKA TELKHLQCLE EELKPLEEVL NLAQSKNFHL RPRELISNIN VIVLELKGSE TTFMCEYADE TATIVEFLNR WITFSQSIIS TLT | 16 | 121 |
| 16 | PTSSSTKKT QLQLEHLLLD LQMILNGINN YKNPKLTAML TKKFYMPKKA TELKHLQCLE EELKPLEEVL NLAQSKNFHL RPRDLISQIN VIVLELKGSE TTFMCEYADE TATIVEFLNR WITFSQSIIS TLT | 17 | 122 |
| 17 | PTSSSTKKT QLQLEHLLLD LQMILNGINN YKNPKLTAML TKKFYMPKKA TELKHLQCLE EELKPLEEVL NLAQSKNFHL RPRDLISNIN TIVLELKGSE TTFMCEYADE TATIVEFLNR WITFSQSIIS TLT | 18 | 123 |
| 18 | PTSSSTKKT QLQLEHLLLD LQMILNGINN YKNPKLTAML TKKFYMPKKA TELKHLQCLE QELKPLEEVL NLAQSKNFHL RPRDLISNIN VIVLELKGSE TTFMCEYADE TATIVEFLNR WITFSQSIIS TLT | 19 | 124 |
| 19 | PTSSSTKKT QLQLEHLLLD LQMILNGINN YKNPKLTAML TKKFYMPKKA TELKHLQCLE EELKPLEEVL NLAQSKNFHL DPRDLISNIN VFVLELKGSE TTFMCEYADE TATIVEFLNR WITFSQSIIS TLT | 20 | 125 |
| 20 | PTSSSTKKT QLQLEHLLLD LQMILNGINN YKNPKLTAML TKKFYMPKKA TELKHLQCLE EELKPLEEVL NLAQSKNFHL RPRDVVSNIN VFVLELKGSE TTFMCEYADE TATIVEFLNR WITFSQSIIS TLT | 21 | 126 |
| 21 | PTSSSTKKT QLQLEHLLLD LQMILNGINN YKNPKLTAML TKKFYMPKKA TELKHLQCLE EELKPLEEVL NLAQSKNFHF DPRDVVSNIN VFVLELKGSE TTFMCEYADE TATIVEFLNR WITFSQSIIS TLT | 22 | 127 |

TABLE 2-continued

Sequences of interleukin-2 analogs

| Analog | Protein Sequence | SEQ ID NO of Proteins | SEQ ID NO of Nucleotides |
|---|---|---|---|
| 22 | PTSSSTKKT QVQLEHLLLD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 23 | 128 |
| 23 | PTSSSTKKT QFQLEHLLLD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 24 | 129 |
| 24 | PTSSSTKKT QLQLEHLLVD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 25 | 130 |
| 25 | PTSSSTKKT QLQLEHLLFD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 26 | 131 |
| 26 | PTSSSTKKT QLQLEHLLLD LQMILNGINN YKNPKLTAML TKKFYMPKKA TELKHLQCLE EELKPLEEVL NLAQSKNFHL RPRDLISNFN VIVLELKGSE TTFMCEYADE TATIVEFLNR WITFSQSIIS TLT | 27 | 132 |
| 27 | PTSSSTKKT QLQLEHLLLD LQMILNGINN YKNPKLTAML TKKFYMPKKA TELKHLQCLE EELKPLEEVL NLAQSKNFHL RPRDLISNIN FIVLELKGSE TTFMCEYADE TATIVEFLNR WITFSQSIIS TLT | 28 | 133 |
| 28 | PTSSSTKKT QLQLEHLLLD LQMILNGINN YKNPKLTAML TKKFYMPKKA TELKHLQCLE EELKPLEEVL NLAQSKNFHL RPRDLISNIN VIVVELKGSE TTFMCEYADE TATIVEFLNR WITFSQSIIS TLT | 29 | 134 |
| 29 | PTSSSTKKT QLQLEHLLLD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 30 | 135 |
| 30 | PTSSSTKKT QLQLEHLLLD LQMILNGINN YKNPKLTAML TFKFYMPKKA TELKHLQCLE EELKPLEEVL NLAQSKNFHL DPRDLISNIN VFVLELKGSE TTFMCEYADE TATIVEFLNR WITFSQSIIS TLT | 31 | 136 |
| 31 | PTSSSTKKT QLQLEHLLLD LQMILNGINN YKNPKLTAML TFKFYMPKKA TELKHLQCLE EELKPLEEVL NLAQSKNFHL RPRELISNIN VIVLELKGSE TTFMCEYADE TATIVEFLNR WITFSQSIIS TLT | 32 | 137 |
| 32 | PTSSSTKKT QLQLEHLLLD LQMILNGINN YKNPKLTAML TFKFYMPKKA TELKHLQCLE EELKPLEEVL NLAQSKNFHL DPRELISNIN VFVLELKGSE TTFMCEYADE TATIVEFLNR WITFSQSIIS TLT | 33 | 138 |
| 33 | PTSSSTKKT QLQLEHLLLD LQMILNGINN YKNPKLTAML TFKFYMPKKA TELKHLQCLE EELKPLEEVL NLAQSKNFHF RPRDLISNIN VIVLELKGSE TTFMCEYADE TATIVEFLNR WITFSQSIIS TLT | 34 | 139 |
| 34 | PTSSSTKKT QLQLEHLLLD LQMILNGINN YKNPKLTAML TFKFYMPKKA TELKHLQCLE EELKPLEEVL NLAQSKNFHF RPRELISNIN VIVLELKGSE TTFMCEYADE TATIVEFLNR WITFSQSIIS TLT | 35 | 140 |
| 35 | PTSSSTKKT QLQLEHLLLD LQMILNGINN YKNPKLTAML TFKFYMPKKA TELKHLQCLE EELKPLEEVL NLAQSKNFHL RPRDLISNIN VIVFEFKGSE TTFMCEYADE TATIVEFLNR WITFSQSIIS TLT | 36 | 141 |
| 36 | PTSSSTKKT QLQLEHLLLD LQMILNGINN YKNPKLTAML TFKFYMPKKA TELKHLQCLE EELKPLEEVL NLAQSKNFHL | 37 | 142 |

TABLE 2-continued

Sequences of interleukin-2 analogs

| Analog | Protein Sequence | SEQ ID NO of Proteins | SEQ ID NO of Nucleotides |
|---|---|---|---|
| | RPRDLISNIN VIVFEVKGSE TTFMCEYADE TATIVEFLNR WITFSQSIIS TLT | | |
| 37 | PTSSSTKKT QLQLEHLLLD LQMILNGINN YKNPKLTAML TFKFYMPKKA TELKHLQCLE EELKPLEEVL NLAQSKNFHL RPRDLISNIN VIVFEIKGSE TTFMCEYADE TATIVEFLNR WITFSQSIIS TLT | 38 | 143 |
| 38 | PTSSSTKKT QLQLEHLLLD LQMILNGINN YKNPKLTAML TKKFYMPKKA TELKHLQCLE EELKPLEEVL NLAQSKNFHL DPRDLISNIN VFVFEFKGSE TTFMCEYADE TATIVEFLNR WITFSQSIIS TLT | 39 | 144 |
| 39 | PTSSSTKKT QLQLEHLLLD LQMILNGINN YKNPKLTAML TKKFYMPKKA TELKHLQCLE EELKPLEEVL NLAQSKNFHL DPRDLISNIN VFVFEVKGSE TTFMCEYADE TATIVEFLNR WITFSQSIIS TLT | 40 | 145 |
| 40 | PTSSSTKKT QLQLEHLLLD LQMILNGINN YKNPKLTAML TKKFYMPKKA TELKHLQCLE EELKPLEEVL NLAQSKNFHL DPRDLISNIN VFVFEIKGSE TTFMCEYADE TATIVEFLNR WITFSQSIIS TLT | 41 | 146 |
| 41 | PTSSSTKKT QLQLEHLLLD LQMILNGINN YKNPKLTRML TFKFYMPKKA TELKHLQCLE EELKPLEEVL NLAQSKNFHF DPRDVVSNIN VFVLELKGSE TTFMCEYADE TATIVEFLNR WITFSQSIIS TLT | 42 | 147 |
| 42 | PTSSSTKKT QLQLEHLLLD LQMILNGINN YKNPKLTAML TKKFYMPKKA TELKHLQCLE EELKPLEEVL NLAQSKNFHL EPRDLISNIN VFVLELKGSE TTFMCEYADE TATIVEFLNR WITFSQSIIS TLT | 43 | 148 |
| 43 | PTSSSTKKT QLQLEHLLLD LQMILNGINN YKNPKLTAML TKKFYMPKKA TELKHLQCLE EELKPLEEVL NLAQSKNFHL DPRDLISNIN VLVLELKGSE TTFMCEYADE TATIVEFLNR WITFSQSIIS TLT | 44 | 149 |
| 44 | PTSSSTKKT QLQLEHLLLD LQMILNGINN YKNPKLTAML TKKFYMPKKA TELKHLQCLE EELKPLEEVL NLAQSKNFHL DPRVLISNIN VFVLELKGSE TTFMCEYADE TATIVEFLNR WITFSQSIIS TLT | 45 | 150 |
| 45 | PTSSSTKKT QLQLEHLLLD LQMILNGINN YKNPKLTAML TKKFYMPKKA TELKHLQCLE EELKPLEEVL NLAQSKNFHL DPRFLISNIN VFVLELKGSE TTFMCEYADE TATIVEFLNR WITFSQSIIS TLT | 46 | 151 |
| 46 | PTSSSTKKT QLQLEHLLLV LQMILNGINN YKNPKLTAML TKKFYMPKKA TELKHLQCLE EELKPLEEVL NLAQSKNFHL DPRDLISNIN VFVLELKGSE TTFMCEYADE TATIVEFLNR WITFSQSIIS TLT | 47 | 152 |
| 47 | PTSSSTKKT QLQLEHLLLF LQMILNGINN YKNPKLTAML TKKFYMPKKA TELKHLQCLE EELKPLEEVL NLAQSKNFHL DPRDLISNIN VFVLELKGSE TTFMCEYADE TATIVEFLNR WITFSQSIIS TLT | 48 | 153 |
| 48 | PTSSSTKKT QLQLEHLLLD LQMILNGINN YKNPKLTAML TKKFYMPKKA TELKHLQCLE EELKPLEEVL NLAQSKNFHL DPRDLISVIN VFVLELKGSE TTFMCEYADE TATIVEFLNR WITFSQSIIS TLT | 49 | 154 |
| 49 | PTSSSTKKT QLQLEHLLLD LQMILNGINN YKNPKLTAML TKKFYMPKKA TELKHLQCLE EELKPLEEVL NLAQSKNFHL DPRDLISFIN VFVLELKGSE TTFMCEYADE TATIVEFLNR WITFSQSIIS TLT | 50 | 155 |
| 50 | PTSSSTKKT QLQLEHLLLD LQMILNGINN YKNPKLTRML TKKFYMPKKA TELKHLQCLE EELKPLEEVL NLAQSKNFHF DPRDVVSNIN VFVLELKGSE TTFMCEYADE TATIVEFLNR WITFSQSIIS TLT | 51 | 156 |

TABLE 2-continued

Sequences of interleukin-2 analogs

| Analog | Protein Sequence | SEQ ID NO of Proteins | SEQ ID NO of Nucleotides |
|---|---|---|---|
| 51 | PTSSSTKKT QLQLEHLLLD LQMILNGINN YKNPKLTRML TFKFYMPKKA TELKHLQCLE QELKPLEEVL NLAQSKNFHL DPRDLISNIN VFVLELKGSE TTFMCEYADE TATIVEFLNR WITFSQSIIS TLT | 52 | 157 |
| 52 | PTSSSTKKT QLQLEHLLLD LQMILNGINN YKNPKLTAML TKKFYMPKKA TELKHLQCLE EELKPLEEVL NLAQSKNFHF DPRDLISNIN VFVLELKGSE TTFMCEYADE TATIVEFLNR WITFSQSIIS TLT | 53 | 158 |
| 53 | PTSSSTKKT QLQLEHLLLD LQMILNGINN YKNPKLTAML TKKFYMPKKA TELKHLQCLE EELKPLEEVL NLAQSKNFHF DPRELISNIN VFVLELKGSE TTFMCEYADE TATIVEFLNR WITFSQSIIS TLT | 54 | 159 |
| 54 | PTSSSTKKT QLQLEHLLLD LQMILNGINN YKNPKLTAML TKKFYMPKKA TELKHLQCLE EELKPLEEVL NLAHSKNFHL DPRDLISNIN VFVLELKGSE TTFMCEYADE TATIVEFLNR WITFSQSIIS TLT | 55 | 160 |
| 55 | PTSSSTKKT QLQLEHLLLD LQMILNGINN YKNPKLTAML TKKFYMPKKA TELKHLOCLE EELKPLEEVL NLAHSKNFHF DPRDLISNIN VFVLELKGSE TTFMCEYADE TATIVEFLNR WITFSQSIIS TLT | 56 | 161 |
| 56 | PTSSSTKKT QLQLEHLLLD LOMILNGINN YKNPKLTAML TKKFAMPKKA TELKHLQCLE EELKPLEEVL NLAHSKNFHL DPRDLISNIN VFVLELKGSE TTFMCEYADE TATIVEFLNR WITFSQSIIS TLT | 57 | 162 |
| 57 | PTSSSTKKT QLQLEHLLLD LQMILNGINN YKNPKLTAML TKKFAMPKKA TELKHLOCLE EELKPLEEVL NLAHSKNFHF DPRDLISNIN VFVLELKGSE TTFMCEYADE TATIVEFLNR WITFSQSIIS TLT | 58 | 163 |
| 58 | PTSSSTKKT QLQLEHLLLD LQMILNGINN YKNPKLTAML TKKFYMPKKA TELKHLQCLE EELKPLEEVL NLAQSKNFHF DPRDAASNIN VFVLELKGSE TTFMCEYADE TATIVEFLNR WITFSQSIIS TLT | 59 | 164 |
| 59 | PTSSSTKKT QLQLEHLLLD LQMILNGINN YKNPKLTAML TKKFYMPKKA TELKHLQCLE EELKPLEEVL NLAQSKNFHF DPRDAASNIN VYVLELKGSE TTFMCEYADE TATIVEFLNR WITFSQSIIS TLT | 60 | 165 |
| 60 | PTSSSTKKT QLQLEHLLLD LQMILNGINN YKNPKLTAML TKKFAMPKKA TELKHLQCLE EELKPLEEVL NLAQSKNFHY RPRDAASNIN VYVLELKGSE TTFMCEYADE TATIVEFLNR WITFSQSIIS TLT | 61 | 166 |
| 61 | PTSSSTKKT QLQLEHLLLD LQMILNGINN YKNPKLTAML TKKFYMPKKA TELKHLQCLE EELKPLEEVL NLAQSKNFHY DPRDGVSNIN VYVLELKGSE TTFMCEYADE TATIVEFLNR WITFSQSIIS TLT | 62 | 167 |
| 62 | PTSSSTKKT QLQLEHLLLD LQMILNGINN YKNPKLTAML TKKFYMPKKA TELKHLQCLE EELKPLEEVL NLAQSKNFHW EPRDGASNIN VFVLELKGSE TTFMCEYADE TATIVEFLNR WITFSQSIIS TLT | 63 | 168 |
| 63 | PTSSSTKKT QLQLEHLLLD LQMILNGINN YKNPKLTAML TKKFYMPKKA TELKHLQCLE EELKPLEEVL NLAQSKNFHD EPRDTGSNIN VFVLELKGSE TTFMCEYADE TATIVEFLNR WITFSQSIIS TLT | 64 | 169 |
| 64 | PTSSSTKKT QLQLEHLLLD LQMILNGINN YKNPKLTAML TKKFYMPKKA TELKHLQCLE EELKPLEEVL NLAQSKNFHY NPRDVVSNIN VYVLELKGSE TTFMCEYADE TATIVEFLNR WITFSQSIIS TLT | 65 | 170 |

TABLE 2-continued

Sequences of interleukin-2 analogs

| Analog | Protein Sequence | SEQ ID NO of Proteins | SEQ ID NO of Nucleotides |
|---|---|---|---|
| 65 | PTSSSTKKT QLQLEHLLLD LQMILNGINN YKNPKLTAML TKKFYMPKKA TELKHLQCLE EELKPLEEVL NLAQSKNFHY EPRDVVSNIN VFVLELKGSE TTFMCEYADE TATIVEFLNR WITFSQSIIS TLT | 66 | 171 |
| 66 | PTSSSTKKT QLQLEHLLLD LQMILNGINN YKNPKLTAML TKKFYMPKKA TELKHLQCLE EELKPLEEVL NLAQSKNFHF EPRDFVSNIN VFVLELKGSE TTFMCEYADE TATIVEFLNR WITFSQSIIS TLT | 67 | 172 |
| 67 | PTSSSTKKT QLQLEHLLLD LQMILNGINN YKNPKLTAML TKKFYMPKKA TELKHLQCLE EELKPLEEVL NLAQSKNFHY DPRDFVSNIN VWVLDLKGSE TTFMCEYADE TATIVEFLNR WITFSQSIIS TLT | 68 | 173 |
| 68 | PTSSSTKKT QLQLEHLLLD LQMILNGINN YKNPKLTAML TKKFYMPKKA TELKHLQCLE EELKPLEEVL NLAQSKNFHF EPRDIVSNIN EFVLELKGSE TTFMCEYADE TATIVEFLNR WITFSQSIIS TLT | 69 | 174 |
| 69 | PTSSSTKKT QLQLEHLLLD LQMILNGINN YKNPKLTAML TKKFYMPKKA TELKHLQCLE EELKPLEEVL NLAQSKNFHY EPRDFLSNIN EWVLDLKGSE TTFMCEYADE TATIVEFLNR WITFSQSIIS TLT | 70 | 175 |
| 70 | PTSSSTKKT QLQLEHLLLD LQMILNGINN YKNPKLTAML TKKFYMPKKA TELKHLQCLE EELKPLEEVL NLAQSKNFHY DPRDVVSNIN VFVLELKGSE TTFMCEYADE TATIVEFLNR WITFSQSIIS TLT | 71 | 176 |
| 71 | PTSSSTKKT QLQLEHLLLD LQMILNGINN YKNPKLTAML TKKFYMPKKA TELKHLQCLE EELKPLEEVL NLAQSKNFHF EPRDVVSNIN VFVLELKGSE TTFMCEYADE TATIVEFLNR WITFSQSIIS TLT | 72 | 177 |
| 72 | PTSSSTKKT QLQLEHLLLD LQMILNGINN YKNPKLTAML TKKFYMPKKA TELKHLQCLE EELKPLEEVL NLAQSKNFHF DPRDVGSNIN VFVLELKGSE TTFMCEYADE TATIVEFLNR WITFSQSIIS TLT | 73 | 178 |
| 73 | PTSSSTKKT QLQLEHLLLD LQMILNGINN YKNPKLTAML TKKFYMPKKA TELKHLQCLE EELKPLEEVL NLAQSKNFHF DPRDWVSNIN VFVLELKGSE TTFMCEYADE TATIVEFLNR WITFSQSIIS TLT | 74 | 179 |
| 74 | PTSSSTKKT QLQLEHLLLD LQMILNGINN YKNPKLTDML TKKFYMPKKA TELKHLQCLE EELKPLEEVL NLAQSKNFHY DPRDVVSNIN VFVLELKGSE TTFMCEYADE TATIVEFLNR WITFSQSIIS TLT | 75 | 180 |
| 75 | PTSSSTKKT QLQLEHLLLD LOMILNGINN YKNPKLTAML TKKFAMPKKA TELKHLQCLE EELKPLEEVL NLAQSKNFHF EPRDVVSNIN VFVLELKGSE TTFMCEYADE TATIVEFLNR WITFSQSIIS TLT | 76 | 181 |
| 76 | PTSSSTKKT QLQLEHLLLD LQMILNGINN YKNPKLTAML TKQFYMPKKA TELKHLQCLE RELKPLEEVL NLAQSKNFHF DPRDVGSNIN VFVLELKGSE TTFMCEYADE TATIVEFLNR WITFSQSIIS TLT | 77 | 182 |
| 77 | PTSSSTKKT QLQLEHLLLD LQMILNGINN YKNPKLTAML TKEFYMPKKA TELKHLQCLE RELKPLEEVL NLAQSKNFHF DPRDWVSNIN VFVLELKGSE TTFMCEYADE TATIVEFLNR WITFSQSIIS TLT | 78 | 183 |
| 78 | PTSSSTKKT QLQLEHLLLD LQMILNGINN YKNPELTAML TKKFYMPKKA TELKHLOCLE EELKPLEEVL NLAQSKNFHF EPRDVVSNIN VFVLELKGSE TTFMCEYADE TATIVEFLNR WITFSQSIIS TLT | 79 | 184 |

TABLE 2-continued

Sequences of interleukin-2 analogs

| Analog | Protein Sequence | SEQ ID NO of Proteins | SEQ ID NO of Nucleotides |
|---|---|---|---|
| 79 | PTSSSTKKT QLQLEHLLLD LQMILNGINN YKNPELTAML TKKFYMPKKA TELKHLQCLE EELKPLEEVL NLAHSKNFHF EPRDVVSNIN VFVLELKGSE TTFMCEYADE TATIVEFLNR WITFSQSIIS TLT | 80 | 185 |
| 80 | PTSSSTKKT QLQLEHLLLD LQMILNGINN YKNPELTAML TKKFYMPKKA TELKHLQCLE EELKPLEEVL NLAHSKNFHF EGRDVVSNIN VFVLELKGSE TTFMCEYADE TATIVEFLNR WITFSQSIIS TLT | 81 | 186 |
| 81 | PTSSSTKKT QLQLEHLLLD LQMILNGINN YKNPELTAML TKKFYMPKKA TELKHLQCLE EELKPLEEVL NLAHSKNFHF EVRDVVSNIN VFVLELKGSE TTFMCEYADE TATIVEFLNR WITFSQSIIS TLT | 82 | 187 |
| 82 | PTSSSTKKT QLQLEHLRLD LEMILNGINN YKNPKLTRML TFKFYMPKKA TELKHLQCLE EELKPLEEVL NLAQSKNFHF DPRDEVSNIN VFVLELKGSE TTFMCEYADE TATIVEFLNR WITFSQSIIS TLT | 83 | 188 |
| 83 | PTSSSTKKT QLQLEHLRRD LEMILNGINN YKNPKLTRML TFKFYMPKKA TELKHLQCLE EELKPLEEVL NLAQSKNFHF DPRDEVSNIN VFVLELKGSE TTFMCEYADE TATIVEFLNR WITFSQSIIS TLT | 84 | 189 |
| 84 | PTSSSTKKT QLQLEHLRLD LEMILNGINN YKNPKLTRML TFKFYMPKKA TELKHLQCLE EELKPLEEVL NLAQSKNFHV DPRDEVSNIN VFVLELKGSE TTFMCEYADE TATIVEFLNR WITFSQSIIS TLT | 85 | 190 |
| 85 | PTSSSTKKT QLQLEHLLLD LQMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 86 | 191 |
| 86 | PTSSSTKKT QLQLEHLRLD LEMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 87 | 192 |
| 87 | PTSSSTKKT QLQLEHLRRD LEMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 88 | 193 |
| 88 | PTSSSTKKT QLQLEHLLLD LQMILNGINN YKNPKLTRML TFKFYMPKKA TELKHLQCLE DELKPLEEVL NLAQSKNFHF EPRDVVSNIN VFVLELKGSE TTFMCEYADE TATIVEFLNR WITFSQSIIS TLT | 89 | 194 |
| 89 | PTSSSTKKT QLQLEHLLLD LQMILNGINN YKNPKLTAML TFKFYMPKKA TELKHLQCLE EELKPLEQVL NLAQSKNFHF EPRDVVSNIN VFVLELKGSE TTFMCEYADE TATIVEFLNR WITFSQSIIS TLT | 90 | 195 |
| 90 | PTSSSTKKT QLQLEHLLLD LQMILNGINN YKNPKLTRML TWKFYMPKKA TELKHLQCLE EELKPLEEVL NLAQSKNFHF EPRDVVSNIN VFVLELKGSE TTFMCEYADE TATIVEFLNR WITFSQSIIS TLT | 91 | 196 |
| 91 | PTSSSTKKT QLQLEHLLLD LQMILNGINN YKNPKLTRML TFKFYMPKKA TELKHLQCLE QELKPLEEVL NLAQSKNFHF EPRDVVSNIN VFVLELKGSE TTFMCEYADE TATIVEFLNR WITFSQSIIS TLT | 92 | 197 |
| 92 | PTSSSTKKT QLQLEHLLLD LQMILNGINN YKNPKLTRML TFKFYMPKKA TELKHLQCLE EELKPLEEVL NLAQSKNFHF EPRDVVSNIN TFVLELKGSE TTFMCEYADE TATIVEFLNR WITFSQSIIS TLT | 93 | 198 |
| 93 | PTSSSTKKT QLQLEHLLLD LQMILNGINN YKNPKLTRML TFKFYMPKKA TELKHLQCLE EELKPLEEVL NLAQSKNFHF | 94 | 199 |

TABLE 2-continued

Sequences of interleukin-2 analogs

| Analog | Protein Sequence | SEQ ID NO of Proteins | SEQ ID NO of Nucleotides |
|---|---|---|---|
| | EPREVVSNIN TFVLELKGSE TTFMCEYADE TATIVEFLNR WITFSQSIIS TLT | | |
| 94 | PTSSSTKKT QLQLEHLLLD LQMILNGINN YKNPKLTRML TFKFYMPKKA TELKHLQCLE EELKPLEEVL NLAQSKNFHF EPRDVVSNIN VFVFEFKGSE TTFMCEYADE TATIVEFLNR WITFSQSIIS TLT | 95 | 200 |
| 95 | PTSSSTKKT QLQLEHLLLD LQMILNGINN YKNPKLTRML TFKFYMPKKA TELKHLQCLE EELKPLEEGL NLAQSKNFHF EPRDVVSNIN VFVLELKGSE TTFMCEYADE TATIVEFLNR WITFSQSIIS TLT | 96 | 201 |
| 96 | PTSSSTKKT QLQLEHLLLD LQMILNGINN YKNPKLTRML TFKFYMPKKA TELKHLQCLE EELKPLEEGL NLAASKNFHF EPRDVVSNIN VFVLELKGSE TTFMCEYADE TATIVEFLNR WITFSQSIIS TLT | 97 | 202 |
| 97 | PTSSSTKKT QLQLEHLLLD LQMILNGINN YKNPKLTAML TFKFYMPKKA TELKHLQCLE EELKPLEEVL NLAQSKNFHF DPRDLISNIN VFVLELKGSE TTFMCEYADE TATIVEFLNR WITFSQSIIS TLT | 98 | 203 |
| 98 | PTSSSTKKT QLQLEHLLLD LQMILNGINN YKNPKLTAML TFKFYMPKKA TELKHLQCLE EELKPLEEVL NLAQSKNFHF EPRDVISNIN VFVLELKGSE TTFMCEYADE TATIVEFLNR WITFSQSIIS TLT | 99 | 204 |
| 99 | PTSSSTKKT QLQLEHLLLD LQMILNGINN YKNPKLTAML TFKFYMPKKA TELKHLQCLE EELKPLEEVL NLAQSKNFHF EPRDLVSNIN VFVLELKGSE TTFMCEYADE TATIVEFLNR WITFSQSIIS TLT | 100 | 205 |
| 100 | PTSSSTKKT QLQLEHLLLD LQMILNGINN YKNPKLTRML TFKFYMPKKA TELKHLQCLE EELKPLEEVL NLAQSKNFHF EPRDYVSNIN VFVLELKGSE TTFMCEYADE TATIVEFLNR WITFSQSIIS TLT | 101 | 206 |
| 101 | PTSSSTKKT QLQLEHLLLD LQMILNGINN YKNPKLTRML TFKFYMPKKA TELKHLQCLE EELKPLEEVL NLAQSKNFHF EPRDLASNIN VFVLELKGSE TTFMCEYADE TATIVEFLNR WITFSQSIIS TLT | 102 | 207 |
| 102 | PTSSSTKKT QLQLEHLLLD LQMILNGINN YKNPKLTRML TFKFYMPKKA TELKHLQCLE EELKPLEEVL NLAQSKNFHF EPRDVVSNIN VIVLELKGSE TTFMCEYADE TATIVEFLNR WITFSQSIIS TLT | 103 | 208 |
| 103 | PTSSSTKKT QLQLEHLRLD LEMILNGINN YKNPKLTAML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 104 | 209 |
| 104 | PTSSSTKKT QLQLEHLRLD LEMILNGINN YKNPKLTRML TFKFYMPKKA TELKHLQCLE DELKPLEEVL NLAQSKNFHF EPRDVVSNIN VFVLELKGSE TTFMCEYADE TATIVEFLNR WITFSQSIIS TLT | 105 | 210 |
| 105 | PTSSSTKKT QLQLEHLRLD LEMILNGINN YKNPKLTRML TFKFYMPKKA TELKHLQCLE EELKPLEDVL NLAQSKNFHF EPRDVVSNIN VFVLELKGSE TTFMCEYADE TATIVEFLNR WITFSQSIIS TLT | 106 | 211 |

Example 2: Expression of Interleukin-2 Analogs

A recombinant interleukin-2 analog under the control of T7 promoter was expressed using the expression vectors prepared in Example 1.

An expression E. coli strain, E. coli BL21 DE3 (E. coli B F-dcm ompT hsdS(rB-mB-) gal A(DE3); Novagen), was transformed with each recombinant interleukin-2 analog expression vector. As for the transformation method, a method recommended by Novagen was used. Each single colony, in which each recombinant expression vector was transformed, was collected, inoculated into a 2X Luria Broth medium containing ampicillin (50 μg/mL), and cultured at 37° C. for 15 hours. Each recombinant strain culture solution and the 2× LB medium containing 30% glycerol were mixed at a 1:1 (v/v) ratio, and each 1 mL of the mixture was dispensed into a cryo-tube, and stored at −150° C. This was used as a cell stock for the production of a recombinant protein.

For the expression of each recombinant interleukin-2 analog, one vial of each cell stock was dissolved, inoculated into 500 mL of 2× LB, and cultured with shaking at 37° C. for 14 to 16 hours. When the absorbance value at 600 nm reached 4.0 or higher, the culture was terminated, and this was used as a seed culture solution. The seed culture was inoculated into 1.6 L of a fermentation medium, and initial fermentation was started Using a 5 L fermentor (Bioflo-320, NBS, USA). Culture conditions were maintained at a pH of 6.70 using a temperature of 37° C., an air volume of 2.0 L/min (1 vvm), a stirring speed of 650 rpm, and 30% aqueous ammonia. As for the fermentation process, when nutrients in the culture medium were limited, fed-batch culture was performed by adding an additional medium (feeding solution). The growth of the strain was observed by absorbance, and a final concentration of 500 μM IPTG was introduced at an absorbance value of 70 or higher. The culture was performed further until for about 23 to 25 hours after the introduction of IPTG, and after termination of the culture, and the recombinant strain was recovered using a centrifuge and stored at −80° C. until use.

Example 3: Extraction and Refolding of Interleukin-2 Analogs

In order to convert the interleukin-2 analogs from the interleukin-2 analog expressing *E. coli* obtained in Example 2 in a soluble form, cells were disrupted and refolded. Cell pellets corresponding to 100 mL of the culture were suspended in 1-200 mL of a lysis buffer solution (20 mM Tris-HCl (pH 9.0), 1 mM EDTA (pH 9.0), 0.2 M NaCl, 0.5% Triton X-100), and the recombinant *E. coli* cells were disrupted at 15,000 psi using a microfluidizer. After centrifugation at 13,900 g for 30 minutes, the supernatant was discarded, and the pellet was washed with 400 mL of a first washing buffer solution (50 mM Tris-HCl (pH 8.0), 5 mM EDTA (pH 9.0)). After centrifugation under the same conditions as above, the supernatant was discarded, and the pellet was washed with 400 mL of a second washing buffer solution (50 mM Tris-HCl (pH 8.0), 5 mM EDTA (pH 9.0), 2% Triton X-100). After centrifugation under the same conditions as above, the supernatant was discarded, and the pellet was washed with 400 mL of a third washing buffer solution (50 mM Tris-HCl (pH 8.0), 5 mM EDTA (pH 9.0), 1% sodium deoxycholate). After centrifugation under the same conditions as above, the supernatant was discarded, and the pellet was washed with 400 mL of a fourth washing buffer solution (50 mM Tris-HCl (pH 8.0), 5 mM EDTA (pH 9.0), 1 M NaCl). The resultant was subjected to centrifugation under the same conditions as above and washing, and *E. coli* inclusion bodies were obtained therefrom. The pellet of the washed inclusion bodies was resuspended in 400 mL of soluble/reducing buffer (6 M guanidine, 100 mM Tris (pH 8.0), 2 mM EDTA (pH 9.0), 50 mM DTT) and stirred at 50° C. for 30 minutes. To the soluble/reduced interleukin-2 analogs, 100 mL of distilled water was added to dilute the 6 M guanidine to 4.8 M guanidine, and then the resultant was centrifuged at 13,900 g for 30 minutes and the pellet discarded to obtain only the solution therein. To the diluted solution was additionally added 185.7 mL of distilled water, and the 4.8 M guanidine was diluted to 3.5 M guanidine, and the pH was adjusted to 5.0 using 100% acetic acid. The pH-adjusted solution was stirred at room temperature for one hour. The solution with precipitated impurities was centrifuged at 13,900 g for 30 minutes, and the supernatant was discarded and the pellet washed with a final washing buffer solution (3.5 M guanidine, 20 mM sodium acetate (pH 5.0), 5 mM DTT). The resultant was centrifuged under the same conditions as above to obtain a pellet. The washed interleukin-2 analogs were dissolved in 400 mL of a refolding buffer solution (6 mM guanidine, 100 mM Tris (pH 8.0), 0.1 mM $CuCl_2$). The refolding process was performed by stirring the mixed solution at 4° C. for 15 to 24 hours.

Example 4: Size-Exclusion Column Chromatography

The interleukin-2 analog refolding solution obtained in Example 3 was concentrated to less than 1 mL to be applied to a size-exclusion column for purification. The column was equilibrated with a buffer solution (2 M guanidine, 100 mM Tris (pH 8.0)) before introducing with the refolding solution and was eluted by flowing a buffer solution thereto after the introduction of the refolding solution. Since the eluted sample contained guanidine, it was replaced with a stabilized solution (10 mM sodium acetate (pH 4.5), 5% trehalose), and the purity was measured through RP-HPLC and peptide mapping analysis. The sample was used in the experiment when its measured purity reached 80% or higher.

Example 5: Evaluation of Binding Affinity of Interleukin-2 Analogs for Receptors In order to measure the binding affinity of the interleukin-2 analogs obtained in Example 4 for each of interleukin-2 alpha receptors and beta receptors, surface plasmon resonance measurement (BIACORE T200, GE Healthcare) was used. The binding affinity of the prepared analogs for the alpha receptors and beta receptors was measured, and the binding affinity of each of the prepared analogs was compared with that of interleukin-2 analog 01 (aldesleukin).

First, an anti-human immunoglobulin antibody (Abcam, #ab97221) was immobilized to CM5 chips (GE Healthcare) by as much as about 5,000 RU (resonance unit) through amine coupling, and then, the immunoglobulin antibody was finally immobilized by allowing the interleukin-2 alpha receptors (SYMANSIS, #4102H) or interleukin-2 beta receptors (SYMANSIS, #4122H), to each of which a human immunoglobulin Fc region was bound, to bind to each immunoglobulin antibody using an antigen-antibody binding reaction. Thereafter, the recombinant interleukin-2 analog prepared above was diluted at various concentrations and was flowed onto the CM5 chips, to which the interleukin-2 receptors were finally immobilized, to measure the binding affinity of each interleukin-2 receptor. The measurement of binding affinity consisted of measurements of an association rate constant ($k_a$) and a dissociation rate constant ($k_d$), in which the binding rate was measured by flowing each interleukin-2 analog at a flow rate of 10 L/min for 3 minutes while the dissociation rate was measured from each interleukin-2 receptor by flowing only the experimental buffer for the same period of time and at the same flow rate. After the measurement was completed, the binding affinity for the receptors was evaluated according to the 1:1 binding fitting model in the Biaevaluation program.

relative binding affinity($K_D$)(%)=binding affinity of analog 01(aldesleukin)($K_D$)/binding affinity of analog($K_D$)×100

In Table 3 below, "cannot be defined" indicates that the corresponding physical quantity cannot be defined for the corresponding receptor because no binding to the receptor was observed in the surface plasmon resonance measurement.

TABLE 3

Relative binding affinity of interleukin-2 analogs for interleukin-2 alpha or beta receptors compared to analog 01 (aldesleukin)

| Interleukin-2 Receptor | Test Material | Relative Binding Affinity (%) |
|---|---|---|
| Alpha Receptor | analog 01 | 100.0 |
| | analog 09 | 74.5 |
| | analog 12 | cannot be defined |
| | analog 13 | 1.1 |
| | analog 15 | cannot be defined |
| | analog 16 | 0.2 |
| | analog 17 | 29.6 |
| | analog 19 | cannot be defined |
| | analog 20 | cannot be defined |
| | analog 21 | cannot be defined |
| | analog 31 | 5.0 |
| | analog 34 | 9.4 |
| | analog 35 | 31.7 |
| | analog 41 | 121.3 |
| | analog 52 | cannot be defined |
| | analog 53 | cannot be defined |
| | analog 86 | 71.1 |
| | analog 88 | 101.5 |
| | analog 90 | 98.4 |
| | analog 91 | 7.9 |
| | analog 92 | 97.3 |
| | analog 93 | 92.8 |
| | analog 95 | 10.7 |
| | analog 96 | 14.9 |
| | analog 97 | 18.8 |
| | analog 98 | 7.7 |
| | analog 99 | 19.9 |
| | analog 100 | 29.1 |
| | analog 101 | 24.7 |
| | analog 102 | 151.4 |
| | analog 103 | 6.1 |
| | analog 104 | 122.4 |
| | analog 105 | 246.8 |
| Beta Receptor | analog 01 | 100.0 |
| | analog 09 | 337.4 |
| | analog 12 | 166.2 |
| | analog 13 | 148.6 |
| | analog 14 | 129.7 |
| | analog 15 | 98.1 |
| | analog 16 | 1261.8 |
| | analog 17 | 9.4 |
| | analog 18 | 35.3 |
| | analog 19 | 455.0 |
| | analog 20 | 156.5 |
| | analog 21 | 14,084.2 |
| | analog 24 | 37.9 |
| | analog 25 | 21.7 |
| | analog 31 | 235.7 |
| | analog 34 | 321.8 |
| | analog 35 | 232.7 |
| | analog 41 | 22,776.2 |
| | analog 52 | 3,821.1 |
| | analog 53 | 690.7 |
| | analog 55 | 3,025.7 |
| | analog 57 | 2,569.7 |
| | analog 58 | 7,771.2 |
| | analog 59 | 1,533.5 |
| | analog 61 | 1,039.1 |
| | analog 70 | 10,199.2 |
| | analog 71 | 17,083.8 |
| | analog 73 | 1,591.8 |
| | analog 74 | 8,153.4 |
| | analog 75 | 9,571.2 |
| | analog 76 | 1,040.4 |
| | analog 77 | 644.4 |
| | analog 84 | 710.7 |
| | analog 86 | 18,745.8 |
| | analog 88 | 13,856.6 |
| | analog 90 | 12,776.2 |
| | analog 91 | 7,361.9 |
| | analog 92 | 1,510.3 |
| | analog 93 | 696.8 |
| | analog 94 | 35.5 |
| | analog 95 | 17.1 |
| | analog 96 | 229.3 |
| | analog 97 | 3,019.4 |
| | analog 98 | 11,084.5 |
| | analog 99 | 1,509.1 |
| | analog 100 | 2,534.1 |
| | analog 101 | 113.1 |
| | analog 102 | 4,452.0 |
| | analog 103 | 13,100.0 |
| | analog 104 | 25,439.8 |
| | analog 105 | 26,837.8 |

Figure 1B:
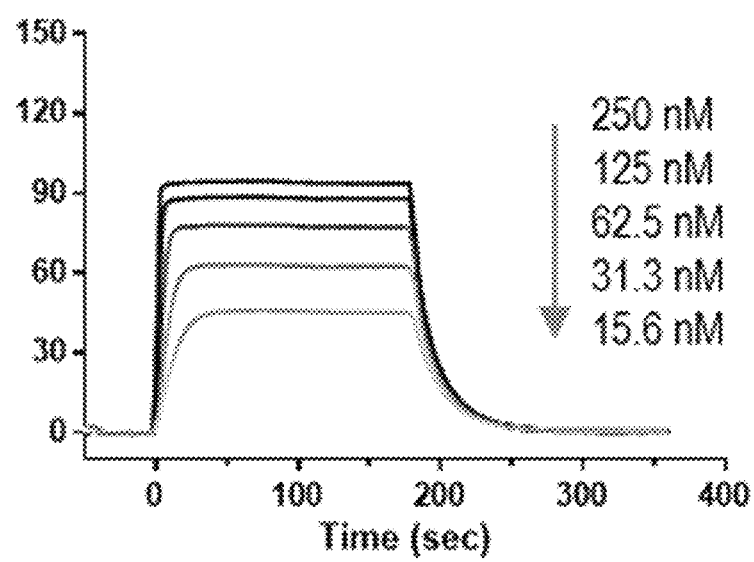
Figure 1C:
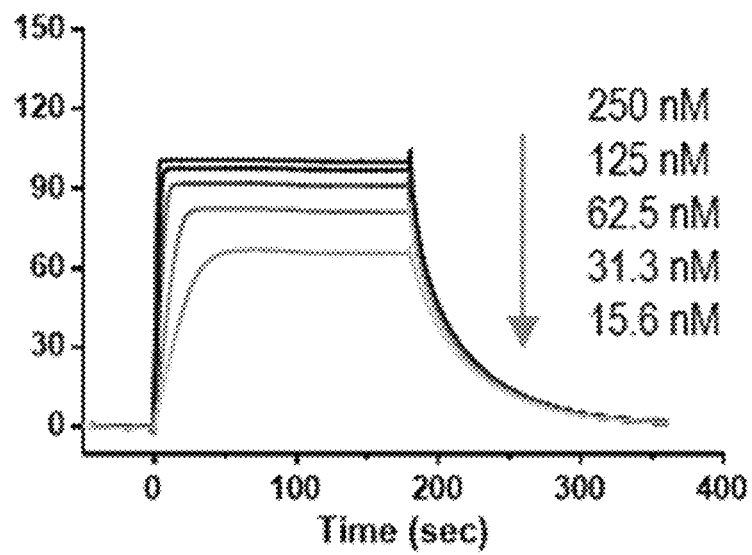
Figure 2A:
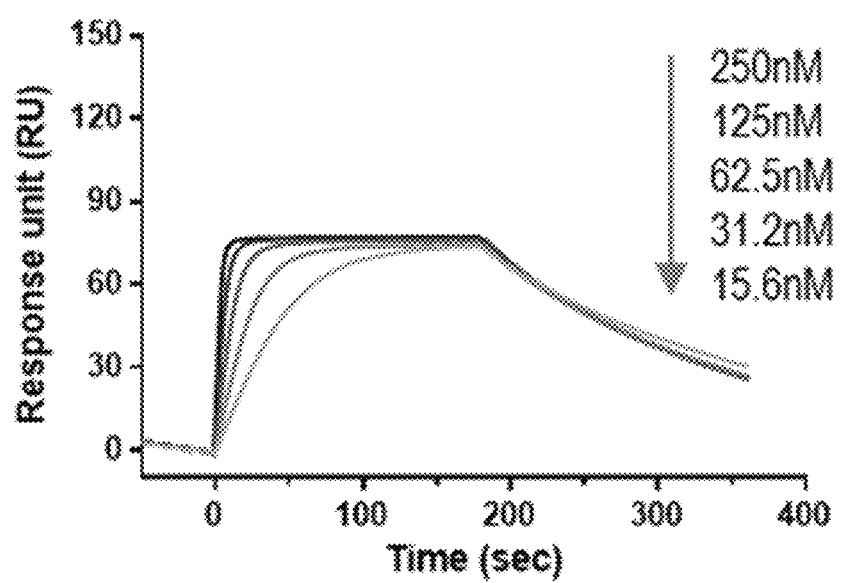
Figure 2B:
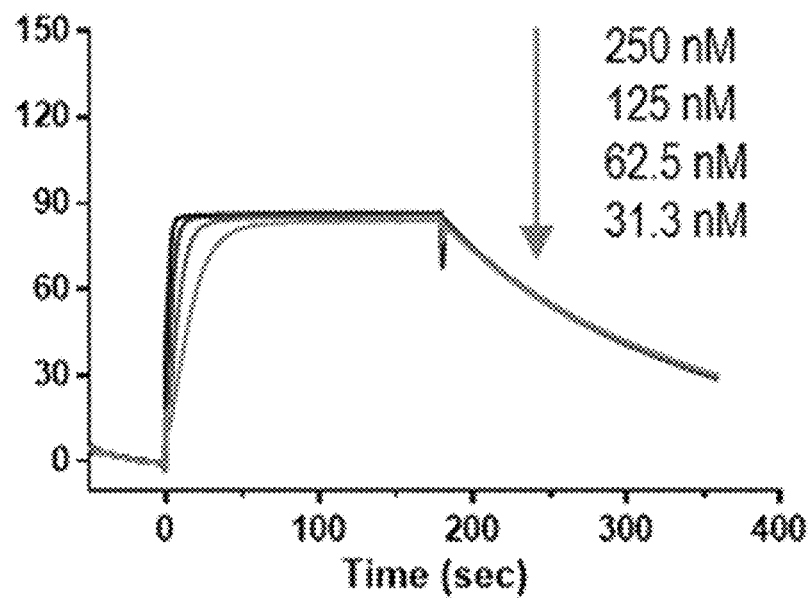
Figure 2C:
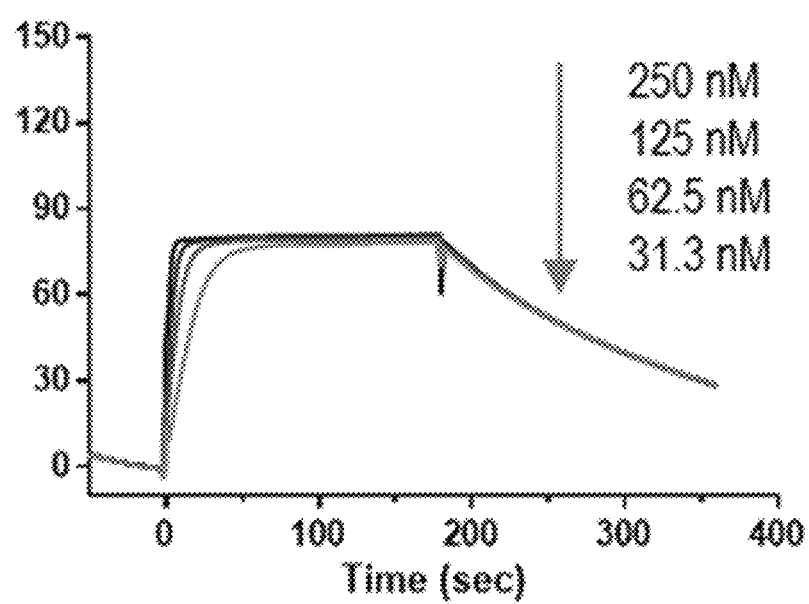

As explicitly shown in the test results (FIGS. 1 and 2 and Table 3), it was confirmed that the interleukin-2 analogs of the present invention had no binding affinity, increased/reduced binding affinity for interleukin-2 alpha receptors, etc., thus showing an altered binding affinity for interleukin-2 alpha receptors compared to native interleukin-2 or aldesleukin. In contrast, as for the interleukin-2 beta receptors, the interleukin-2 analogs of the present invention showed a stronger binding affinity of up to 100-fold compared to native interleukin-2 or aldesleukin. From the above results, it was confirmed that the amino acid sequence of the interleukin-2 analog has an effect on its binding to the interleukin-2 alpha or beta receptors. These results suggest that the binding affinity for interleukin-2 receptors can be altered by substituting an amino acid at a specific position.

These experimental results suggest that the interleukin-2 analogs according to the present invention have altered binding affinity for interleukin-2 alpha receptors and interleukin-2 beta receptors and thus can be used in the development of various drugs based on the same.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. An interleukin-2 analog comprising an amino acid sequence represented by General Formula 1 below:

[General Formula 1]

X1-P-T-S-S-T-K-K-T-Q-L-Q-L-E-H-L-X18-X19-D-L-X22-M-I-L-N-G-I-N-N-Y-K-N-P-K-L-T-X38-M-L-T-X42-X43-F-X45-M-P-K-K-A-T-E-L-K-H-L-Q-C-L-E-X61-E-L-K-P-L-E-X68-V-L-N-L-A-X74-S-K-N-F-H-X80-X81-P-R-X84-X85-X86-S-N-I-N-X91-X92-V-X94-E-X96-K-G-S-E-T-T-F-M-C-E-Y-A-D-E-T-A-T-I-V-E-F-L-N-R-W-I-T-F-S-Q-S-I-I-S-T-L-T (General Formula 1, SEQ ID NO: 212)

wherein in General Formula 1 above,

X1 is a deletion;
X18 is leucine (L) or arginine (R);
X19 is leucine (L) or tyrosine (Y);
X22 is glutamic acid (E) or glutamine (Q);
X38 is alanine (A);
X42 is alanine (A), phenylalanine (F), lysine (K), or tryptophan (W);
X43 is glutamic acid (E), lysine (K), or glutamine (Q);
X45 is alanine (A) or tyrosine (Y);
X61 is aspartic acid (D), glutamic acid (E), glutamine (Q), or arginine (R);
X68 is aspartic acid (D) or glutamic acid (E);
X74 is histidine (H) or glutamine (Q);
X80 is phenylalanine (F);
X81 is aspartic acid (D), glutamic acid (E), or arginine (R);
X84 is aspartic acid (D) or glutamic acid (E);
X85 is alanine (A), glutamic acid (E), glycine (G), leucine (L), valine (V), tryptophan (W), or tyrosine (Y);
X86 is alanine (A), glycine (G), isoleucine (I), or valine (V);
X91 is threonine (T) or valine (V);
X92 is phenylalanine (F);
X94 is phenylalanine (F) or leucine (L); and
X96 is phenylalanine (F) or leucine (L).

2. The interleukin-2 analog of claim 1, wherein the interleukin-2 analog comprises any one sequence selected from the group consisting of amino acid sequences of SEQ ID NOS: 54, 56, 58, 59, 72, 74, 76, 77, 78, 98, and 100.

3. The interleukin-2 analog of claim 1, wherein in General Formula 1 above,

X43 is lysine (K);
X45 is tyrosine (Y);
X61 is aspartic acid (D), glutamic acid (E), or glutamine (Q);
X68 is glutamic acid (E);
X74 is glutamine (Q);
X80 is phenylalanine (F);
X85 is leucine (L), valine (V), or tyrosine (Y);
X86 is isoleucine (I) or valine (V); and
X92 is phenylalanine (F).

4. The interleukin-2 analog of claim 3, wherein the interleukin-2 analog comprises any one sequence selected from the group consisting of amino acid sequences of SEQ ID NOS: 54, 72, 98, and 100.

5. The interleukin-2 analog of claim 1, wherein the interleukin-2 analog further comprises one or more amino acids at the C-terminus thereof.

* * * * *